United States Patent
Scott et al.

(10) Patent No.: US 6,630,503 B1
(45) Date of Patent: Oct. 7, 2003

(54) CELL ADHESION INHIBITORS

(75) Inventors: Daniel Scott, Weston, MA (US);
Wen-Cherng Lee, Lexington, MA (US); Russell C. Petter, Stow, MA (US); Mark Cornebise, Watertown, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/638,652

(22) Filed: Aug. 14, 2000

Related U.S. Application Data

(60) Provisional application No. 60/148,845, filed on Aug. 13, 1999.

(51) Int. Cl.$^7$ .................. A61K 31/40; A61K 31/404; A61K 31/4184; C07D 207/48; C07D 401/12
(52) U.S. Cl. .................. 514/423; 548/537; 548/307.4; 548/467; 514/388; 514/414
(58) Field of Search .................. 548/537; 514/423

(56) References Cited

U.S. PATENT DOCUMENTS

| 4,725,583 A | 2/1988 | Luly et al. |
| 4,826,815 A | 5/1989 | Luly et al. |
| 4,908,360 A | 3/1990 | Martin et al. |
| 5,260,277 A | 11/1993 | McKenzie |
| 5,314,902 A | 5/1994 | Tjoeng et al. |
| 5,399,570 A | 3/1995 | Klingler et al. |
| 5,403,836 A | 4/1995 | Blackburn et al. |
| 5,434,188 A | 7/1995 | Boschelli et al. |
| 5,770,573 A | 6/1998 | Arrhenius et al. |
| 5,922,755 A | 7/1999 | Tanaka et al. |

FOREIGN PATENT DOCUMENTS

| DE | 43 09 867 | 9/1994 | |
| EP | 0 021 234 B1 | 1/1981 | |
| EP | 0 460 679 B1 | 12/1991 | |
| EP | 0 357 192 B1 | 5/1992 | |
| EP | 0 519 748 B1 | 12/1992 | |
| WO | WO 89/09786 | 10/1989 | |
| WO | WO 91/09837 | 7/1991 | |
| WO | WO 92/00995 | 1/1992 | |
| WO | WO 92/08464 | 5/1992 | |
| WO | WO 93/08823 | 5/1993 | |
| WO | WO 93/09795 | 5/1993 | |
| WO | WO 93/12809 | 7/1993 | |
| WO | WO 94/02445 | 2/1994 | |
| WO | WO 94/15958 | 7/1994 | |
| WO | WO 95/15973 | 6/1995 | |
| WO | WO 96/22966 | 8/1996 | |
| WO | WO 97/03094 | 1/1997 | |
| WO | WO 98/04913 | 2/1998 | |
| WO | WO98/53814 | 12/1998 | ......... A61K/31/395 |
| WO | WO98/53817 | 12/1998 | ......... A61K/31/42 |
| WO | WO98/53818 | 12/1998 | ......... A61K/31/42 |
| WO | 99/06432 | 2/1999 | |
| WO | WO99/06434 | 2/1999 | ......... C07K/5/078 |
| WO | WO99/10312 | 3/1999 | ......... C07C/233/87 |
| WO | WO 99/26921 | 6/1999 | |
| WO | WO99/26922 | 6/1999 | ......... C07D/207/48 |
| WO | WO99/26923 | 6/1999 | ......... C07D/211/56 |
| WO | WO 99/61421 | 12/1999 | |

OTHER PUBLICATIONS

Abraham et al., "$\alpha_4$–Integrins Mediate Antigen–induced Late Bronchial Responses and Prolonged Airway Hyperresponsiveness in sheep", J Clin. Invest., vol. 93, pp. 776–787, (1994).

Bajusz et al., "Design and Synthesis of Peptide Inhibitors of Blood Coagulation", Folia Haematol., Leipzig, vol. 109, pp. 16–21, (1982).

Baldwin et al., "An Efficient Substitute for the $\alpha$–aminoadipoyl Moiety of $\delta$–(L–$\alpha$–amimoadipoyl)–L–cysteinyl–D–valine in the Enzymatic Synthesis of Penicillins", Tetrahedron, vol. 43, No. 18, pp. 4217–4220, (1987).

Chen et al., "Facile synthesis of N–protected peptide fragments using polymer–bound 1–hydroxybenzotriazole as an active ester", Chemical Abstracts, vol. 115, p. 1003, 115:159756r (1991).

Chisholm et al., "Monoclonal antibodies to the integrin $\alpha$–4 subunit inhibit the murine contact hypersensitivity response", European Joural of Immunology, vol. 23, pp. 682–688, (1993).

Elices et al., "Expression and Functional Significance of Alternatively Spliced CS1 Fibronectin in Rheumatoid Arthritis Microvasculature", The Journal of Clinical Investigation, vol. 93, pp. 405–416, (1994).

Ferguson et al., "Antigen–Independent Processes in Antigen–Specific Immunity", The Journal of Immunology, vol. 150, No. 4, pp. 1172–1182, (1993).

Ferguson et al., "Two integrin–binding peptides abrogate T cell–mediated immune responses in vivo", Proceedings of the National Academy of Sciences USA, vol. 88, pp. 8072–8076, (1991).

Goodman et al., "Synthesis Conformation of Sequential Polypeptides of L–Alanine and beta–Aminobutyric Acid", Macromolecules, vol. 9, No. 1, pp. 1–6, (1976).

Greenstein et al., "Chemistry of the Amino Acids," John Wiley and Sons, Inc., vol. 2, pp. 1162–1186. Year Not Available.

(List continued on next page.)

Primary Examiner—Laura L. Stockton
(74) Attorney, Agent, or Firm—Fish & Richardson P.C.

(57) ABSTRACT

A cell adhesion inhibitor of the general formula:

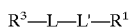

$$R^3\text{—L—L'—}R^1$$

is disclosed. An inhibitor of the present invention interacts with VLA-4 molecules and inhibits VLA-4 dependent cell adhesion. Also disclosed are methods for preparing and using such a cell adhesion inhibitor, as well as pharmaceutical compositions containing the same.

7 Claims, No Drawings

OTHER PUBLICATIONS

Gruszecki et al., "Diacylamine–perfekte Acylierungsmittel für die Peptidsynthese", Liebigs Ann. Chem., pp. 331–336, (1988).

Hemler, "VLA Proteins in the Integrin Family: Structures. Functions. and Their Role on Leukocytes", Annual Review of Immunology, vol. 8, pp. 365–400, (1990).

Jiang et al., "Approaches Toward the Total Synthesis of Astins A, B, And C", Tetrahedron Letters, vol. 35, No. 14, pp. 2121–2124, (1994).

Kim et al., "Inhibition of $^{125}$I–Labeled Ristocetin Binding to *Micrococcus luteus* Cells by the Peptides Related to Bacterial Cell Wall Mucopeptide Precursors: Quantitative Structure–Activity Relationships", Journal of Medical Chemistry, vol. 32, No. 1, pp. 84–93, (1989).

Komoriya et al., "The Minimal Essential Sequence for a Major Cell Type–specific Adhesion site (CS1) within the Alternatively Spliced . . . ", Journal of Biological Chemistry, vol. 266, No. 23, pp. 15075–15079, (1991).

Lampi, et al., "Comparison of Cell–Permeable Calpain Inhibitors and E64 in Reduction of Cataract in Cultured Rat Lenses", Toxicology and Applied Pharmacology, vol. 117, pp. 53–57, (1992).

Lobb et al., "The Pathophysiologic Role of α4 Integrins in Vivo", The Journal of Clinical Investigation, vol. 94, pp. 1722–1728, (1994).

Melmon et al., "III Drug Interactions", The Pharmacological Basis of Therapeutics, $6^{th}$ Edition, MacMillan Publishing Co., Inc. ©, 1980, pp. 1738–1740.

Molossi et al., "Blockade of Very Late Antigen–4 Integrin Binding to Fibronectin with Connecting Segment–1 Peptide Reduces Accelerated Coronary Arteriopathy . . . ", Journal of Clinical Investigation, vol. 95, pp. 2601–2610, (1995).

Morales–Ducret et al., "$α_4/β1$ Integrin (VLA–4) Ligands in Arthritis Vascular Cell Adhesion Molecule–1 Expression in Synovium and on . . . ", The Journal of Immunology, vol. 149, No. 4, pp. 1424–1431, (1992).

Narumiya et al., "Pre–B cells adhere to fibronectin via interactions of integrin α5/αv with RGDS as well as of integrin α4 with two distinct V region sequences at its different biding sites", Intl. Immun., vol. 6, No. 1, pp. 139–147, (1994).

Nowlin et al., "A Novel Cyclic Pentapeptide Inhibits α4β1 and α5β1 Integrin–mediated Cell Adhesion", The Journal of Biological Chemistry, vol. 25, No. 27, pp. 20352–20359, (1993).

Sawyer, T. K., "Peptidomimetic Design and Chemical Approaches to Peptide Metabolism", Peptide–Based Drug Design: controlling transport and metabolism ©, 1995, ACS Professional Reference Book, pp. 387–422.

Subasinghe et al., "Synthesis of Acyclic and Dehydroaspartic Acid Analogues of Ac–Asp–Glu–OH and Their Inhibition of Rat Brain N–Acetylated α–Linked Acidic Dipeptidase (NAALA Dipeptidase)", Journal of Medicinal Chemistry, vol. 33, No. 10, pp. 2734–2744, (1990).

Thierry et al., "Synthesis and Activity of NAcSerAspLysPro Analogues on Cellular Interactions between T–Cell and Erythrocytes in Rosette Formation," Journal of Medical Chemistry, vol. 33, pp. 2122–2127, (1990).

Wayner et al., "Activation–dependent Recognition by Hematopoietic Cells of the LDV Sequence in the V Region of Fibronectin", The Journal of Cell Biology, vol. 16, No. 2, pp. 489–497, (1992).

Yednock et al., "Prevention of experimental autoimmune encephalomyelitis by antibodies against α4β1 integrin", Nature, vol. 356, pp. 63–66, (1992).

Lin, Ko–Chung, et al., "Selective, Tight Binding Inhibitors of Integrin α4β1 That Inhibit Allergic Airway Responses", Journal of Medicinal Chemistry, vol. 42, No. 5, pp. 920–934, (1999).

Zimmerman, Craig N., "Peptide and peptodomimetic inhibitors of VLA–4", Expert Opinion of Therapeutic Patents, Ashley Publication, GB, vol. 9, No. 2, pp. 129–133, (1999).

CELL ADHESION INHIBITORS

CROSS REFERENCE TO RELATED APPLICATIONS

Pursuant to 35 USC §119(e), this application claims the benefit of prior U.S. provisional application No. 60/148,845, filed Aug. 13, 1999.

BACKGROUND

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hemopoietic cells out of blood vessels and to the site of injury. As such, cell adhesion plays a role in pathologies such as inflammation and immune reactions in mammals.

Investigations into the molecular basis for cell adhesion have revealed that various cell-surface macromolecules—collectively known as cell adhesion molecules or receptors—mediate cell-cell and cell-matrix interactions. For example, proteins of the superfamily called "integrins" are key mediators in adhesive interactions between hematopoietic cells and their microenvironment (M. E. Hemler, "VLA Proteins in the Integrin Family: Structures, Functions, and Their Role on Leukocytes.", Ann. Rev. Immunol., 8, p. 365 (1990)). Integrins are non-covalent heterodimeric complexes consisting of two subunits called α and β. There are at least 12 different a subunits (α–α6, α-L, α-M, α-X, α-IIB, α-V and α-E) and at least 9 different β(β1–β9) subunits. Based on the type of its α and β subunit components, each integrin molecule is categorized into a subfamily.

α4β1 integrin, also known as very late antigen-4 ("VLA-4"), CD49d/CD29, is a leukocyte cell surface receptor that participates in a wide variety of both cell-cell and cell-matrix adhesive interactions (M. E. Hemler, Ann. Rev. Immunol., 8, p. 365 (1990)). It serves as a receptor for the cytokine-inducible endothelial cell surface protein, vascular cell adhesion molecule-1 ("VCAM-1"), as well as to the extracellular matrix protein fibronectin ("FN") (Ruegg et al., J. Cell Biol., 177, p. 179 (1991); Wayner et al., J. Cell Biol., 105, p. 1873 (1987); Kramer et al., J. Biol. Chem., 264, p. 4684 (1989); Gehlsen et al. Science, 24, p. 1228 (1988)). Anti-VLA4 monoclonal antibodies ("mAb's") have been shown to inhibit VLA4-dependent adhesive interactions both in vitro and in vivo (Ferguson et al. Proc. Natl. Acad. Sci., 88, p. 8072 (1991); Ferguson et al., J. Immunol., 150, p. 1172 (1993)). Results of in vivo experiments suggest that this inhibition of VLA-4-dependent cell adhesion may prevent or inhibit several inflammatory and autoimmune pathologies (R. L. Lobb et al., "The Pathophysiologic Role of α4 Integrins In Vivo", J. Clin. Invest., 94, pp. 1722–28 (1994)).

Despite these advances, there remains a need for small, specific inhibitors of VLA-4-dependent cell adhesion. Ideally, such inhibitors may be orally administered. Such compounds would provide useful agents for treatment, prevention or suppression of various pathologies mediated by cell adhesion and VLA-4 binding.

SUMMARY

The present invention relates to novel non-peptidic compounds that specifically inhibit the binding of ligands to VLA-4. These compounds are useful for inhibition, prevention and suppression of VLA-4-mediated cell adhesion and pathologies associated with that adhesion, such as inflammation and immune reactions. The compounds of this invention may be used alone or in combination with other therapeutic or prophylactic agents to inhibit, prevent or suppress cell adhesion. This invention also provides pharmaceutical compositions containing the compounds of this invention and methods of using the compounds and compositions of the invention for inhibition of cell adhesion.

According to one embodiment of this invention, these novel compounds, compositions and methods are advantageously used to treat inflammatory and immune diseases. The present invention also provides methods for preparing the compounds of this invention and intermediates therefor.

An aspect of this invention relates to cell adhesion inhibitors of formula (I):

$$R^3—L—L'—R^1 \qquad (I)$$

$R^1$ is H, $C_{1-10}$ alkyl, $C_{2-10}$ alkenyl, $C_{2-10}$ alkynyl, Cy, Cy—$C_{1-10}$ alkyl, Cy—$C_{1-10}$ alkenyl, or Cy—$C_{1-10}$ alkynyl.

L' is a hydrocarbon linker moiety having 1–5 carbon chain atoms and is (i) optionally interrupted by, or terminally attached to, one or more (e.g., 1, 2, or 3) of the following groups: —C(O)—, —O—C(O)—, —C(O)—O—, —C(O)—NR$^c$, —NR$^c$—C(O)—, —NR$^c$—C(O)—NR$^d$—, —NR$^c$—(O)—O—, —O—C(O)—NR$^c$—, —S(O)$_m$—, —SO$_2$—NR$^c$—, —NR$^c$—SO$_2$—, —NR$^c$—C(NR$^m$)—, —O—, —NR$^c$—, and —Cy; or (ii) optionally substituted with one or more substituents independently selected from R$^b$.

L is a hydrocarbon linker moiety having 1–14 carbon chain atoms and is (i) optionally interrupted by, or terminally attached to, one or more (e.g., 1–5, 1–4, or 1–3) of the following groups: —C(O)—, —O—C(O)—, —C(O)—O—, —C(O)—NR$^c$—, —NR$^c$—C(O)—, —NR$^c$—C(O)—NR$^d$—, —NR$^c$—C(O)—O—, —O—C(O)—NR$^c$, —S(O)$_m$—, —SO$_2$—NR$^c$—, —NR$^c$—SO$_2$—, —O—, —NR$^c$—, and Cy; or (ii) optionally substituted with one or more substituents independently selected from R$^b$.

$R^3$ is alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkenoxy, alkynoxy, aralkoxy, aryl-substituted alkenoxy, aryl-substituted alkynoxy, alkylamino, alkenylamino, alkynylamino, aryl-substituted alkylamino, aryl-substituted alkenylamino, aryl-substituted alkynylamino, aryloxy, arylamino, heterocyclyl, heterocyclyl-substituted alkyl, heterocyclyl-substituted amino, carboxyalkyl substituted aralkyl, or oxocarbocyclyl-fused aryl; or $R^3$ is a moiety of formula (i):

$Y^5$ is —CO—, —O—CO—, —SO$_2$— or —PO$_2$—.

Each of $R^4$ and $R^6$, independently, is alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkenoxy, alkynoxy, aralkoxy, aryl-substituted alkenoxy, aryl-substituted alkynoxy, alkylamino, alkenylamino, alkynylamino, aryl-substituted alkylamino, aryl-substituted alkenylamino, aryl-substituted alkynylamino, aryloxy, arylamino, heterocyclyl, heterocyclyl-substituted alkyl, heterocyclyl-substituted amino, carboxyalkyl substituted aralkyl, oxocarbocyclyl-fused aryl, or an amino acid side chain selected from the group consisting of arginine, asparagine, glutarmine, S-methyl cysteine, methionine and corresponding sulfoxide and sulfone derivatives thereof, cyclohexylalanine, leucine, isoleucine, allo-isoleucine, tert-leucine, norleucine, phenylalanine, phenylglycine, tyrosine, tryptophan, proline, alanine, ornithine, histidine, glutamine, norvaline, valine, threonine, serine, beta-cyanoalanine, 2-aminobutyric acid and allothreonine.

$R^5$ is hydrogen, aryl, alkyl, alkenyl, alkynyl, cycloalkyl, cycloalkenyl, or aryl-substituted alkyl. Note that $R^5$ and $R^6$ may be taken together with the atoms to which they are attached to form a heterocycle of 5 to 7 members.

Each of the above-stated Cy represents cycloalkyl, cycloalkenyl, heterocyclyl, aryl, or heteroaryl. Each of the above-stated alkyl, alkenyl and alkynyl is optionally substituted with one to four substituents independently selected from $R^a$. Further, each of the above-stated cycloalkyl, cycloalkenyl, heterocyclyl, aryl, and heteroaryl is optionally substituted with one to four substituents independently selected from $R^b$.

$R^a$ is selected from the group consisting of: Cy (which is optionally substituted with one to four substituents independently selected from $R^b$), —$OR^c$, —$NO_2$, -halogen, —$S(O)_m R^c$, —$SR^c$, —$S(O)_2 OR^c$, —$S(O)_2 NR^c R^d$, —$NR^c R^d$, —$O(CR^e R^f)_n NR^c R^d$, —$C(O)R^d$, —$CO_2 R^c$, —$P(O)(OR^c)(OR^d)$, —$P(O)(R^c)(OR^d)$, —$S(O)_m OR^c$, —$C(O)NR^c R^j$, —$CO_2(CR^e R^f)_n CONR^c R^d$, —$OC(O)R^c$, —CN, —$NR^c C(O)R^d$, —$OC(O)NR^c R^d$, —$NR^c C(O)OR^d$, —$NR^c C(O)NR^d R^e$, —$CR^c(NOR^d)$, —$CF_3$, —$OCF_3$, and oxo.

$R^b$ is a group selected from $R^a$, $C_{1-10}$ alkyl, $C_{2-10}$ alkenyl, $C_{2-10}$ alkynyl, aryl-$C_{1-10}$ alkyl, and heteroaryl-$C_{1-10}$ alkyl; wherein each of alkyl, alkenyl, alkynyl, aryl, and heteroaryl is optionally substituted with a group independently selected from $R^g$.

Each of $R^c$, $R^d$, $R^e$, and $R^f$, independently, is selected from H, $C_{1-10}$ alkyl, $C_{2-10}$ alkenyl, $C_{2-10}$ alkynyl, Cy, and Cy—$C_{1-10}$ alkyl; wherein each of alkyl, alkenyl, alkynyl and Cy is optionally substituted with one to four substituents independently selected from $R^g$.

$R^g$ is halogen, amino (including —$NH_2$, (mono- or di-)alkylamino, (mono- or di-)alkenylamino, (mono- or di-)alkynylamino, (mono- or di-)cycloalkylamino, (mono- or di-)cycloalkenylamino, (mono- or di-)heterocyclylamino, (mono- or di-)arylamino, and (mono- or di-)heteroarylamino), carboxy, —COO—$C_{1-4}$ alkyl, —$P(O)(OH)_2$, —$P(O)(OH)(O—C_{1-4}$ alkyl), —$P(O)(C_{1-4}$ alkyl)$_2$, —$P(O)(OH)(C_{1-4}$ alkyl), —$P(O)(O—C_{1-4}$ alkyl)($C_{1-4}$ alkyl), —$SO_2—C_{1-4}$ alkyl, —CO—$NH_2$, —CO—NH($C_{1-4}$ alkyl), —CO—N($C_{1-4}$ alkyl)$_2$, —$C_{1-4}$ alkyl, —$C_{1-4}$ alkoxy, aryl, aryl-$C_{1-4}$ alkoxy, hydroxy, $CF_3$, and aryloxy.

$R^m$ is H, $C_{1-10}$ alkyl, $C_{2-10}$ alkenyl, $C_{2-10}$ alkynyl, Cy, Cy—$C_{1-10}$ alkyl, $C_{1-10}$ acyl, $C_{1-10}$ alkyl-sulfonyl, or $C_{1-10}$ alkoxy.

$R^j$ is H, $C_{1-10}$ alkyl, $C_{2-10}$ alkenyl, $C_{2-10}$ alkynyl, cyano, aryl, aryl-$C_{1-10}$ alkyl, heteroaryl, heteroaryl-$C_{1-10}$ alkyl, or —$SO_2 R^k$ (with $R^k$ being $C_{1-10}$ alkyl, $C_{2-10}$ alkenyl, $C_{2-10}$ alkynyl, or aryl).

$R^c$ and $R^d$ can be taken together with the atoms to which they are attached and optionally form a heterocyclic ring of 5 to 7 members that contains 0–2 additional heteroatoms independently selected from O, N and S. Similarly, $R^e$ and $R^f$ can be taken together with the atoms to which they are attached optionally form a ring of 5 to 7 members that contains 0–2 additional heteroatoms independently selected from O, S and N.

m is 0, 1, or 2; and n is an integer from 1 to 10.

Note that when L is saturated (e.g., a $C_{1-4}$ alkylene chain) and has 1–4 carbon chain atoms, L must contain a heteroatom selected from O, S, and N; or $R^3$ must contain the moiety o-methylphenyl-ureido-phenyl-$CH_2$—; or $R^1$ must contain only one cyclic group (e.g., cycloalkyl, cycloalkenyl, heterocyclyl, aryl, or heteroaryl).

In one embodiment, the compounds of this invention contain $R^1$ with the formula: $Z^1$—$L^a$—$Z^2$, wherein $Z^1$ is cycloalkyl, cycloalkyl-$C_{1-10}$ alkyl, cycloalkenyl, cycloalkenyl-$C_{1-10}$ alkyl, aryl, aryl-$C_{1-10}$ alkyl, heterocyclyl, heterocyclyl-$C_{1-10}$ alkyl, heteroaryl, or heteroaryl-$C_{1-10}$ alkyl; $L^a$ is —C(O)—, —O—C(O)—, —C(O)—O—, —C(O)—$NR^c$—, —$NR^c$—C(O)—, —$NR^c$—C(O)—$NR^d$—, —$NR^c$—C(O)—O—, —O—C(O)—$NR^c$—, —$S(O)_m$—, —$SO_2$—$NR^c$—, —$NR^c SO_2$—, —O—, —$NR^c$—, or a bond (m, $R^c$ and $R^d$ have been defined above); and $Z^2$ is cycloalkyl, cycloalkyl-$C_{1-10}$ alkyl, cycloalkenyl, cycloalkenyl-$C_{1-10}$ alkyl, aryl, aryl-$C_{1-10}$ alkyl, heterocyclyl, heterocyclyl-$C_{1-10}$ alkyl, heteroaryl, heteroaryl-$C_{1-10}$ alkyl or a bond. In one embodiment, $Z^1$ is cycloalkyl, cycloalkyl-$C_{1-10}$ alkyl, aryl, aryl-$C_{1-10}$ alkyl, heterocyclyl, heterocyclyl-$C_{1-10}$ alkyl, heteroaryl, or heteroaryl-$C_{1-10}$ alkyl; $L^a$ is —O—C(O)—, —C(O)—O—, —C(O)—$NR^c$—, —$NR^c$—C(O)—, —$SO_2$—, —$SO_2$—$NR^c$—, —$NR^c$—$SO_2$—, —O—, —$NR^c$—, or a bond; and $Z^2$ is aryl, aryl-$C_{1-10}$ alkyl, heterocyclyl, heterocyclyl-$C_{1-10}$ alkyl, or a bond. In one embodiment, $Z^1$ is aryl, aryl-$C_{1-5}$ alkyl, heterocyclyl, heterocyclyl-$C_{1-5}$ alkyl, heteroaryl, or heteroaryl-$C_{1-5}$ alkyl; $L^a$ is —O—C(O)—, —C(O)—O—, —C(O)—$NR^c$—, —$NR^c$—C(O)—, —$SO_2$—, or a bond; and $Z^2$ is heterocyclyl, heterocyclyl-$C_{1-5}$ alkyl, or a bond. In one embodiment, $Z^1$ is phenyl optionally substituted with Cy, —CO—$R^d$, halogen, oxo, aryl-substituted alkenyl; $L^a$ is —O—C(O)—, —C(O)—O—, —C(O)—$NR^c$, —$NR^c$—C(O), or —$SO_2$—; and $Z^2$ is heterocyclyl or a bond.

In one embodiment, the compounds of this invention contain $R^1$ of formula (ii):

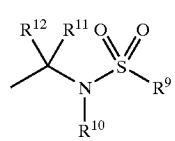

(ii)

wherein $R^9$ is $C_{1-10}$ alkyl, $C_{2-10}$ alkenyl, $C_{2-10}$ alkynyl, Cy, Cy—$C_{1-10}$ alkyl, Cy—$C_{2-10}$ alkenyl, or Cy—$C_{2-10}$ alkynyl; each of $R^{10}$ and $R^{11}$, independently, is hydrogen, aryl, alkyl, alkenyl or alkynyl, cycloalkyl, cycloalkenyl, or aryl-substituted alkyl; and $R^{12}$ is H, $C_{1-10}$ alkyl, $C_{2-10}$ alkenyl, $C_{2-10}$ alkynyl, aryl, aryl-$C_{1-10}$ alkyl, heteroaryl, or heteroaryl-$C_{1-10}$ alkyl. Cy has the same definition as stated above. Each of alkyl, alkenyl and alkynyl is optionally substituted with one to four substituents independently selected from $R^a$, and aryl and heteroaryl are optionally substituted with one to four substituents independently selected from $R^b$. $R^a$ and $R^b$ have been defined above. Note that $R^{11}$, $R^{12}$ and the carbon to which they are attached optionally form a 3–7 membered mono- or bicyclic ring containing 0–2 heteroatoms selected from N, O, and S.

In one embodiment, the compounds of this invention contain $R^1$ of formula (iii):

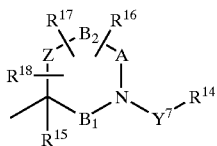

(iii)

wherein $R^{14}$ is $C_{1-10}$ alkyl, $C_{2-10}$ alkenyl, $C_{2-10}$ alkynyl, Cy, Cy—$C_{1-10}$ alkyl, Cy—$C_{2-10}$ alkenyl, or Cy—$C_{2-10}$ alkynyl; $R^{15}$ is H, $C_{1-10}$ alkyl, $C_{2-10}$ alkenyl, $C_{2-10}$ alkynyl, aryl, aryl-$C_{1-10}$ alkyl, heteroaryl, or heteroaryl-$C_{1-10}$ alkyl; each of $R^{16}$, $R^{17}$, and $R^{18}$, independently, is H, $C_{1-10}$ alkyl, $C_{2-10}$ alkenyl, $C_{2-10}$ alkynyl, Cy, Cy—$C_{1-10}$ alkyl, Cy—$C_{2-10}$ alkenyl, Cy—$C_{2-10}$ alkynyl, or a group selected from $R^a$. Cy has the same meaning as stated above (i.e., Cy represents cycloalkyl, heterocyclyl, aryl, or heteroaryl) is optionally substituted with one to four substituents independently selected from $R^b$ or one of the following groups: —$NR^c$—$C(O)NR^cSO_2R^d$, —$NR^cS(O)_mR^d$, —$OS(O)_2OR^c$, or —OP(O)(OR$^c$)$_2$. $R^b$ has been defined above. Two of $R^{16}$, $R^{17}$, and $R^{18}$, when attached to a common ring atom, together with the common ring atom optionally form a 5–7 membered saturated or unsaturated monocyclic ring containing zero to three heteroatoms selected from N, O, or S. Two of $R^{16}$, $R^{17}$, and $R^{18}$, when attached to two adjacent ring atoms, together with these two ring atoms optionally form a 5–7 membered saturated or unsaturated monocyclic ring containing zero to three heteroatoms selected from N, O, or S. The ring

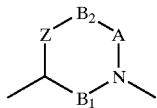

represents a 3–7 membered saturated or unsaturated heterocyclyl or heteroaryl wherein each of Z, A, B$_1$ and B$_2$, independently, is a bond, —C—, —C—C—, —C=C—, a heteroatom selected from the group consisting of N, O, and S, or —S(O)$_m$— (with m being 0, 1, or 2). $Y^7$ is —C(O)—, —C(O)O—, —C(O)NR$^c$—, —S(O)$_2$—, —P(O)(OR$^c$), or —C(O)—C(O)—. $R^c$ has the same meaning as stated above. Each of the alkyl, alkenyl and alkynyl is optionally substituted with one to four substituents lindependently selected from $R^a$, and each Cy is optionally substituted with one to four substituents independently selected from $R^b$. $R^a$ and $R^b$ have been defined above. In one embodiment, the ring

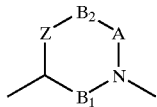

in formula (ii), supra, represents azetidine, pyrrole, pyrrolidine, imidazole, pyrazole, triazole, pyridine, piperidine, pyrazine, piperazine, pyrimidine, oxazole, thiazole, or morpholine. In one embodiment, the just-mentioned ring represents azetidine, pyrrole, pyrrolidine, imidazole, piperidine, or morpholine. In one embodiment, the just-mentioned ring represents pyrrolidine. In one embodiment, $R^{15}$ is H or $C_{1-5}$ alkyl. In one embodiment, each of $R^{16}$, $R^{17}$, and $R^{18}$, independently, is H, $C_{1-10}$ alkyl, Cy, —$OR^c$, -halogen, —$S(O)_mR^c$, —$NR^cR^d$, —$NR^c$—C(O)R$^d$, —$NR^c$—C(O)OR$^d$, —$NR^cC(O)NR^dR^e$, or oxo (each of $R^c$, $R^d$, $R^e$, and m have been defined above). In one embodiment, $Y^7$ is —O—C(O)—, —C(O)—O—, or —SO$_2$— (e.g., $Y^7$ is —SO$_2$—). In one embodiment, $R^{14}$ is Cy or Cy—$C_{1-5}$ alkyl (e.g., $R^{14}$ is phenyl).

In one embodiment, the compounds of this invention contain L' having 2–4 (e.g., 2 or 3) carbon chain atoms.

In one embodiment, L' is of formula (iv):

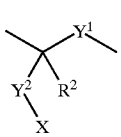

(iv)

wherein $Y^1$ is —C(O)—, —O—C(O)—, —C(O)—O—, —C(O)—NR$^c$—, —NR$^c$—C(O)—, —NR$^c$—C(O)—NR$^d$—, —NR$^c$C(O)—O—, —O—C(O)—NR$^c$—, —S(O)$_m$—, S(O)$_2$—NR$^c$—, —NR$^c$—S(O)$_2$—, —NR$^c$—C(NR$^m$)—, —O—, or —NR$^c$— (R$^c$, R$^d$, R$^m$, and m have been defined above); $R^2$ is H, $C_{1-10}$ alkyl, $C_{2-10}$ alkenyl, $C_{2-10}$ alkynyl, Cy, Cy—$C_{1-10}$ alkyl, Cy—$C_{1-10}$ alkenyl, or Cy—$C_{1-10}$ alkynyl; $Y^2$ is a bond or —C(R$^h$)(R$^i$)—, wherein each of $R^h$ and $R^i$, independently, is H, $C_{1-10}$ alkyl, $C_{2-10}$ alkenyl, $C_{2-10}$ alkynyl, aryl, aryl-$C_{1-10}$ alkyl, heteroaryl, or heteroaryl-$C_{1-10}$ alkyl, and $R^h$ and $R^i$ can be taken together with the carbon to which they are attached to form a 3–7 membered ring containing 0–2 heteroatoms selected from N, O and S; X is —C(O)OR$^c$, —P(O)(OR$^c$)(OR$^d$), —P(O)(R$^c$)(OR$^d$), —S(O)$_m$OR$^c$, —C(O)NR$^c$R$^j$, or -5-tetrazolyl. m have been defined above. Each of said alkyl, alkenyl and alkynyl is optionally substituted with one to four substituents independently selected from $R^a$; each of aryl and heteroaryl is optionally substituted with one to four substituents independently selected from $R^b$; and Cy is a cycloalkyl, heterocyclyl, aryl, or heteroaryl. $R^a$ and $R^b$ have been defined above. Note that when $Y^2$ is not a bond, X is —COOH, —COO—$C_{1-4}$ alkyl, —P(O)(OH)$_2$, —P(O)(OH)(O—$C_{1-4}$ alkyl), —P(O)($C_{1-4}$ alkyl)$_2$, —P(O)(OH)($C_{1-4}$ alkyl), —P(O)(O—$C_{1-4}$ alkyl)($C_{1-4}$ alkyl), —SO$_2$—$C_{1-4}$ alkyl, —CO—NH$_2$, —CO—NH($C_{1-4}$ alkyl), —CO—N($C_{1-4}$ alkyl)$_2$, or -5-tetrazolyl. In one embodiment, $Y^1$ is —NR$^c$—C(O)—, —NR$^c$—, —NR$^c$—S(O)$_2$—, or —NR$^c$—C(NR$^m$)—. In one embodiment, $Y^1$ is —NR$^c$—C(O)— (e.g., —NH—CO— or —N($C_{1-4}$ alkyl)—CO—; with the carbonyl group attaching to $R^1$). In one embodiment, $R^2$ is H or $C_{1-5}$ alkyl. In one embodiment, $R^2$ is H. In one embodiment, Y is a bond or —C(R$^h$)(R$^h$)—, wherein each of $R^h$ and R$^i$, independently, is H or $C_{1-5}$ alkyl. In one embodiment, $Y^2$ is a bond or —CH$_2$—. In one embodiment, X is —C(O)OR$^c$ (e.g., —COOH or —COO—$C_{1-5}$ alkyl such as —COO—CH$_3$ or —COO—CH$_2$CH$_3$) or —C(O)NR$^c$R$^j$—. In one embodiment, $Y^1$ is —NR$^c$—C(O)— (e.g., —NH—CO—); $R^2$ is H or $C_{1-5}$ alkyl (e.g., H); $Y^2$ is a bond or —CH$_2$— (e.g., a bond); and X is —C(O)OR$^c$ where each $R^c$ is independently H or $C_{1-5}$ alkyl.

In one embodiment, the compounds of this invention contain L having 4–10 (e.g., 4–8 or 4–6) carbon chain atoms.

In one embodiment, L is of formula (v):

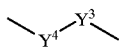

(v)

wherein $Y^3$ is a bond, $C_{1-10}$ alkyl, $C_{2-10}$ alkenyl, $C_{2-10}$ alkynyl, aryl, aryl-$C_{1-10}$ alkyl, heteroaryl, or heteroaryl-$C_{1-10}$ alkyl; and $Y^4$ is a bond, —C(O)—, —O—C(O)—, —C(O)—O—, —C(O)—$NR^c$—, —$NR^c$—C(O), —$NR^c$—C(O)—$NR^d$—, —$NR^c$—C(O)—O—, —O—C(O)—$NR^c$—, —S(O)$_m$—, —S(O)$_2$—$NR^c$—, —$NR^c$—S(O)$_2$—, —$NR^c$—C($NR^d$)—, —O—, or —$NR^c$— ($R^c$, $R^d$, and m have been defined above). Each of alkyl, alkenyl, and alkynyl is optionally containing (interrupted by or terminally attached to) one to four heteroatoms selected from N, O, S, and —S(O)$_m$—; and each of alkyl, alkenyl and alkynyl is optionally substituted with one to four substituents independently selected from $R^a$. Each of aryl and heteroaryl is optionally substituted with one to four substituents independently selected from $R^b$. $R^a$, $R^b$, $R^c$, $R^d$, and m have been defined above. Note that each of $Y^3$ and $Y^4$ is not a bond simultaneously. In one embodiment, $Y^3$ is a bond, $C_{1-5}$ alkyl, or $C_{1-5}$ alkenyl (e.g., $Y^3$ is a bond or $C_{1-5}$ alkyl); and $Y^4$ is a bond, —C(O)—$NR^c$, —C(O)—, —$NR^c$—, or —O—, where $R^c$ is H or $C_{1-5}$ alkyl (e.g., $Y^4$ is —C(O)—NH—).

In one embodiment, the compounds of this invention contain $R^3$ with the formula: $Z^3$—$L^b$—$Z^4$—, wherein $Z^3$ is Cy, Cy—$C_{1-10}$ alkyl, Cy—$C_{1-10}$ alkenyl, or Cy—$C_{1-10}$ alkynyl; $L^b$ is —C(O)—, —O—C(O)—, —C(O)—O—, —C(O)—$NR^c$—, —$NR^c$—C(O)—, —$NR^c$—C(O)—$NR^d$—, —$NR^c$—C(O)—O—, —O—C(O)—$NR^c$—, —S(O)$_m$—, —SO$_2$—$NR^c$—, —$NR^c$SO$_2$—, —O—, —$NR^c$—, or a bond ($R^c$, $R^d$, and m have been defined above); and $Z^4$ is cycloalkyl, cycloalkyl-$C_{1-10}$ alkyl, cycloalkenyl, cycloalkenyl-$C_{1-10}$ alkyl, aryl, aryl-$C_{1-10}$ alkyl, heterocyclyl, heterocyclyl-$C_{1-10}$ alkyl, heteroaryl, heteroaryl-$C_{1-10}$ alkyl or a bond; or $R^3$ is a moiety of formula (i):

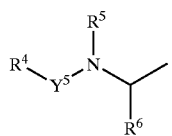

(i)

each of m, $R^c$, $R^d$ $R^4$, $R^5$, $R^6$, and $Y^5$ have been defined in claim 1. In one embodiment, $R^4$ is $Z^5$—$L^c$—$Z^6$—, wherein $Z^5$ is Cy, Cy—$C_{1-10}$ alkyl, Cy—$C_{1-10}$ alkenyl, or Cy—$C_{1-10}$ alkynyl; $L^c$ is —C(O)—, —O—C(O)—, —C(O)—O—, —C(O)—$NR^c$—, —$NR^c$—C(O)—, —$NR^c$—C(O)—$NR^d$—, —$NR^c$—C(O)—O, —O—C(O)—$NR^c$—, —S(O)$_m$—, —SO$_2$—$NR^c$—, —$NR^c$—SO$_2$—, —O—, —$NR^c$—, or a bond; and $Z^6$ is cycloalkyl, cycloalkyl-$C_{1-10}$ alkyl, cycloalkenyl, cycloalkenyl-$C_{1-10}$ alkyl, aryl, aryl-$C_{1-10}$ alkyl, heterocyclyl, heterocyclyl-$C_{1-10}$ alkyl, heteroaryl, heteroaryl-$C_{1-10}$ alkyl or a bond. $R^c$, $R^d$, m have been defined above. In one embodiment, each of $Z^3$ and $Z^5$, independently, is aryl, aryl-$C_{1-10}$ alkyl, aryl-$C_{1-10}$ alkenyl, aryl-$C_{1-10}$ alkynyl, heteroaryl, heteroaryl-$C_{1-10}$ alkyl, heteroaryl-$C_{1-10}$ alkenyl, or heteroaryl-$C_{1-10}$ alkynyl; each of $L^b$ and $L^c$, independently, is —C(O)—, —S(O)$_m$—, —O—C(O)—, —C(O)—O—, —C(O)—$NR^c$—, —$NR^c$—C(O)—, —$NR^c$—C(O)—$NR^d$—, —SO$_2$—$NR^c$—, —$NR^c$—SO$_2$—, —O—, —$NR^c$—, or a bond; and each of $Z^4$ and $Z^6$, independently, is aryl, aryl-$C_{1-10}$ alkyl, heterocyclyl, heterocyclyl-$C_{1-10}$ alkyl, heteroaryl, heteroaryl-$C_{1-10}$ alkyl, or a bond. In one embodiment, each of $Z^3$ and $Z^5$, independently, is aryl, aryl-$C_{1-10}$ alkyl, heteroaryl, or heteroaryl-$C_{1-10}$ alkyl; each of $L^b$ and $L^c$, independently, is —C(O)—, —SO$_2$—, —C(O)—$NR^c$—, —$NR^c$—C(O)—, or —$NR^c$—C(O)—$NR^d$—; where each of $R^c$ and $R^d$, independently, is H or $C_{1-5}$ alkyl; and each of $Z^4$ and $Z^6$, independently, is aryl, aryl-$C_{1-10}$ alkyl, heterocyclyl, heterocyclyl-$C_{1-10}$ alkyl, heteroaryl, heteroaryl-$C_{1-10}$ alkyl, or a bond. In one embodiment, each of $Z^3$ and $Z^5$, independently, is aryl (e.g., phenyl or naphthyl); each of $L^b$ and $L^c$, independently, is —$NR^c$—C(O)—$NR^d$— (e.g., —NH—CO—NH—, —N(methyl)-CO—NH—, or —NH—CO—N(methyl)-); and each of $Z^4$ and $Z^6$, independently, is aryl (e.g., phenyl or naphthyl). In one embodiment, $Y^5$ is —CO— or —O—CO— (e.g., —CO—). In one embodiment, $R^5$ is H or $C_{1-5}$ alkyl (e.g., H, methyl, or ethyl). In one embodiment, $R^6$ is an amino acid side chain selected from the group consisting of cyclohexylalanine, leucine, isoleucine, allo-isoleucine, tert-leucine, norleucine, phenylalanine, phenylglycine, alanine, norvaline, valine, and 2-aminobutyric acid. In one embodiment, $R^6$ is an amino acid side chain selected from the group consisting of leucine, isoleucine, allo-isoleucine, tert-leucine, norleucine, alanine, norvaline, valine, and 2-aminobutyric acid. In one embodiment, $R^6$ is the side chain of leucine or isoleucine.

In one embodiment, the compounds of formula (I) contain $R^1$ with the formula $Z^1$—$L^a$—$Z^2$—, wherein $Z^1$ is aryl (e.g., phenyl) optionally substituted with Cy, —CO—$R^d$, halogen, oxo, or aryl-substituted alkenyl; $L^a$ is —O—C(O)—, —C(O)—O—, —C(O)—$NR^c$—, —$NR^c$—C(O)—, or —SO$_2$— (e.g., —SO$_2$—); and $Z^2$ is a bond, heteroaryl, heterocyclyl (e.g., azetidine, pyrrole, pyrrolidine, imidazole, piperidine, or morpholine); L' with formula (iv), supra, wherein $Y^1$ is —$NR^c$—C(O)—, —$NR^c$—, —$NR^c$—S(O)$_2$—, or —$NR^c$—C($NR^d$)—; $R^2$ is H or $C_{1-5}$ alkyl; $Y^2$ is a bond or —C($R^h$)($R^i$)—; and X is —C(O)O$R^c$; where each of $R^c$, $R^h$, and $R^i$, independently, is H or $C_{1-5}$ alkyl (e.g., $Y^1$ is —NH—C(O)—; $R^2$ is H; $Y^2$ is a bond; and X is —C(O)OH); L with formula (v), supra, wherein $Y^3$ is a bond, $C_{1-5}$ alkyl, or $C_{1-5}$ alkenyl; and $Y^4$ is a bond, —C(O)—$NR^c$—, —C(O)—, —$NR^c$—, or —O—, where $R^c$ is H or $C_{1-5}$ alkyl (e.g., $Y^3$ is a bond or $C_{1-5}$ alkyl and $Y^4$ is —C(O)—NH—); and $R^3$ with the formula $Z^3$—$L^b$—$Z^4$— or formula (i), supra. When $R^3$ is of formula (i), $R^4$ is $Z^5$—$L^c$—$Z^6$—, wherein $Z^5$ is aryl, aryl-$C_{1-10}$ alkyl, aryl-$C_{1-10}$ alkenyl, aryl-$C_{1-10}$ alkenyl heteroaryl, heteroaryl-$C_{1-10}$ alkyl, heteroaryl-$C_{1-10}$ alkenyl, or heteroaryl-$C_{1-10}$ alkynyl; $L^c$ is —C(O)—, —S(O)$_m$—, —O—C(O)—, —C(O)—O—, —C(O)—$NR^c$—, —$NR^c$—C(O)—, —$NR^c$—C(O)—$NR^d$—, —SO$_2$—$NR^c$—, —$NR^c$—SO$_2$—, —O—, —$NR^c$—, or a bond, with $R^c$ and $R^d$, independently, being H or $C_{1-5}$ alkyl; and $Z^6$ is aryl, aryl-$C_{1-10}$ alkyl, heterocyclyl, heterocyclyl-$C_{1-10}$ alkyl, heteroaryl, heteroaryl-$C_{1-10}$ alkyl, or a bond. In one embodiment, $Z^5$ is aryl (e.g., phenyl or naphthyl); $L^c$ is —$NR^c$—C(O)—$NR^d$— (e.g., —NH—CO—NH— or —NH—CO—N(methyl)-); and $Z^6$ is aryl (e.g., phenyl or naphthyl). In one embodiment, $R^4$ is o-methylphenyl-ureido-phenyl-$CH_2$—. In one embodiment, $Y^5$ is —CO— or —O—CO— (e.g., —CO—). In one embodiment, $R^5$ is H or $C_{1-2}$ alkyl. In one embodiment, $R^6$ is an amino acid side chain selected from the group consisting of leucine, isoleucine, allo-isoleucine, tert-leucine, norleucine, alanine, norvaline, valine, and 2-aminobutyric acid (e.g., leucine or isoleucine).

In one embodiment, the compounds of formula (I) contain $R^1$ with formula (ii), supra, wherein $R^9$ is $C_{1-10}$ alkyl, $C_{2-10}$ alkenyl, $C_{2-10}$ alkynyl, Cy, Cy—$C_{1-10}$ alkyl, Cy—$C_{2-10}$ alkeny Cy—$C_{2-10}$ alkynyl (e.g., aryl or heteroaryl); each of $R^{10}$ and $R^{11}$, independently, is hydrogen, aryl, alkyl, alkenyl or alkynyl, cycloalkyl, cycloalkenyl, or aryl-substituted alkyl (e.g., H, alkyl, cycloalkyl, heterocyclyl, aryl, or heteroaryl); and $R^{12}$ is H, $C_{1-10}$ alkyl, $C_{2-10}$ alkenyl, $C_{2-10}$ alkynyl, aryl, aryl-$C_{1-10}$ alkyl, heteroaryl, or heteroaryl-$C_{1-10}$ alkyl (e.g., H, alkyl, alkenyl, alkynyl, heterocyclyl, or aryl). Cy has the same definition as stated above. Each of alkyl, alkenyl and alkynyl is optionally substituted with one to four substituents independently selected from $R^a$, and aryl and heteroaryl are optionally substituted with one to four substituents independently selected from $R^b$ (e.g., halogen). $R^a$ and $R^b$ have been defined above. Note that $R^{11}$, $R^{12}$ and the carbon to which they are attached optionally form a 3–7 membered mono- or bicyclic ring containing 0–2 heteroatoms selected from N, O, and S. In this embodiment, the compounds also contain L' with formula (iv), supra, wherein $Y^1$ is —$NR^c$—C(O)—, —$NR^c$—, —$NR^c$—S(O)$_2$—, or —$NR^c$—C($NR^d$)—; $R^2$ is H or $C_{1-5}$ alkyl; $Y^2$ is a bond or —C($R^h$)($R^i$)—; and X is —C(O)O$R^c$; where each of $R^c$, $R^h$, and $R^i$, independently, is H or $C_{1-5}$ alkyl (e.g., $Y^1$ is —NH—C(O)—; $R^2$ is H; $Y^2$ is a bond; and X is —C(O)OH); and L with formula (v), supra, wherein $Y^3$ is a bond, $C_{1-5}$ alkyl, or $C_{1-5}$ alkenyl; and $Y^4$ is a bond, —C(O)—$NR^c$—, —C(O)—, —$NR^c$—, or —O—, where $R^c$ is H or $C_{1-5}$ alkyl (e.g., $Y^3$ is a bond or $C_{1-5}$ alkyl and $Y^4$ is —C(O)—NH—); and $R^3$ with the formula $Z^3$—$L^b$—$Z^4$— or formula (i), supra. When $R^3$ is of formula (i), $R^4$ is $Z^5$—$L^c$—$Z^6$—, wherein $Z^5$ is aryl, aryl-$C_{1-10}$ alkyl, aryl-$C_{1-10}$ alkenyl, aryl-$C_{1-10}$ alkynyl, heteroaryl, heteroaryl-$C_{1-10}$ alkyl, heteroaryl-$C_{1-10}$ alkenyl, or heteroaryl-$C_{1-10}$ alkynyl; $L^c$ is —C(O)—, —S(O)$_m$—, —O—C(O)—, —C(O)—O—, —C(O)—$NR^c$—, —$NR^c$—C(O)—, —$NR^c$—C(O)—$NR^d$—, —SO$_2$—$NR^c$—, —$NR^c$—SO$_2$—, —O—, —$NR^c$—, or a bond, with $R^c$ and $R^d$, independently, being H or $C_{1-5}$ alkyl; and $Z^6$ is aryl, aryl-$C_{1-10}$ alkyl, heterocyclyl, heterocyclyl-$C_{1-10}$ alkyl, heteroaryl, heteroaryl-$C_{1-10}$ alkyl, or a bond. In one embodiment, $Z^5$ is aryl (e.g., phenyl or naphthyl); $L^c$ is —$NR^c$—C(O)—$NR^d$— (e.g., —NH—CO—NH— or —NH—CO—N(methyl)-); and $Z^6$ is aryl (e.g., phenyl or naphthyl). In one embodiment, $R^4$ is o-methylphenyl-ureido-phenyl-CH$_2$—. In one embodiment, $Y^5$ is —CO— or —O—CO— (e.g., —CO—). In one embodiment, $R^5$ is H or $C_{1-2}$ alkyl. In one embodiment, $R^6$ is an amino acid side chain selected from the group consisting of leucine, isoleucine, allo-isoleucine, tert-leucine, norleucine, alanine, norvaline, valine, and 2-aminobutyric acid (e.g., leucine or isoleucine).

In one embodiment, the compounds of formula (I) contain $R^1$ with formula (iii), supra, wherein $R^{14}$ is Cy or Cy—$C_{1-5}$ alkyl (e.g., $R^{14}$ is phenyl); $R^{15}$ is H or $C_{1-5}$ alkyl; each of $R^{16}$, $R^{17}$, and $R^{18}$, independently, is H, $C_{1-10}$ alkyl, Cy, —O$R^c$, -halogen, —S(O)$_m R^c$, —$NR^c R^d$, —$NR^c$C(O)$R^d$, —$NR^c$—C(O)O$R^d$, —$NR^c$C(O)$NR^d R^e$, or oxo (two of $R^{16}$, $R^{17}$, and $R^{18}$, when attached to two adjacent ring atoms, together with these two ring atoms optionally form a 5–7 membered cycloalkyl, heterocyclyl, aryl or heteroaryl); the ring

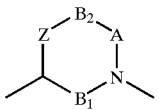

represents azetidine, pyrrole, pyrrolidine, imidazole, piperidine, or morpholine (e.g., pyrrolidine); $Y^7$ is —O—C(O)—, —C(O)—O—, or —SO$_2$— (e.g., $Y^7$ is —SO$_2$—). The compounds also contain L' with formula (iv), supra, wherein $Y^1$ is —$NR^c$—CC(O)—, —$NR^c$—, —$NR^c$—CS(O)$_2$—, or —$NR^c$—C($NR^d$)—; $R^2$ is H or $C_{1-5}$ alkyl; $Y^2$ is a bond or —C($R^h$)($R^i$)—; and X is —C(O)O$R^c$; where each of $R^c$, $R^h$, and $R^i$, independently, is H or $C_{1-5}$ alkyl (e.g., $Y^1$ is —NH—C(O)—; $R^2$ is H; $Y^2$ is a bond; and X is —C(O)OH); and L with formula (v), supra, wherein $Y^3$ is a bond, $C_{1-5}$ alkyl, or $C_{1-5}$ alkenyl; and $Y^4$ is a bond, —C(O)—$NR^c$, —C(O)—, —$NR^c$—, or —O—, where $R^c$ is H or $C_{1-5}$ alkyl (e.g., $Y^3$ is a bond or $C_{1-5}$ alkyl and $Y^4$ is —C(O)—NH—); and $R^3$ with the formula $Z^3$—$L^b$—$Z^4$— or formula (i), supra. When $R^3$ is of formula (i), $R^4$ is $Z^5$—$L^c$—$Z^6$—, wherein $Z^5$ is aryl, aryl-$C_{1-10}$ alkyl, aryl-$C_{1-10}$ alkenyl, aryl-$C_{1-10}$ alkynyl, heteroaryl, heteroaryl-$C_{1-10}$ alkyl, heteroaryl-$C_{1-10}$ alkenyl, or heteroaryl-$C_{1-10}$ alkynyl; $L^c$ is —C(O)—, —S(O)$_m$—, —O—C(O)—, —C(O)—O—, —C(O)—$NR^c$—, —$NR^c$—C(O)—, —$NR^c$—C(O)—$NR^d$—, —SO$_2$—$NR^c$—, —$NR^c$—SO$_2$—, —O—, —$NR^c$—, or a bond, with $R^c$ and $R^d$, independently, being H or $C_{1-5}$ alkyl; and $Z^6$ is aryl, aryl-$C_{1-10}$ alkyl, heterocyclyl, heterocyclyl-$C_{1-10}$ alkyl, heteroaryl, heteroaryl-$C_{1-10}$ alkyl, or a bond. In one embodiment, $Z^5$ is aryl (e.g., phenyl or naphthyl); $L^c$ is —$NR^c$—C(O)—$NR^d$— (e.g., —NH—CO—NH— or —NH—CO—N(methyl)-); and $Z^6$ is aryl (e.g., phenyl or naphthyl). In one embodiment, $R^4$ is o-methylphenyl-ureido-phenyl-CH$_2$—. In one embodiment, $Y^5$ is —CO— or —O—CO— (e.g., —CO—). In one embodiment, $R^5$ is H or $C_{1-2}$ alkyl. In one embodiment, $R^6$ is an amino acid side chain selected from the group consisting of leucine, isoleucine, allo-isoleucine, tert-leucine, norleucine, alanine, norvaline, valine, and 2-aminobutyric acid (e.g., leucine or isoleucine).

In one embodiment, the compounds of the invention are of formula (I) wherein $R^1$ is aryl or heterocyclyl-SO$_2$-aryl (e.g., pyrrolidine-SO$_2$-phenyl optionally substituted with alkyl or halo such as chloro, bromo, or iodo); L' is of formula (iv), supra, wherein $Y^1$ is —NH—CO—, —NH—, or —NH—C($NR^m$)—NH—, $R^2$ is H, $Y^2$ is a bond or —CH$_2$—, and X is COOH; L is of formula (v), supra, wherein $Y^3$ is —(CH$_2$)$_{0-5}$—, and $Y^4$ is —CO—NH—; and $R^3$ is o-methylphenyl-ureido-phenyl-CH$_2$— or of formula (i), supra, wherein $R^4$ is o-methylphenyl-ureido-phenyl-CH$_2$—, $Y^5$ is —CO— or —O—CO— (e.g., —CO—), $R^5$ is H or methyl, and $R^6$ is the side chain of leucine or isoleucine.

In one embodiment, the compounds of the invention contain L' and L as linker moiety, preferably composed of a chain containing C, O, S, or N atoms which link $R^1$ and $R^3$ and allow both $R^1$ and $R^3$ to interact, preferably bind, the VLA-4 molecule.

In one embodiment, the compounds of the invention have two terminally-located moieties of the formula $Z^\alpha$—$L^\alpha$—$Z^\beta$—. Each of $Z^\alpha$ and $Z^\beta$, independently, is an optionally substituted Cy, and $L^\alpha$ is a bond, or a linker moiety connecting $Z^\alpha$ and $Z^\beta$ and can contain —C(O)—, —O—C(O)—, —C(O)—O—, —C(O)—$NR^c$—, —$NR^c$—C(O)—, —$NR^c$—C(O)—$NR^d$—, —$NR^c$—C(O)—O—, —O—C (O)—NR$^c$—, —S(O)$_m$—, —S(O)$_2$—NR$^c$—, —NR$^c$—S(O)$_2$—, —NR$^c$—C(NR$^d$)—, —O—, or —NR$^c$—. By "terminally-located" is meant that the moiety is monovalently attached to the rest of the molecule.

In one embodiment, the compounds of the invention have an IC$_{50}$ of 5 nM or below, 2 nM or below, 1 nM or below, or 0.5 nM or below. IC$_{50}$ values can be determined by binding assays as described below or other known conventional methods. In one embodiment, the compounds of the invention have a % bound to the Mn activated form of VLA-4 molecules of 50% or higher, 75% or higher, 90% or higher, or 95% or higher. In one embodiment, the compounds of the invention have a % bound to the Ca/Mg activated form of VLA-4 molecules of 50% or higher, 75% or higher, 90% or higher, or 95% or higher. % bound to the VLA-4 molecules can be determined by biological assays as described below.

In one embodiment, the compounds of this invention are of formula (II):

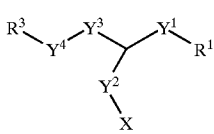

(II)

wherein each of R$^1$, Y$^1$, Y$^2$, X, Y$^3$, Y$^4$, and R$^3$ have been defined above.

In one embodiment, the compounds of this invention is of formula (III):

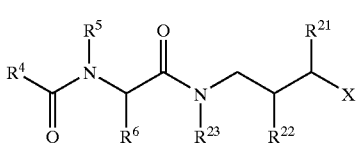

(III)

Each of R$^{21}$ and R$^{22}$, independently, is Cy, —OR$^c$, —NO$_2$, -halogen, —S(O)$_m$R$^c$, —SR$^c$, —S(O)$_2$OR$^c$, —S(O)$_2$NR$^c$R$^d$, —NR$^c$R$^d$, —O(CR$^e$R$^f$)$_n$NR$^c$R$^d$, —C(O)R$^c$, —CO$_2$R$^c$, —CO$_2$(CR$^e$R$^f$)$_n$CONR$^c$R$^d$, —OC(O)R$^c$, —CN, —C(O)NR$^c$R$^d$, —NR$^c$C(O)R$^d$, —OC(O)NR$^c$R$^d$, —NR$^c$C(O)OR$^d$, —R$^c$C(O)NR$^d$R$^e$, —CR$^c$(NOR$^d$), —CF$_3$, —OCF$_3$, oxo, C$_{1-10}$ alkyl, C$_{2-10}$ alkenyl, C$_{2-10}$ alkynyl, aryl-C$_{1-10}$ alkyl, or heteroaryl-C$_{1-10}$ alkyl; wherein each of alkyl, alkenyl, alkynyl, aryl, heteroaryl assignable to R$^{21}$ or R$^{22}$ is optionally substituted with a group independently selected from R$^g$. R$^{23}$ is H, C$_{1-10}$ alkyl, C$_{2-10}$ alkenyl, C$_{2-10}$ alkynyl, aryl, aryl-C$_{1-10}$ alkyl, heteroaryl, or heteroaryl-C$_{1-10}$ alkyl; wherein each of alkyl, alkenyl and alkynyl assignable to R$^{23}$ is optionally substituted with one to four substituents independently selected from R$^a$, and aryl and heteroaryl are optionally substituted with one to four substituents independently selected from R$^b$. R$^a$, R$^b$ and R$^g$ have been defined above.

In one embodiment, the compounds of this invention are of formula (IV):

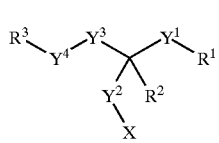

(IV)

wherein each of R$^1$, Y$^1$, R$^2$, Y$^2$, X, Y$^3$, Y$^4$, and R$^3$ have been defined above.

In one embodiment, the compounds of this invention are of formula (V):

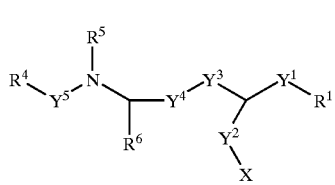

(V)

wherein each of R$^1$, Y$^1$, Y$^2$, X, Y$^3$, Y$^4$, R$^6$, R$^5$, Y$^5$ and R$^4$ have been defined above.

In one embodiment, the compounds of this invention are of formula (VI):

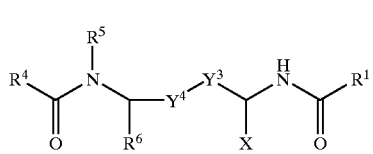

(VI)

wherein each of R$^1$, X, Y$^3$, Y$^4$, R$^6$, R$^5$, and R$^4$ have been defined above.

In one embodiment, the compounds of this invention are of formula (VII):

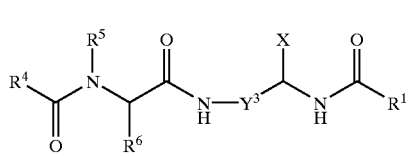

(VII)

wherein each of R$^1$, X, Y$^3$, R$^6$, R$^5$, and R$^4$ have been defined above.

Set forth below are some examples of a compound of this invention. For convenience, the nitrogen atom and the carbon atom in the column "N(R$^5$)—CH(R$^6$)" represents the α-nitrogen and the α-carbon atoms of the amino acid as indicated. For example, an entry "Leu" indicates that R$^5$ is H and R$^6$ is isobutyl.

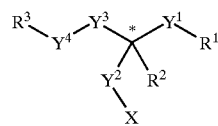

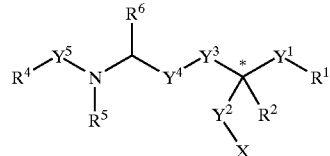

| CPD # | R3/R4 | Y5 | N(R5)CHR6 | Y4 |
|---|---|---|---|---|
| 5192 | oMePUPCH2 | —C(O)— | N-Me-Leu | —C(O)NH— |
| 5241 | tBu | —OC(O)— | N-Me-Leu | —C(O)NH— |
| 5247 | 4-HO-C6H4-CH2CH2- | | —C(O)— | N-Me-Leu | —C(O)NH— |
| 5262 | CH3 | — | — | —C(O)NH— |
| 5283 | oMePUPCH2 | —C(O)— | Leu | —C(O)NH— |
| 5286 | CH3 | — | — | —C(O)NH— |
| 5292 | oMePUPCH2 | —C(O)— | N-Me-Leu | —C(O)NH— |
| 5310 | Bn | — | — | —OC(O)NH— |
| 5357 | Bn | — | — | —OC(O)NH— |
| 5358 | oMePUPCH2 | —C(O)— | Leu | —C(O)NH— |
| 5420 | CH3 | —C(O)— | N-Me-Leu | —C(O)NH— |
| 5430 | Bn | —C(O)— | N-Me-Leu | —C(O)NH— |
| 5450 | 2-methylquinolinyl | —C(O)— | Leu | —C(O)NH— |
| 5451 | 4-HO-C6H4-CH2CH2- | —C(O)— | Leu | —C(O)NH— |
| 5743 | 2-Cl-Bn | — | — | —OC(O)NH— |
| 5750 | Bn | —C(O)— | N-Me-Leu | —C(O)NH— |
| 5751 | 4-HO-C6H4-CH2CH2- | —C(O)— | N-Me-Leu | —C(O)NH— |
| 5752 | CH3 | — | — | —C(O)NH— |
| 5788 | CH3 | — | — | —C(O)NH— |
| 5800 | CH3 | —C(O)— | Leu | —C(O)NH— |
| 5801 | 4-HO-C6H4-CH2CH2- | — | — | —C(O)NH— |
| 5803 | oMePUPCH2 | — | — | —C(O)NH— |
| 6655 | 2-methylquinolinyl | — | — | —C(O)NH— |
| 6668 | 2-methylquinolinyl | —C(O)— | N-Me-Leu | —C(O)NH— |

-continued

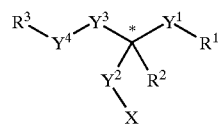

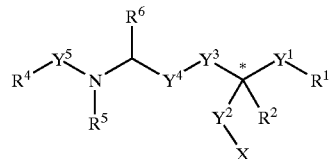

| | | | | |
|---|---|---|---|---|
| 6669 | (quinoline) | | —C(O)— | Pro | —C(O)NH— |
| 6670 | (quinoline) | | —C(O)— | MetO2 | —C(O)NH— |
| 6671 | (quinoline) | | —C(O)— | Leu | —C(O)NH— |
| 6696 | oMePUPCH2 | —C(O)— | Pro | —C(O)NH— |
| 6697 | oMePUPCH2 | —C(O)— | Pro | —C(O)NH— |
| 6714 | oMePUPCH2 | —C(O)— | N-Me-Leu | —C(O)NH— |
| 6715 | (benzofuranone) | —C(O)— | Pro | —C(O)NH— |
| 6716 | (benzofuranone) | —C(O)— | Leu | —C(O)NH— |
| 7080 | oMePUPCH2 | —C(O)— | N-Me-Leu | —C(O)NH— |
| 7081 | (benzofuranone) | — | — | —C(O)NH— |
| 7083 | oMePUPCH2 | — | — | —CO— |
| 7092 | oMePUPCH2 | —C(O)— | N-Me-Leu | —C(O)NH— |
| 7093 | oMePUPCH2 | —C(O)— | N-Me-Leu | —C(O)NH— |
| 7106 | oMePUPCH2 | —C(O)— | Dansyl-Lys | —C(O)NH— |
| 7109 | oMePUPCH2 | —C(O)— | N-Me-Leu | —C(O)NH— |
| 7111 | (indole-ethylphenyl amide) | — | — | —C(O)NH— |
| 7116 | oMePUPCH2 | —C(O)— | N-Me-Leu | —C(O)NH— |

-continued
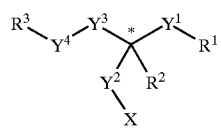
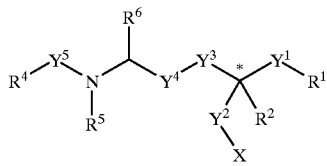
| | | | | |
|---|---|---|---|---|
| 7117 | (4,5,6,7-tetrahydro-3-methylbenzofuran-4-one) | — | — | —C(O)NH— |
| 7119 | oMePUPCH2 | — | — | —C(O)NH— |
| 7147 | (4-(phenylethynyl)phenyl-ethyl) | — | — | —C(O)NH— |
| 7148 | (2-methylquinoline) | — | — | —C(O)NH— |
| 7150 | 2-Cl-Bn | — | — | —OC(O)NH— |
| 7155 | oMePUPCH2 | — | — | —C(O)NH— |
| 7156 | oMePUPCH2 | — | — | —C(O)NH— |
| 7157 | (4,5,6,7-tetrahydro-3-methylbenzofuran-4-one) | — | — | —C(O)NH— |
| 7158 | CH3 | — | — | —C(O)NH— |
| 7168 | Bn | —C(O)— | N-Me-Leu | —C(O)NH— |
| 7171 | (4,5,6,7-tetrahydro-3-methylbenzofuran-4-one) | —C(O)— | N-Me-Leu | —C(O)NH— |
| 7172 | (4,5,6,7-tetrahydro-3-methylbenzofuran-4-one) | —C(O)— | Pro | —C(O)NH— |

-continued
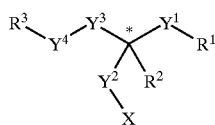
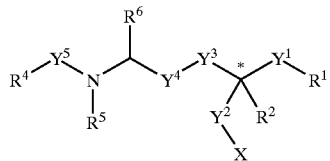
| | | | | | |
|---|---|---|---|---|---|
| 7175 | ![structure] | | —C(O)— | MetO2 | —C(O)NH— |
| 7177 | ![structure] | | —C(O)— | Leu | —C(O)NH— |
| 7181 | oMePUPCH2 | | —C(O)— | N-Me-Leu | —C(O)NH— |
| 7200 | oMePUPCH2 | | —C(O)— | N-Me-Leu | —C(O)NH— |
| 7231 | H | | — | — | —NH— |
| 7233 | ![structure] | | — | — | —NH— |
| 7234 | oMePUPCH2 | | —C(O)— | Leu | —NH— |
| 7235 | ![structure] | | — | — | —C(O)NH— |
| 7236 | ![structure] | | — | — | —C(O)NH— |
| 7241 | oMePUPCH2 | | — | — | —C(O)NH— |
| 7255 | Bn | | —C(O)— | Pro | —C(O)NH— |
| 7256 | oMePUPCH2 | | —C(O)— | Pro | —C(O)NH— |
| 7257 | Bn | | —C(O)— | Leu | —C(O)NH— |
| 7328 | oMePUPCH2 | | —C(O)— | N-Me-Leu | —C(O)NH— |
| 7375 | Bn | | —C(O)— | Leu | —C(O)NH— |
| 7398 | oMePUPCH2 | | —C(O)— | N-Me-Leu | —C(O)NH— |
| 7399 | oMePUPCH2 | | —C(O)— | Gly | —C(O)NH— |

-continued

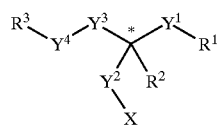

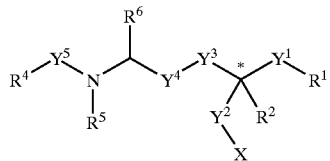

| | | | | |
|---|---|---|---|---|
| 7514 | (difluoroethylphenyl) | —C(O)— | Leu | —C(O)NH— |
| 7515 | (difluoroethylphenyl) | —C(O)— | Pro | —C(O)NH— |
| 7516 | (difluoroethylphenyl) | —C(O)— | Leu | —C(O)NH— |
| 7517 | (difluoroethylphenyl) | —C(O)— | Pro | —C(O)NH— |
| 7528 | (difluoroethylphenyl) | —C(O)— | Leu | —C(O)NH— |
| 7530 | (difluoroethylphenyl) | —C(O)— | Pro | —C(O)NH— |
| 7552 | oMePUPCH2 | —C(O)— | αN-Me-CBz-Lys- | —C(O)NH— |
| 7578 | oMePUPCH2 | —C(O)— | N-Me-Gly | —C(O)NH— |
| 7662 | oMePUPCH2 | —C(O)— | N-Me-Leu | —C(O)NH— |
| 7788 | oMePUPCH2 | — | — | —C(O)NH— |
| 7796 | oMePUPCH2 | —C(O)— | N-Me-Leu | —C(O)NH— |
| 7855 | oMePUPCH2 | — | — | —C(O)NH— |
| 7856 | (methyltetrahydrobenzofuranone) | — | — | —C(O)NH— |

-continued
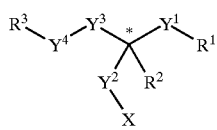
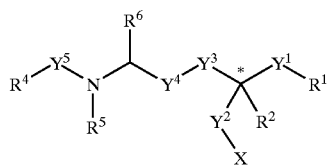
| | | | | |
|---|---|---|---|---|
| 7857 | ![4-hydroxyphenethyl] | — | — | —C(O)NH— |
| 8066 | CH3 | — | — | —C(O)NH— |
| 8067 | Bn | — | — | —C(O)NH— |
| 8122 | oMePUPCH2 | — | — | —C(O)NH— |
| 8123 | ![3-methyl-6,7-dihydrobenzofuran-4(5H)-one] | — | — | —C(O)NH— |
| 8147 | ![cumyl/2-phenylpropan-2-yl] | — | — | —C(O)NH— |
| 8205 | oMePUPCH2 | — | — | —C(O)NH— |
| 8208 | oMePUPCH2 | — | — | —C(O)NH— |
| 8209 | oMePUPCH2 | — | — | —C(O)NH— |
| 8210 | ![(2S)-1-(3,5-dichlorophenylsulfonyl)-2-methylpyrrolidine] | — | — | —C(O)NH— |
| 8211 | ![(2S)-1-(3,5-dichlorophenylsulfonyl)-2-methylpyrrolidine] | — | — | —C(O)NH— |

-continued

| | | | | |
|---|---|---|---|---|
| 8212 | [3,5-dichlorophenylsulfonyl-2-methylpyrrolidine structure] | — | — | —C(O)NH— |
| 8221 | oMePUPCH2 | —C(O)— | N-Me-Leu | —C(O)NH— |
| 8290 | oMePUPCH2 | —C(O)— | N-Me-Leu | —C(O)NH— |
| 8291 | oMePUPCH2 | —C(O)— | N-Me-Leu | —C(O)NH— |
| 8294 | oMePUPCH2 | —C(O)— | N-Me-Leu | —C(O)NH— |
| 8295 | oMePUPCH2 | —C(O)— | N-Me-Leu | —C(O)NH— |
| 8304 | oMePUPCH2 | — | — | —C(O)NH— |
| 8308 | oMePUPCH2 | —C(O)— | N-Me-Leu | —C(O)NH— |
| 8309 | oMePUPCH2 | —C(O)— | N-Me-Leu | —C(O)NH— |
| 8341 | oMePUPCH2 | —C(O)— | N-Me-Leu | —C(O)NH— |
| 8342 | oMePUPCH2 | —C(O)— | N-Me-Leu | —C(O)NH— |
| 8343 | oMePUPCH2 | —C(O)— | N-Me-Leu | —C(O)NH— |
| 8345 | oMePUPCH2 | — | — | —C(O)NH— |
| 8348 | oMePUPCH2 | —C(O)— | D-N-Me-Leu | —C(O)NH— |
| 8349 | oMePUPCH2 | —C(O)— | D-N-Me-Leu | —C(O)NH— |
| 8352 | oMePUPCH2 | — | — | —C(O)NH— |
| 8354 | 4-oMePUP | — | — | —O— |
| 8355 | oMePUPCH2 | — | — | —C(O)NH— |
| 8367 | oMePUPCH2 | —C(O)— | D-N-Me-Leu | —C(O)NH— |
| 8368 | oMePUPCH2 | —C(O)— | D-N-Me-Leu | —C(O)NH— |
| 8399 | [1-(2-methylphenyl)-3-(4-pentylphenyl)urea structure] | — | — | —C(O)NH— |
| 8446 | oMePUPCH2 | — | — | —C(O)NH— |
| 8449 | oMePUPCH2 | — | — | —C(O)NH— |
| 8450 | Bn | — | — | —C(O)NH— |
| 8451 | [α,α-difluoro-α-methylbenzyl structure] | —C(O)— | Pro | —C(O)NH— |
| 8452 | [3-methyl-6,7-dihydrobenzofuran-4(5H)-one structure] | — | — | —C(O)NH— |
| 8453 | oMePUPCH2 | — | — | —C(O)NH— |

-continued
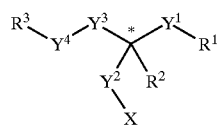
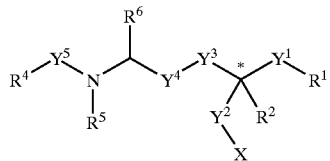
| | | | | |
|---|---|---|---|---|
| 8455 | [F,F-phenylethyl] | —C(O)— | Pro | —C(O)NH— |
| 8456 | [3-methyl-6,7-dihydrobenzofuran-4(5H)-one] | — | — | —C(O)NH— |
| 8457 | [F,F-phenylethyl] | —C(O)— | Pro | —C(O)NH— |
| 8458 | oMePUPCH2 | — | — | —C(O)NH— |
| 8459 | Bn | — | — | —C(O)NH— |
| 8460 | [F,F-phenylethyl] | —C(O)— | Pro | —C(O)NH— |
| 8461 | [3-methyl-6,7-dihydrobenzofuran-4(5H)-one] | — | — | —C(O)NH— |
| 8462 | oMePUPCH2 | — | — | —C(O)NH— |
| 8463 | Bn | — | — | —C(O)NH— |
| 8464 | [F,F-phenylethyl] | —C(O)— | Pro | —C(O)NH— |
| 8465 | [F,F-phenylethyl] | —C(O)— | Pro | —C(O)NH— |

-continued
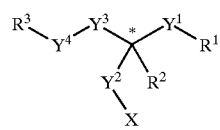
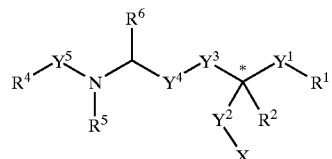
| | | | | | |
|---|---|---|---|---|---|
| 8466 | 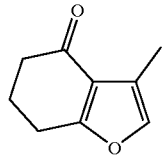 | | — | — | —C(O)NH— |
| 8469 | oMePUPCH2 | | —C(O)— | Leu | —C(O)NH— |
| 8485 | 2-oMePUP | | — | — | —O— |
| 8488 | oMePUPCH2 | | — | — | —C(O)NH— |
| 8491 | oMePUPCH2 | | —C(O)— | Leu | —C(O)NH— |
| 8493 | oMePUPCH2 | | —C(O)— | N-Me-Leu | —C(O)NH— |
| 8494 | oMePUPCH2 | | —C(O)— | D-N-Me-Leu | —C(O)NH— |
| 8513 | 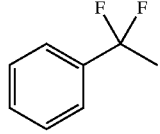 | | — | — | —C(O)NH— |
| 8514 | 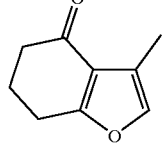 | | — | — | —C(O)NH— |
| 8515 | 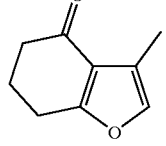 | | — | — | —C(O)NH— |
| 8516 | 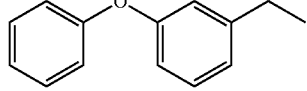 | | — | — | —C(O)NH— |
| 8519 | 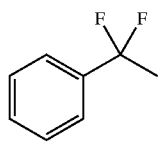 | | — | — | —C(O)NH— |
| 8520 | 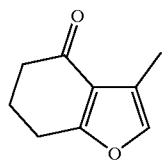 | | — | — | —C(O)NH— |
| 8528 | oMePUPCH2 | | —C(O)— | N-Me-Leu | —C(O)NH— |

-continued

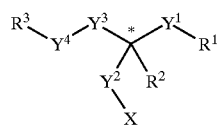

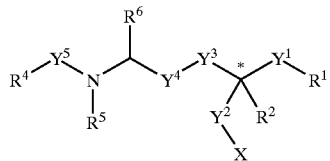

| | | | | |
|---|---|---|---|---|
| 8552 | [thiazole-pyridine structure] | —C(O)— | Leu | —C(O)NH— |
| 8553 | [benzofuranone structure] | —C(O)— | Leu | —C(O)NH— |
| 8554 | [benzimidazole structure] | —C(O)— | Leu | —C(O)NH— |
| 8555 | oMePUPCH2 | —C(O)— | N-Me-Leu | —C(O)NH— |
| 8557 | oMePUP(CH2)2 | — | — | —C(O)NH— |
| 8558 | oMePUP(CH2)2 | —C(O)— | Leu | —C(O)NH— |
| 8559 | oMePUP(CH2)3 | —C(O)— | Leu | —C(O)NH— |
| 8566 | [diphenyl-thiazole structure] | —C(O)— | Leu | —C(O)NH— |
| 8567 | [phenyl-methylthiazole structure] | —C(O)— | Leu | —C(O)NH— |
| 8571 | oMePUPCH2 | —C(O)— | N-Me-Leu | —C(O)NH— |
| 8582 | oMePUPCH2 | —C(O)— | N-Me-Leu | —C(O)NH— |
| 8583 | oMePUPCH2 | —C(O)— | N-Me-Leu | —C(O)NH— |
| 8585 | [indole-carboxamide structure] | —C(O)— | Leu | —C(O)NH— |
| 8586 | oMePUPCH2 | —C(O)— | N-Me-Leu | —C(O)NH— |
| 8606 | Bn | — | — | —C(O)NH— |
| 8607 | oMePUPCH2 | — | — | —C(O)NH— |

-continued

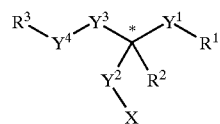

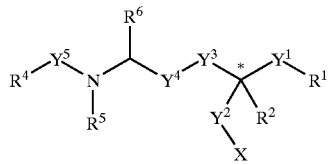

| | | | | |
|---|---|---|---|---|
| 8620 |  | — | — | —C(O)NH— |
| 8621 | oMePUPCH2 | —C(O)— | Pro | —C(O)NH— |
| 8628 | oMePUPCH2 | —C(O)— | N-Me-Leu | —C(O)NH— |
| 8629 | oMePUPCH2 | — | — | —C(O)NH— |
| 8630 | oMePUPCH2 | —C(O)— | Pro | —C(O)NH— |
| 8632 | Bz | —C(O)— | Pro | —C(O)NH— |
| 8637 |  | — | — | —C(O)NH— |
| 8638 | Bn | —C(O)— | Leu | —C(O)NH— |
| 8639 | Bn | —C(O)— | Leu | —C(O)NH— |
| 8642 | oMePUPCH2 | —C(O)— | N-Me-Leu | —C(O)NH— |
| 8643 | oMePUPCH2 | —C(O)— | Asp | —C(O)NH— |
| 8646 | oMePUPCH2 | — | — | —C(O)NH— |
| 8656 | oMePUPCH2 | — | — | —C(O)NH— |
| 8674 | oMePUPCH2 | —C(O)— | N-Me-Leu | —C(O)NH— |
| 8684 | oMePUPCH2 | — | — | —C(O)NH— |
| 8685 | oMePUPCH2 | —C(O)— | N-Me-Leu | —C(O)NH— |
| 8689 | oMePUPCH2 | —C(O)— | N-Me-Leu | —C(O)NH— |
| 8690 | oMePUPCH2 | —C(O)— | N-Me-Leu | —C(O)NH— |
| 8698 | oMePUPCH2 | —C(O)— | N-Me-Glu | —C(O)NH— |
| 8723 | oMePUPCH2 | —C(O)— | N-Me-Leu | —C(O)NH— |
| 8746 | oMePUPCH2 | —C(O)— | N-Me-Leu | —C(O)NH— |
| 8749 | oMePUPCH2 | —C(O)— | N-Me-Leu | —C(O)NH— |
| 8758 | oMePUPCH2 | —C(O)— | N-Me-Leu | —C(O)NH— |
| 8796 | oMePUPCH2 | —C(O)— | N-Me-Leu | —C(O)NH— |
| 8797 | oMePUPCH2 | —C(O)— | N-Me-Leu | —C(O)NH— |
| 8809 | oMePUPCH2 | —C(O)— | N-Me-Leu | —C(O)NH— |
| 8905 | oMePUPCH2 | —C(O)— | Leu | —C(O)NH— |
| 8906 | oMePUPCH2 | —C(O)— | Pro | —C(O)NH— |
| 8929 | oMePUPCH2 | —C(O)— | N-Me-Leu | —C(O)NH— |
| 9120 | oMePUPCH2 | —C(O)— | N-Me-Leu | —C(O)NH— |
| 9140 | oMePUPCH2 | —C(O)— | N-Me-Leu | —C(O)NH— |
| 9169 | oMePUPCH2 | —C(O)— | N-Me-Leu | —C(O)NH— |
| 9170 | oMePUPCH2 | —C(O)— | N-Me-Leu | —C(O)NH— |
| 9171 | oMePUPCH2 | —C(O)— | N-Me-Leu | —C(O)NH— |
| 9182 | oMePUPCH2 | —C(O)— | N-Me-Leu | —C(O)NH— |
| 9227 | oMePUPCH2 | —C(O)— | N-Me-Leu | —C(O)NH— |
| 9232 | oMePUPCH2 | — | — | —C(O)NH— |
| 9233 | oMePUPCH2 | —C(O)— | Leu | —C(O)NH— |
| 9234 | oMePUPCH2 | — | — | —C(O)NH— |
| 9235 | oMePUPCH2 | —C(O)— | Leu | —C(O)NH— |
| 9236 | oMePUPCH2 | — | — | —C(O)NH— |
| 9237 | oMePUPCH2 | —C(O)— | Leu | —C(O)NH— |
| 9238 | oMePUPCH2 | — | — | —C(O)NH— |
| 9239 | oMePUPCH2 | —C(O)— | Leu | —C(O)NH— |
| 9264 | oMePUPCH2 | —C(O)— | N-Me-Leu | —C(O)NH— |
| 9270 | oMePUPCH2 | — | — | —C(O)— |
| 9271 | oMePUPCH2 | —C(O)— | Leu | —C(O)— |
| 9273 | oMePUPCH2 | —C(O)— | Leu | —C(O)— |

-continued

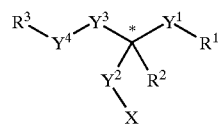

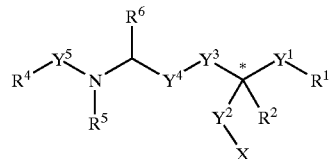

| CPD# | | | | |
|------|------|------|------|------|
| 9274 | oMePUPCH2 | — | — | —C(O)— |
| 9275 | oMePUPCH2 | —C(O)— | Leu | —C(O)— |
| 9276 | oMePUPCH2 | — | — | —C(O)— |
| 9277 | oMePUPCH2 | —C(O)— | Leu | —C(O)— |
| 9315 | oMePUPCH2 | —C(O)— | N-Me-Leu | —C(O)NH— |
| 9418 | oMePUPCH2 | —C(O)— | N-Me-Leu | —C(O)NH— |
| 9437 | oMePUPCH2 | —C(O)— | N-Me-Leu | —C(O)NH— |
| 9621 | ![indole-carboxamide-ethyl-methoxyphenyl] | —C(O)— | Leu | —C(O)NH— |

| CPD # | Y3 | Y2 | Y1 | R2 |
|-------|------|----|------|-----|
| 5192 | —(CH2)2— | — | —NHC(O)— | H |
| 5241 | —(CH2)2— | — | —NHC(O)— | H |
| 5247 | —(CH2)2— | — | —NHC(O)— | H |
| 5262 | —(CH2)2— | — | —NHC(O)— | H |
| 5283 | —CH2— | — | —NHC(O)— | H |
| 5286 | —CH2— | — | —NHC(O)— | H |
| 5292 | —(CH2)2— | — | —NHC(O)— | H |
| 5310 | —CH2— | — | —NHC(O)— | H |
| 5357 | —CH2— | — | —NHC(O)— | H |
| 5358 | —CH2— | — | —NHC(O)— | H |
| 5420 | —(CH2)2— | — | —NHC(O)— | H |
| 5430 | —(CH2)2— | — | —NHC(O)— | H |
| 5450 | —CH2— | — | —NHC(O)— | H |
| 5451 | —CH2— | — | —NHC(O)— | H |
| 5743 | —(CH2)4— | — | —NHC(O)— | H |
| 5750 | —(CH2)2— | — | —NHC(O)— | H |
| 5751 | —(CH2)2— | — | —NHC(O)— | H |
| 5752 | (sec-butyl-phenyl structure) | — | —NHC(O)— | H |
| 5788 | —(CH2)4— | — | —NHC(O)— | H |
| 5800 | (sec-butyl-phenyl structure) | — | —NHC(O)— | H |
| 5801 | —(CH2)4— | — | —NHC(O)— | H |
| 5803 | —(CH2)4— | — | —NHC(O)— | H |
| 6655 | —(CH2)4— | — | —NHC(O)— | H |
| 6668 | —CH2— | — | —NHC(O)— | H |
| 6669 | —CH2— | — | —NHC(O)— | H |
| 6670 | —CH2— | — | —NHC(O)— | H |
| 6671 | —CH2— | — | —NHC(O)— | H |
| 6696 | —(CH2)2— | — | —NHC(O)— | H |
| 6697 | —CH2— | — | —NHC(O)— | H |

-continued

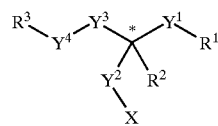

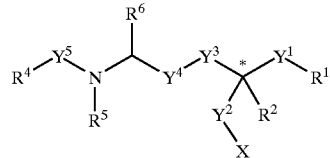

| | | | | |
|---|---|---|---|---|
| 6714 | —CH2— | — | —NHC(O)— | H |
| 6715 | —CH2— | — | —NHC(O)— | H |
| 6716 | —CH2— | — | —NHC(O)— | H |
| 7080 | —(CH2)2— | — | —NHC(O)— | H |
| 7081 | —(CH2)4— | — | —NHC(O)— | H |
| 7083 | ![pyrrolidine structure] | | —NHC(O)— | H |
| 7092 | —(CH2)2— | — | —NHC(O)— | H |
| 7093 | —(CH2)2— | — | —NHC(O)— | H |
| 7106 | —(CH2)2— | — | —NHC(O)— | H |
| 7109 | —(CH2)2— | — | —NHC(O)— | H |
| 7111 | —(CH2)4— | — | —NHC(O)— | H |
| 7116 | —(CH2)2— | — | —NHC(O)— | H |
| 7117 | —(CH2)4— | — | —NHC(O)— | H |
| 7119 | —(CH2)4— | — | —NHC(O)— | H |
| 7147 | —(CH2)4— | — | —NHC(O)— | H |
| 7148 | —(CH2)4— | — | —NHC(O)— | H |
| 7150 | —(CH2)4— | — | —NHC(O)— | H |
| 7155 | —(CH2)3— | — | —NHC(O)— | H |
| 7156 | —(CH2)4— | — | —NHC(O)— | Bn |
| 7157 | —(CH2)4— | — | —NHC(O)— | Bn |
| 7158 | —(CH2)4— | — | —NHC(O)— | Bn |
| 7168 | —(CH2)2— | — | —NHC(O)— | H |
| 7171 | —CH2— | — | —NHC(O)— | H |
| 7172 | —CH2— | — | —NHC(O)— | H |
| 7175 | —CH2— | — | —NHC(O)— | H |
| 7177 | —CH2— | — | —NHC(O)— | H |
| 7181 | —(CH2)2— | — | —NHC(O)— | H |
| 7200 | —(CH2)2— | — | —NHC(O)— | H |
| 7231 | —(CH2)4— | — | —NHC(O)— | H |
| 7233 | —(CH2)4— | — | —NHC(O)— | H |
| 7234 | —(CH2)4— | — | —NHC(O)— | H |
| 7235 | —(CH2)4— | — | —NHC(O)— | H |
| 7236 | —(CH2)4— | — | —NHC(O)— | H |
| 7241 | —(CH2)4— | — | —N(CH3)C(O)— | H |
| 7255 | —(CH2)4— | — | —NHC(O)— | H |
| 7256 | —(CH2)4— | — | —NHC(O)— | H |
| 7257 | —(CH2)4— | — | —NHC(O)— | H |
| 7328 | —(CH2)2— | — | —NHC(O)— | H |
| 7375 | —(CH2)2— | — | —NHC(O)— | H |
| 7398 | —(CH2)2— | — | —NHC(O)— | H |
| 7399 | —(CH2)2— | — | —NHC(O)— | H |
| 7514 | —CH2— | — | —NHC(O)— | H |
| 7515 | —CH2— | — | —NHC(O)— | H |
| 7516 | —CH2— | — | —NHC(O)— | H |
| 7517 | —CH2— | — | —NHC(O)— | H |
| 7528 | —(CH2)2— | — | —NHC(O)— | H |
| 7530 | —(CH2)2— | — | —NHC(O)— | H |
| 7552 | —(CH2)2— | — | —NHC(O)— | H |
| 7578 | —(CH2)2— | — | —NHC(O)— | H |
| 7662 | —(CH2)2— | — | —NHC(O)— | H |
| 7788 | ![aryl propoxy structure] | — | —NHC(O)— | H |

-continued

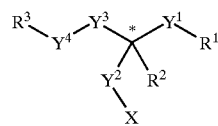

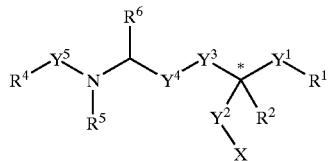

| | | | | | |
|---|---|---|---|---|---|
| 7796 | —(CH2)2— | | — | —NHC(O)— | H |
| 7855 | —(CH2)4— | | CH2 | —NHC(O)— | H |
| 7856 | —(CH2)4— | | CH2 | —NHC(O)— | H |
| 7857 | —(CH2)4— | | CH2 | —NHC(O)— | H |
| 8066 | —(CH2)4— | | CH2 | —NHC(O)— | H |
| 8067 | —(CH2)4— | | CH2 | —NHC(O)— | H |
| 8122 | —(CH2)4— | | CH2 | —NHC(O)— | H |
| 8123 | —(CH2)4— | | CH2 | —NHC(O)— | H |
| 8147 | —(CH2)4— | | CH2 | —NHC(O)— | H |
| 8205 | —(CH2)5— | | — | —NHC(O)— | H |
| 8208 | —(CH2)4— | | CH2 | —NHC(O)— | H |
| 8209 | —(CH2)4— | | CH2 | —NHC(O)— | H |
| 8210 | —(CH2)4— | | CH2 | —NHC(O)— | H |
| 8211 | —(CH2)4— | | CH2 | —NHC(O)— | H |
| 8212 | —(CH2)4— | | CH2 | —NHC(O)— | H |
| 8221 | —(CH2)2— | | — | —NHC(O)— | H |
| 8290 | —(CH2)2— | | — | —NHC(O)— | H |
| 8291 | —(CH2)2— | | — | —NHC(O)— | H |
| 8294 | —(CH2)2— | | — | —NHC(O)— | H |
| 8295 | —(CH2)2— | | — | —NHC(O)— | H |
| 8304 | ![benzene with methyl and ethyl] | | — | —NHC(O)— | H |
| 8308 | —(CH2)2— | | — | —NHC(O)— | H |
| 8309 | —(CH2)2— | | — | —NHC(O)— | H |
| 8341 | —(CH2)2— | | — | —NHC(O)— | H |
| 8342 | —(CH2)2— | | — | —NHC(O)— | H |
| 8343 | —(CH2)2— | | — | —NHC(O)— | H |
| 8345 | —(CH2)4— | | — | —NH— | H |
| 8348 | —(CH2)2— | | — | —NHC(O)— | H |
| 8349 | —(CH2)2— | | — | —NHC(O)— | H |
| 8352 | —(CH2)4— | | — | —NHC(O)O— | H |
| 8354 | —(CH2)2— | | — | —NHC(O)— | H |
| 8355 | ![benzene with methyl and O-propyl] | | — | —NHC(O)— | H |
| 8367 | —(CH2)2— | | — | —NHC(O)— | H |
| 8368 | —(CH2)2— | | — | —NHC(O)— | H |
| 8399 | —(CH2)2— | | — | —NHC(O)— | H |
| 8446 | —(CH2)4— | | — | —NHC(O)O— | H |
| 8449 | —(CH2)4— | | CH2 | —NHC(O)— | H |
| 8450 | —(CH2)4— | | CH2 | —NHC(O)— | H |
| 8451 | —(CH2)4— | | CH2 | —NHC(O)— | H |
| 8452 | —(CH2)4— | | CH2 | —NHC(O)— | H |
| 8453 | —(CH2)4— | | CH2 | —NHC(O)— | H |
| 8455 | —(CH2)4— | | CH2 | —NHC(O)— | H |
| 8456 | —(CH2)4— | | CH2 | —NHC(O)— | H |
| 8457 | —(CH2)4— | | CH2 | —NHC(O)— | H |
| 8458 | —(CH2)4— | | CH2 | —NHC(O)— | H |
| 8459 | —(CH2)4— | | CH2 | —NHC(O)— | H |
| 8460 | —(CH2)4— | | CH2 | —NHC(O)— | H |
| 8461 | —(CH2)4— | | CH2 | —NHC(O)— | H |
| 8462 | —(CH2)4— | | CH2 | —NHC(O)— | H |
| 8463 | —(CH2)4— | | CH2 | —NHC(O)— | H |
| 8464 | —(CH2)4— | | CH2 | —NHC(O)— | H |
| 8465 | —(CH2)4— | | CH2 | —NHC(O)— | H |
| 8466 | —(CH2)4— | | CH2 | —NHC(O)— | H |

-continued
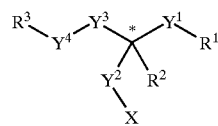
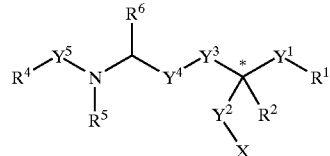
| | | | | |
|---|---|---|---|---|
| 8469 | —(CH2)2— | — | —NHC(O)— | H |
| 8485 | —(CH2)2— | — | —NHC(O)— | H |
| 8488 | | — | —NHC(O)— | H |
| 8491 | —(CH2)2— | — | —NHC(O)— | H |
| 8493 | —(CH2)2— | — | —NHC(O)— | H |
| 8494 | —(CH2)2— | — | —NHC(O)— | H |
| 8513 | —(CH2)4— | CH2 | —NHC(O)— | H |
| 8514 | | — | —NHC(O)— | H |
| 8515 | | — | —NHC(O)— | H |
| 8516 | | — | —NHC(O)— | H |
| 8519 | —(CH2)4— | CH2 | —NHC(O)— | H |
| 8520 | | — | —NHC(O)— | H |
| 8528 | —(CH2)2— | — | —NHC(O)— | H |
| 8552 | —(CH2)2— | — | —NHC(O)— | H |
| 8553 | —(CH2)2— | — | —NHC(O)— | H |
| 8554 | —(CH2)2— | — | —NHC(O)— | H |
| 8555 | —(CH2)2— | — | —NHC(O)— | H |
| 8557 | | — | —NHC(O)— | H |
| 8558 | —(CH2)2— | — | —NHC(O)— | H |
| 8559 | —(CH2)2— | — | —NHC(O)— | H |
| 8566 | —(CH2)2— | — | —NHC(O)— | H |
| 8567 | —(CH2)2— | — | —NHC(O)— | H |
| 8571 | —(CH2)2— | — | —NHC(O)— | H |
| 8582 | —(CH2)2— | — | —NHC(O)— | H |
| 8583 | —(CH2)2— | — | —NHC(O)— | H |
| 8585 | —(CH2)2— | — | —NHC(O)— | H |
| 8586 | —(CH2)2— | — | —NHC(O)— | H |

-continued
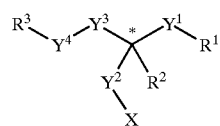
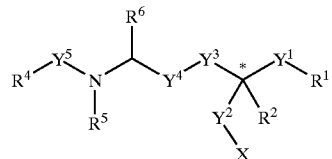
| | | | | |
|---|---|---|---|---|
| 8606 | (structure) | — | —NHC(O)— | H |
| 8607 | (structure) | — | —NHC(O)— | H |
| 8620 | —(CH2)4— | — | —NHC(O)— | H |
| 8621 | —(CH2)4— | — | —NHC(O)— | H |
| 8628 | —(CH2)2— | — | —NHC(O)— | H |
| 8629 | —(CH2)4— | — | —NHC(O)— | H |
| 8630 | —(CH2)4— | — | —NHC(O)— | H |
| 8632 | —(CH2)4— | — | —NHC(O)— | H |
| 8637 | —(CH2)4— | — | —NHC(O)— | H |
| 8638 | —(CH2)4— | — | —NHC(O)— | H |
| 8639 | —(CH2)4— | — | —NHC(O)— | H |
| 8642 | —(CH2)2— | — | —NHC(O)— | H |
| 8643 | —(CH2)2— | — | —NHC(O)— | H |
| 8646 | 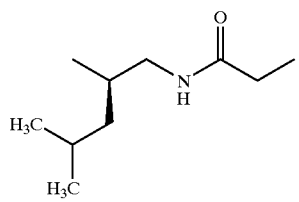 | —CH2— | —NHC(O)— | H |
| 8656 | —(CH2)4— | — | —NHC(O)— | H |
| 8674 | —(CH2)2— | — | —NHC(O)— | H |
| 8684 | (structure) | — | —NHC(O)— | H |
| 8685 | —(CH2)2— | — | —NHC(O)— | H |
| 8689 | —(CH2)2— | — | —NHC(O)— | H |
| 8690 | —(CH2)2— | — | —NHC(O)— | H |
| 8698 | —(CH2)2— | — | —NHC(O)— | H |
| 8723 | —(CH2)2— | — | —NHC(O)— | H |
| 8746 | —(CH2)2— | — | —NHC(O)— | H |
| 8749 | —(CH2)2— | — | —NHC(O)— | H |
| 8758 | —(CH2)2— | — | —NHC(O)— | H |
| 8796 | —(CH2)2— | — | —NHC(O)— | H |
| 8797 | —(CH2)2— | — | —NHC(O)— | H |
| 8809 | —(CH2)2— | — | —NHC(O)— | H |
| 8905 | —CH2— | — | — | H |
| 8906 | —CH2— | — | — | H |
| 8929 | —(CH2)2— | — | —NHC(O)— | H |
| 9120 | —(CH2)2— | — | —NHC(O)— | H |
| 9140 | —(CH2)2— | — | —NHC(O)— | H |
| 9169 | —(CH2)2— | — | —NHC(O)— | H |

-continued
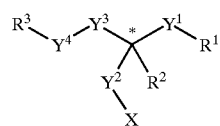
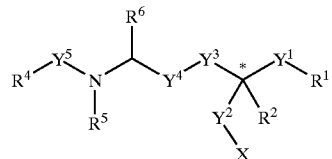
| | | | | |
|---|---|---|---|---|
| 9170 | —(CH2)2— | — | —NHC(O)— | H |
| 9171 | —(CH2)2— | — | —NHC(O)— | H |
| 9182 | —(CH2)2— | — | —NHC(O)— | H |
| 9227 | —(CH2)2— | — | —NHC(O)— | H |
| 9232 | | — | —NHC(O)— | H |
| 9233 | | — | —NHC(O)— | H |
| 9234 | | — | —NHC(O)— | H |
| 9235 | | — | —NHC(O)— | H |
| 9236 | | — | —NHC(O)— | H |
| 9237 | | — | —NHC(O)— | H |
| 9238 | | — | —NHC(O)— | H |
| 9239 | | — | —NHC(O)— | H |
| 9264 | —(CH2)2— | — | —NHC(O)— | H |
| 9270 | | — | —C(O)— | H |
| 9271 | | — | —C(O)— | H |
| 9273 | | — | —C(O)— | H |
| 9274 | | — | —C(O)— | H |
| 9275 | | — | —C(O)— | H |

-continued
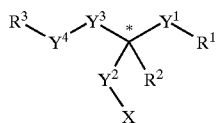
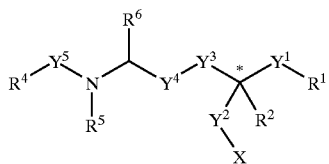
| | | | | |
|---|---|---|---|---|
| 9276 | 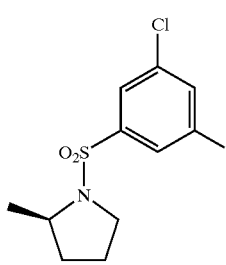 | — | —C(O)— | H |
| 9277 | 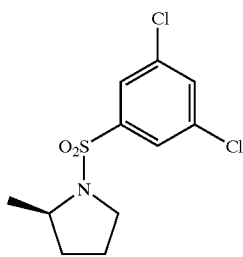 | — | —C(O)— | H |
| 9315 | —(CH2)2— | — | —NHC(O)— | H |
| 9418 | —(CH2)2— | — | —NHC(O)— | H |
| 9437 | —(CH2)2— | — | —NHC(O)— | H |
| 9621 | —(CH2)2— | — | —NHC(O)— | H |
| CPD # | R1 | X | *Con lg. |
|---|---|---|---|
| 5192 | 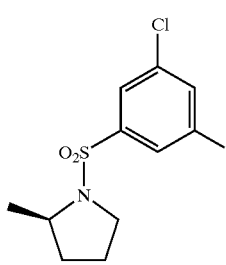 | CO2H | S |
| 5241 | 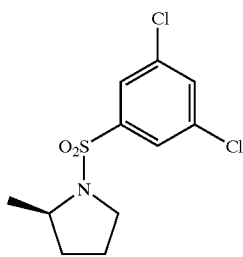 | CO2H | S |
| 5247 | 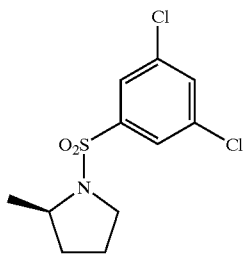 | CO2H | S |

-continued
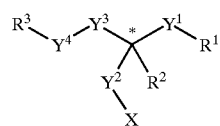
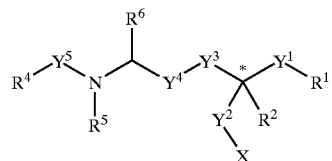
| | | | |
|---|---|---|---|
| 5262 | 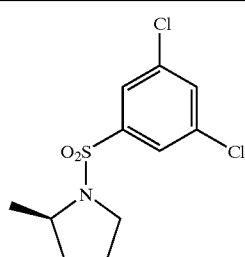 | CO2H | S |
| 5283 | 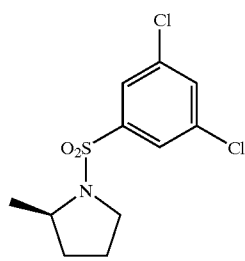 | CO2H | S |
| 5286 | 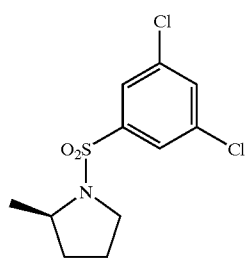 | CO2H | S |
| 5292 | 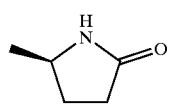 | CO2H | S |
| 5310 | 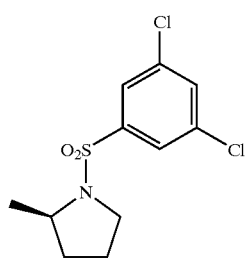 | CO2H | S |
| 5357 | 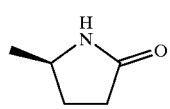 | CO2H | S |
| 5358 | CH3 | CO2H | S |

-continued
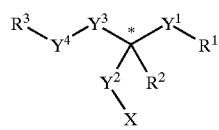
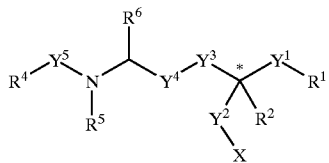
| | | | |
|---|---|---|---|
| 5420 | 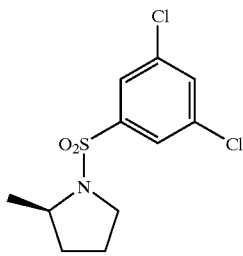 | CO2H | S |
| 5430 | 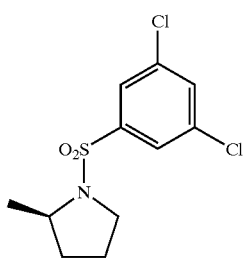 | CO2H | S |
| 5450 | 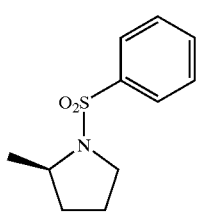 | CO2H | S |
| 5451 | 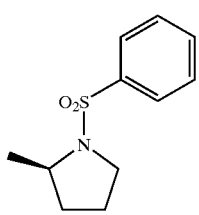 | CO2H | S |
| 5743 | 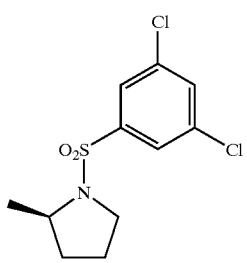 | CO2H | S |

-continued
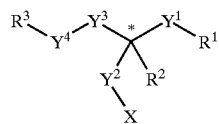
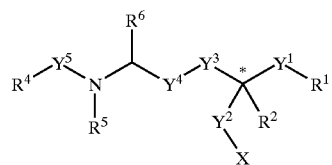
| | | | |
|---|---|---|---|
| 5750 | 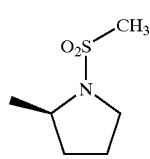 | CO2H | S |
| 5751 | 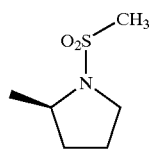 | CO2H | S |
| 5752 | 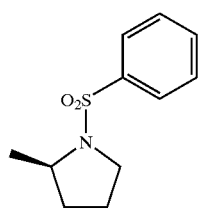 | CO2H | S |
| 5788 | 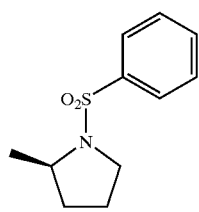 | CO2H | S |
| 5800 | 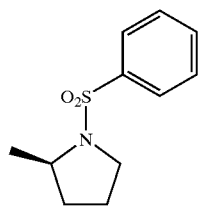 | CO2H | S |
| 5801 | 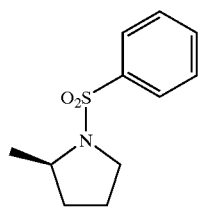 | CO2H | S |

-continued
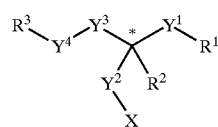
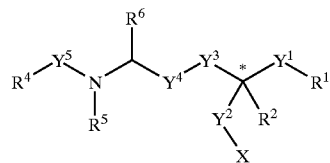
| | | | |
|---|---|---|---|
| 5803 | 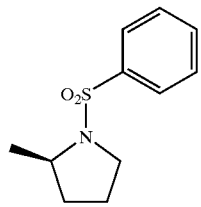 | CO2H | S |
| 6655 | CH3 | CO2H | S |
| 6668 | 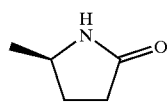 | CO2H | S |
| 6669 | 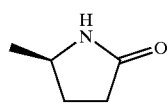 | CO2H | S |
| 6670 | 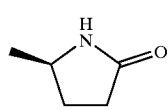 | CO2H | S |
| 6671 | 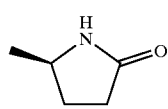 | CO2H | S |
| 6696 | 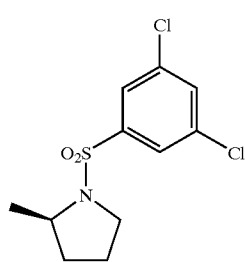 | CO2H | S |
| 6697 | 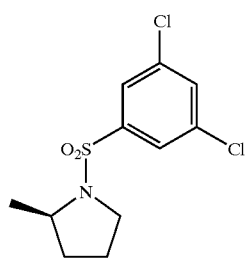 | CO2H | S |

-continued
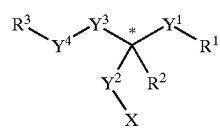
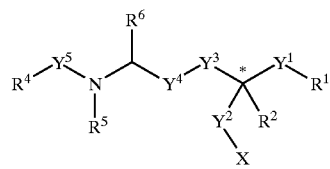
| | | | |
|---|---|---|---|
| 6714 | 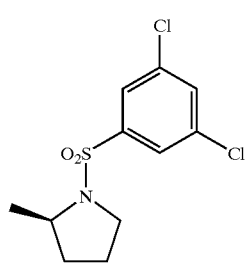 | CO2H | S |
| 6715 | 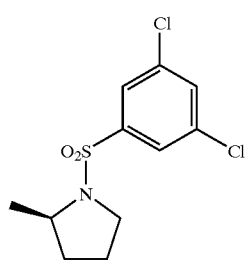 | CO2H | S |
| 6716 | 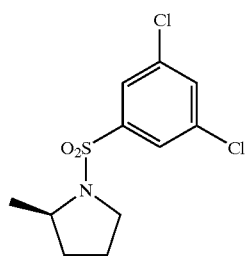 | CO2H | S |
| 7080 | 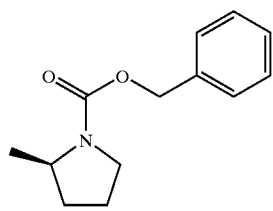 | CO2H | S |
| 7081 | 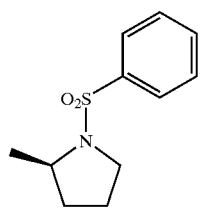 | CO2H | S |

-continued
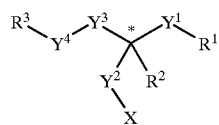
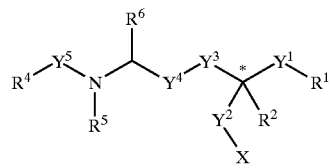
| | | | |
|---|---|---|---|
| 7083 | 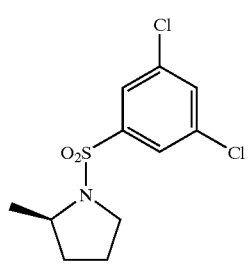 | CO2H | S |
| 7092 | 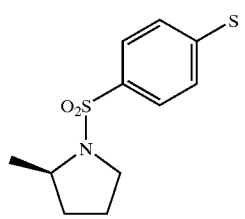 | CO2H | S |
| 7093 | 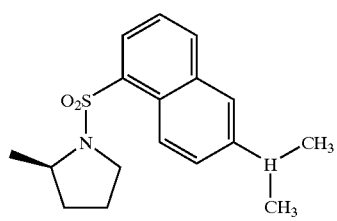 | CO2H | S |
| 7106 | 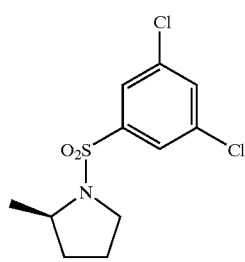 | CO2H | S |
| 7109 | 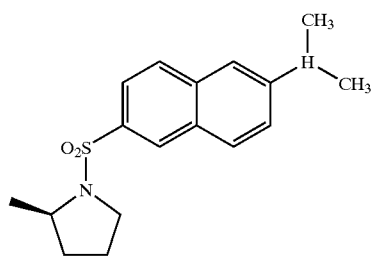 | CO2H | S |

-continued
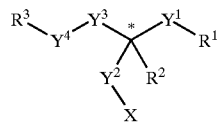
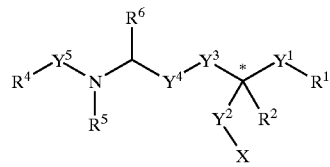
| | | | |
|---|---|---|---|
| 7111 | 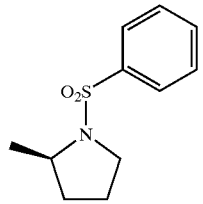 | CO2H | S |
| 7116 | 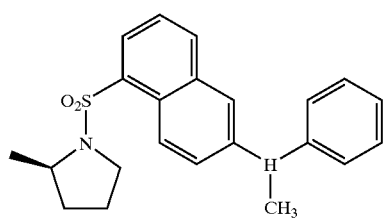 | CO2H | S |
| 7117 | CH3 | CO2H | S |
| 7119 | CH3 | CO2H | S |
| 7147 | 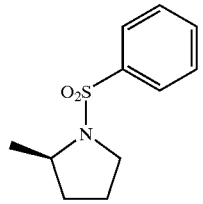 | CO2H | S |
| 7148 | 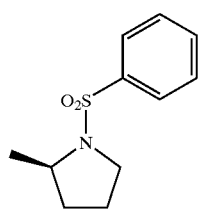 | CO2H | S |
| 7150 | 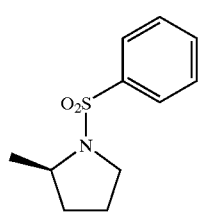 | CO2H | S |

-continued
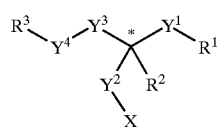
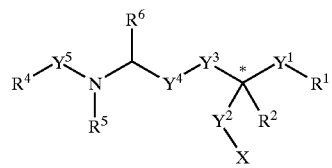
| | | | |
|---|---|---|---|
| 7155 | 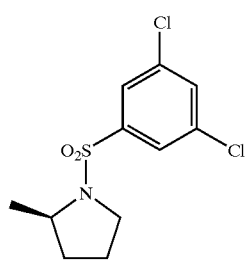 | CO2H | S |
| 7156 | 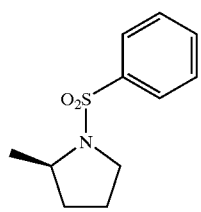 | CO2H | R/S |
| 7157 | 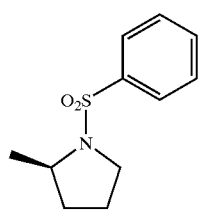 | CO2H | R/S |
| 7158 | 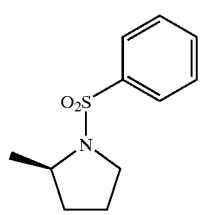 | CO2H | R/S |
| 7168 | 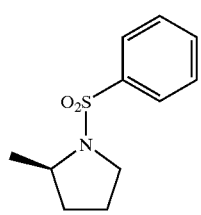 | CO2H | S |
| 7171 | 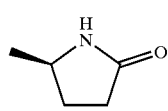 | CO2H | S |

-continued
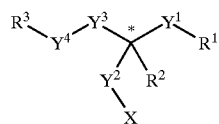
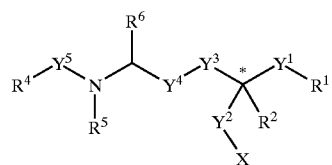
| | | | |
|---|---|---|---|
| 7172 | 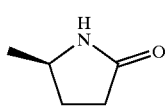 | CO2H | S |
| 7175 | 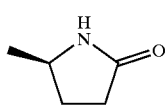 | CO2H | S |
| 7177 | 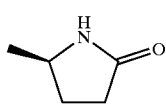 | CO2H | S |
| 7181 | 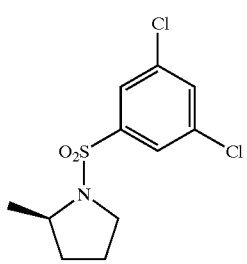 | CO2CH3 | S |
| 7200 | 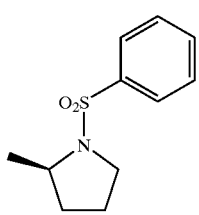 | CO2H | S |
| 7231 | 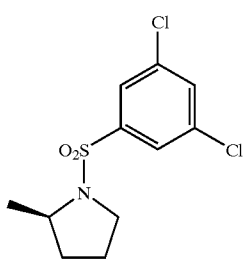 | CO2H | S |

-continued
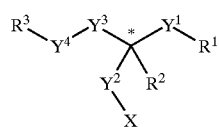
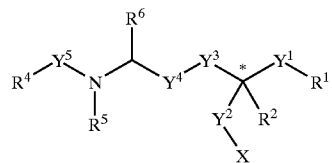
| | | | |
|---|---|---|---|
| 7233 | 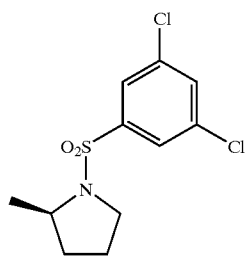 | CO2H | S |
| 7234 | 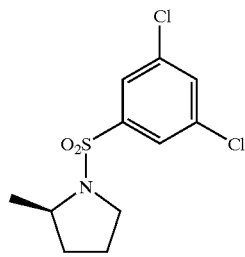 | CO2H | S |
| 7235 | 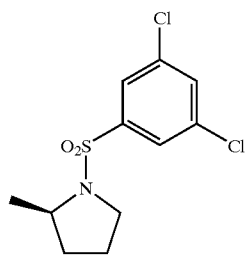 | CO2H | S |
| 7236 | 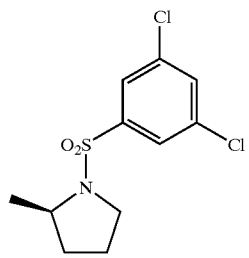 | CO2H | S |
| 7241 | 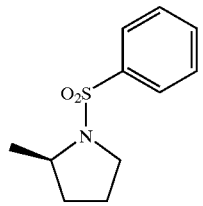 | CO2H | S |

-continued
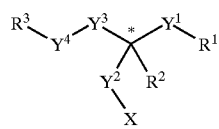
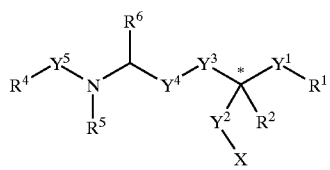
| | | | |
|---|---|---|---|
| 7255 | 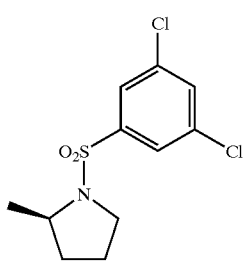 | CO2H | S |
| 7256 | 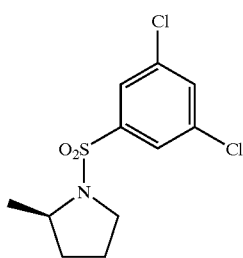 | CO2H | S |
| 7257 | 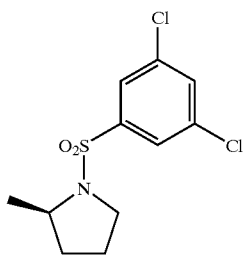 | CO2H | S |
| 7328 | 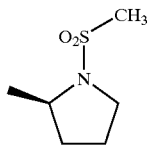 | CO2H | S |
| 7375 | 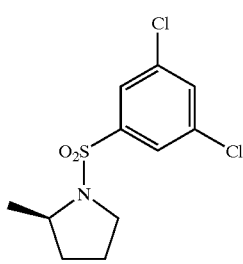 | CO2H | S |

-continued
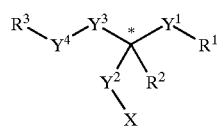
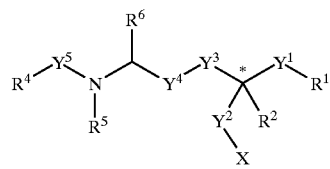
| | | | |
|---|---|---|---|
| 7398 | 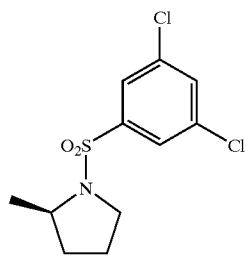 | CONHCH3 | S |
| 7399 | 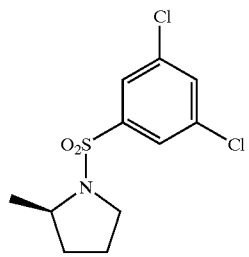 | CO2H | S |
| 7514 | 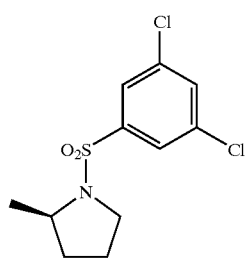 | CO2H | S |
| 7515 | 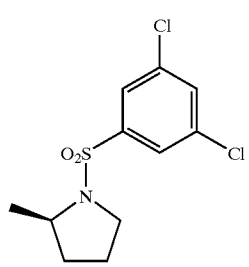 | CO2H | S |
| 7516 | 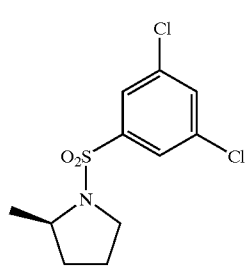 | CO2H | S |

-continued
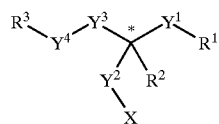
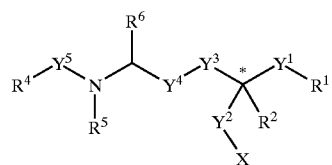
| | | | |
|---|---|---|---|
| 7517 | 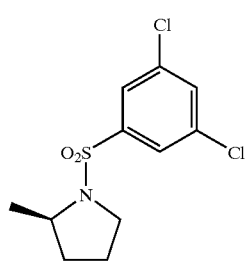 | CO2H | S |
| 7528 | 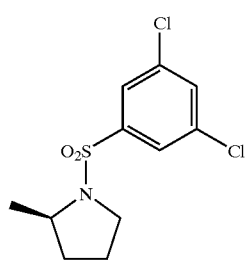 | CO2H | S |
| 7530 | 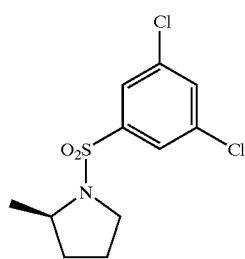 | CO2H | S |
| 7552 | 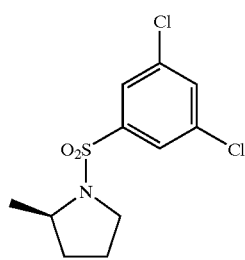 | CO2H | S |

-continued
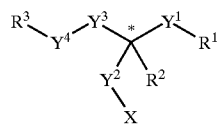
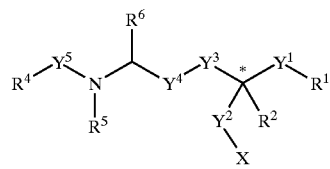
| | | | |
|---|---|---|---|
| 7578 | 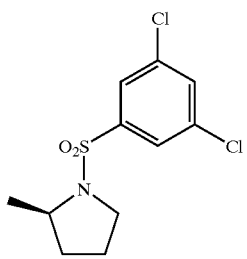 | CO2H | S |
| 7662 | 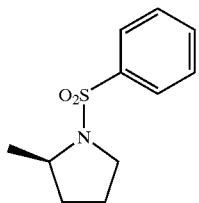 | CO2H | S |
| 7788 | 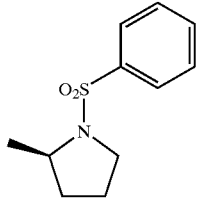 | CO2H | S |
| 7796 | 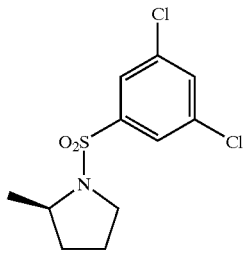 | CH2OH | S |
| 7855 | 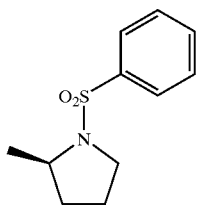 | CO2H | S |

-continued
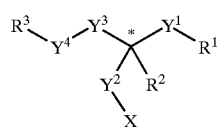
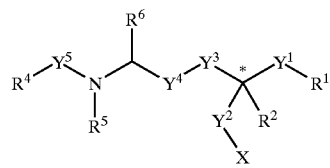
| | | | |
|---|---|---|---|
| 7856 | 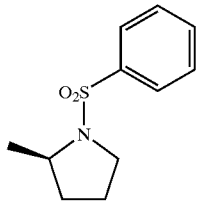 | CO2H | S |
| 7857 | 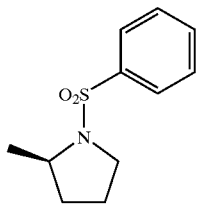 | CO2H | S |
| 8066 | 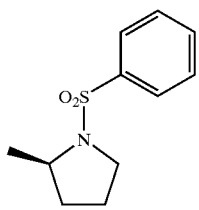 | CO2H | S |
| 8067 | 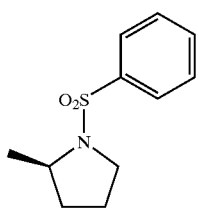 | CO2H | S |
| 8122 | 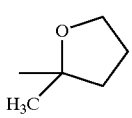 | CO2H | S |
| 8123 | 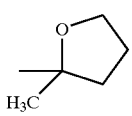 | CO2H | S |
| 8147 | 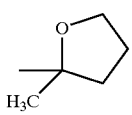 | CO2H | S |

-continued
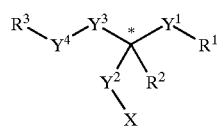
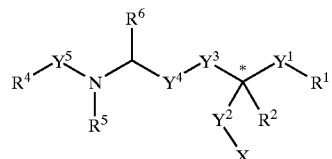
| | | | |
|---|---|---|---|
| 8205 | 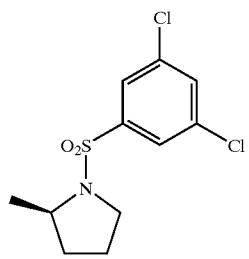 | CO2H | S |
| 8208 | CH3 | CO2H | S |
| 8209 | oMePUPCH2 | CO2H | S |
| 8210 | CH3 | CO2H | S |
| 8211 | oMePUPCH2 | CO2H | S |
| 8212 | 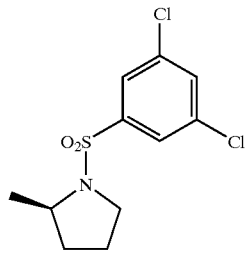 | CO2H | S |
| 8221 | 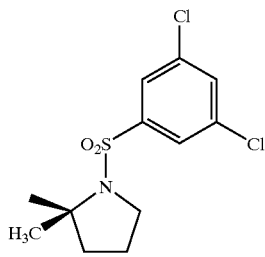 | CO2H | S |
| 8290 | 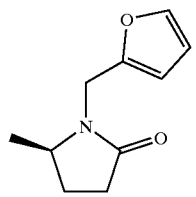 | CO2H | S |
| 8291 | 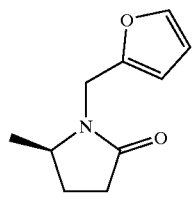 | CO2H | S |

-continued
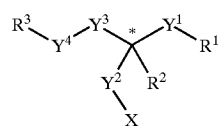
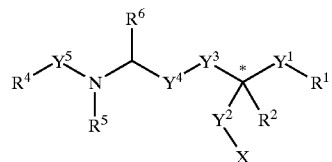
| | | | |
|---|---|---|---|
| 8294 | 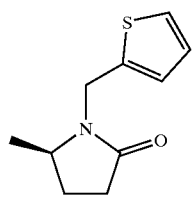 | CO2H | S |
| 8295 | 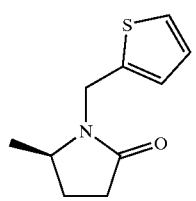 | CO2H | S |
| 8304 | 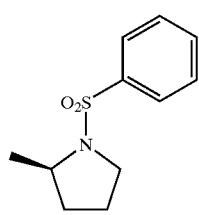 | CO2H | S |
| 8308 | 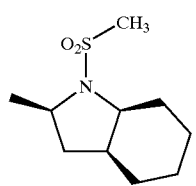 | CO2H | S |
| 8309 | 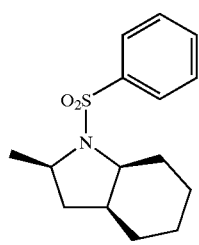 | CO2H | S |
| 8341 | 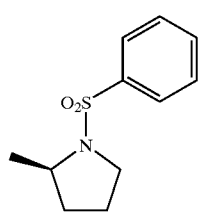 | CO2H | S |

-continued
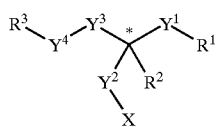
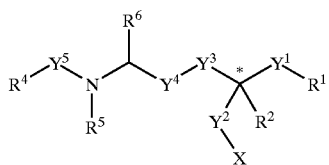
| | | | | |
|---|---|---|---|---|
| 8342 | 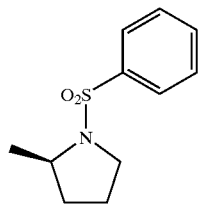 | | CO2H | R |
| 8343 | 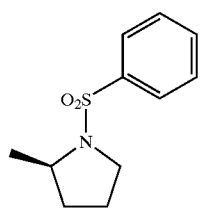 | | CO2H | R |
| 8345 | H | | CO2H | S |
| 8348 | 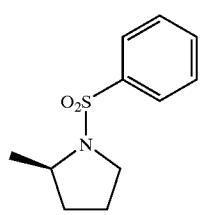 | | CO2H | R |
| 8349 | 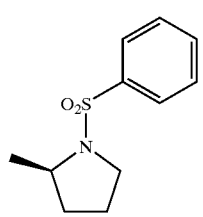 | | CO2H | R |
| 8352 | tBu | | CO2H | S |
| 8354 | 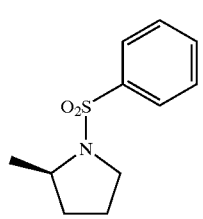 | | CO2H | R |

-continued
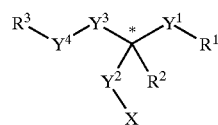
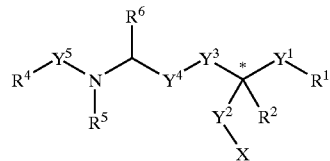
| | | | |
|---|---|---|---|
| 8355 | 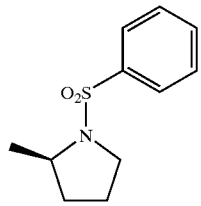 | CO2H | R |
| 8367 | 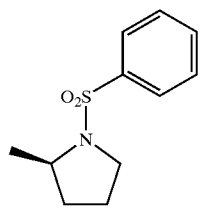 | CO2H | S |
| 8368 | 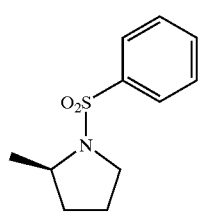 | CO2H | S |
| 8399 | 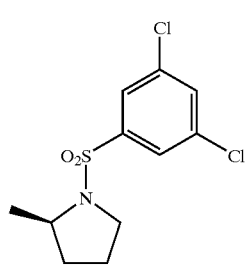 | CO2H | S |
| 8446 | Bn | CO2H | S |
| 8449 | 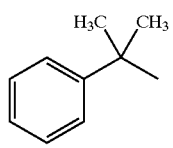 | CO2H | S |
| 8450 | 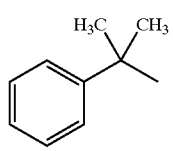 | CO2H | S |

-continued
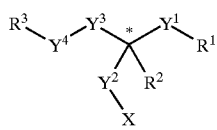
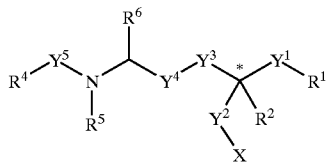
| | | | | |
|---|---|---|---|---|
| 8451 | 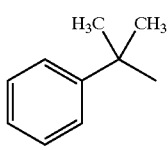 | | CO2H | S |
| 8452 | 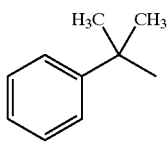 | | CO2H | S |
| 8453 | 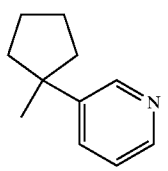 | | CO2H | S |
| 8455 | 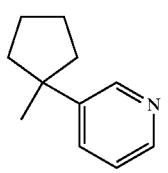 | | CO2H | S |
| 8456 | 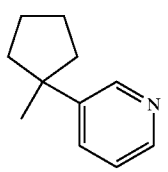 | | CO2H | S |
| 8457 | 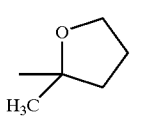 | | CO2H | S |
| 8458 | 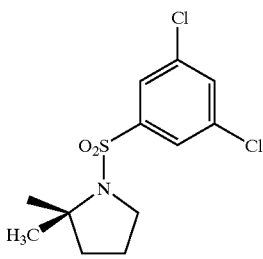 | | CO2H | S |

-continued
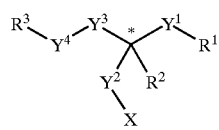
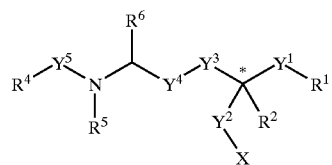
| 8459 | 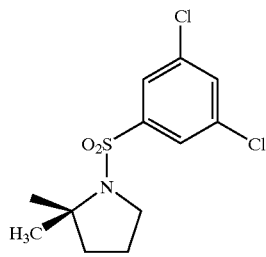 | CO2H | S |
|---|---|---|---|
| 8460 | 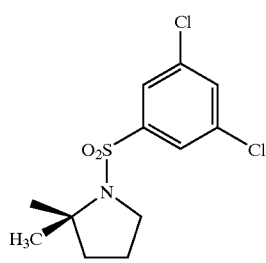 | CO2H | S |
| 8461 | 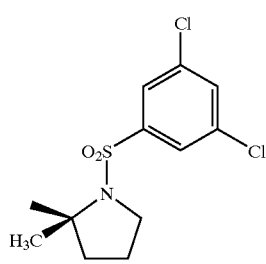 | CO2H | S |
| 8462 | oMePUPA-Leu | CO2H | S |
| 8463 | oMePUPA-Leu | CO2H | S |
| 8464 | oMePUPA-Leu | CO2H | S |
| 8465 | CH3 | CO2H | S |
| 8466 | CH3 | CO2H | S |
| 8469 | 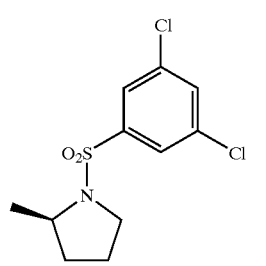 | CO2H | S |

-continued
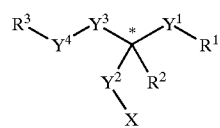
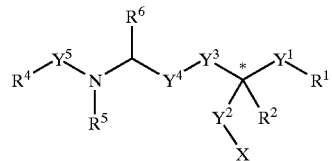
| | | | |
|---|---|---|---|
| 8485 | 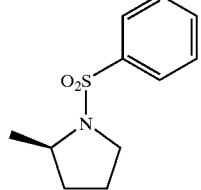 | CO2H | S |
| 8488 | 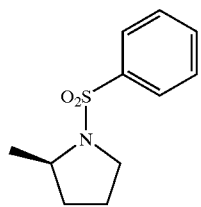 | CO2H | S |
| 8491 | 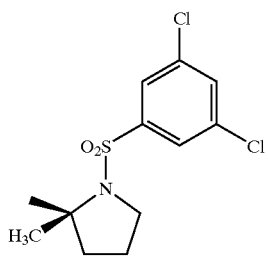 | CO2H | S |
| 8493 | 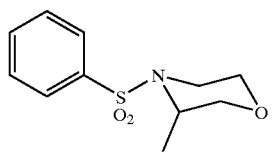 | CO2H | S |
| 8494 | 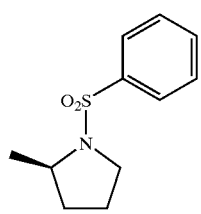 | CO2H | S |
| 8513 | 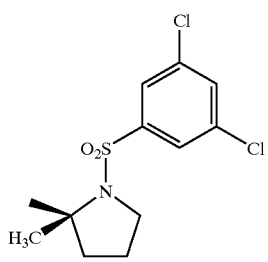 | CO2H | S |

-continued
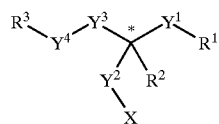
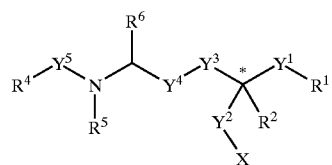
| | | | |
|---|---|---|---|
| 8514 | 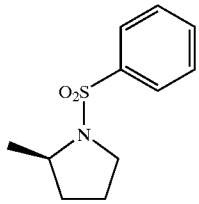 | CO2H | S |
| 8515 | 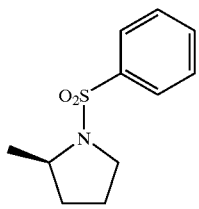 | CO2H | S |
| 8516 | 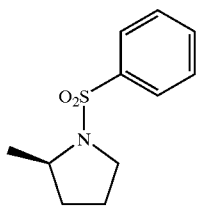 | CO2H | S |
| 8519 | 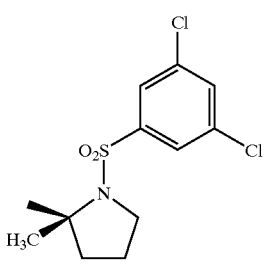 | CO2H | S |
| 8520 | 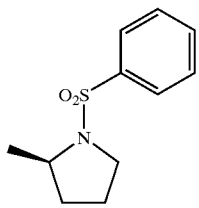 | CO2H | S |

-continued
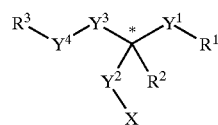
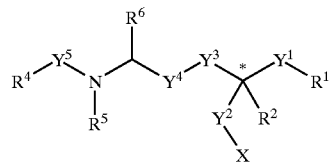
| | | | |
|---|---|---|---|
| 8528 | 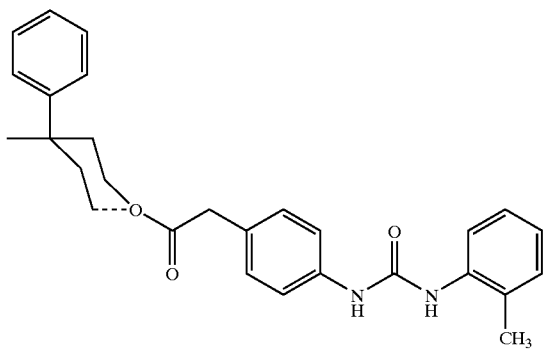 | CO2H | S |
| 8552 | 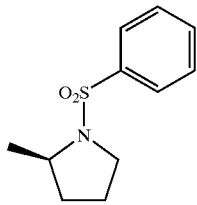 | CO2H | S |
| 8553 | 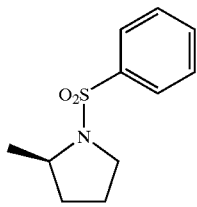 | CO2H | S |
| 8554 | 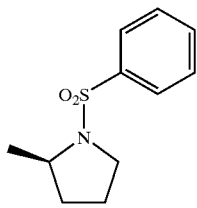 | CO2H | S |
| 8555 | 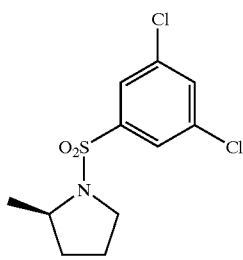 | CO2H | S |

-continued
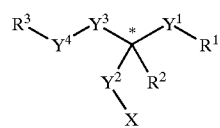
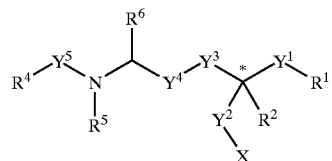
| | | | |
|---|---|---|---|
| 8557 | 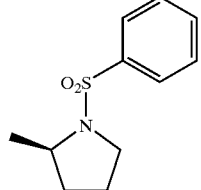 | CO2H | S |
| 8558 | 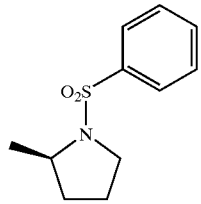 | CO2H | S |
| 8559 | 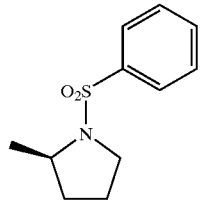 | CO2H | S |
| 8566 | 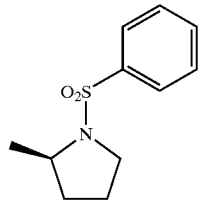 | CO2H | S |
| 8567 | 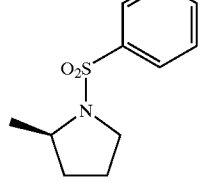 | CO2H | S |
| 8571 | 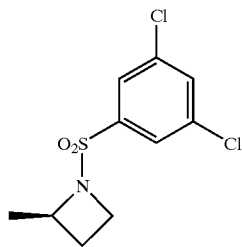 | CO2H | S |

-continued
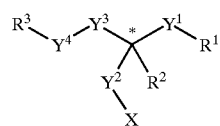
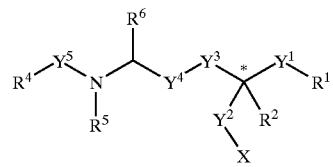
| | | | |
|---|---|---|---|
| 8582 | 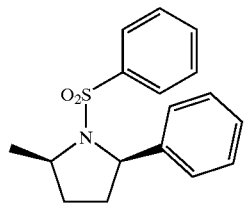 | CO2H | S |
| 8583 | 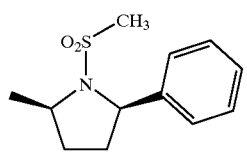 | CO2H | S |
| 8585 | 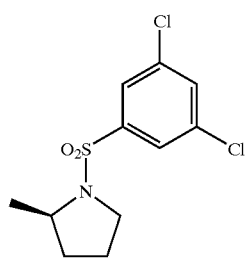 | CO2H | S |
| 8586 | 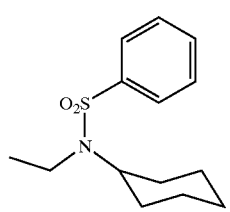 | CO2H | S |
| 8606 | 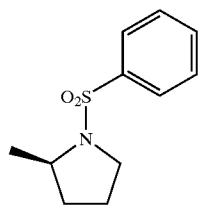 | CO2H | S |
| 8607 | 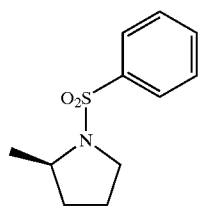 | CO2H | S |

-continued
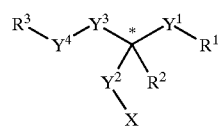
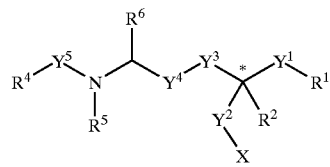
| | | | |
|---|---|---|---|
| 8620 | 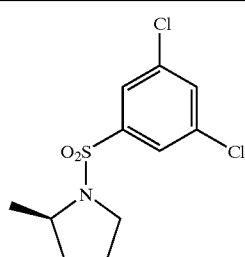 | CO2H | R |
| 8621 | 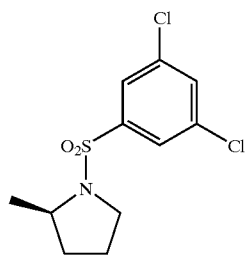 | CO2H | R |
| 8628 | 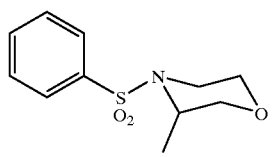 | CO2H | S |
| 8629 | 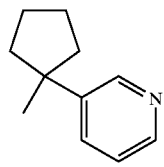 | CO2H | R |
| 8630 | 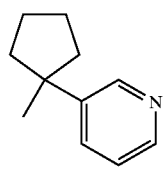 | CO2H | R |
| 8632 | 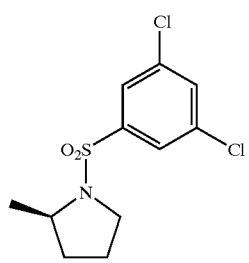 | CO2H | R |

-continued
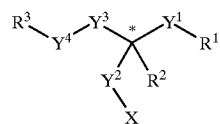
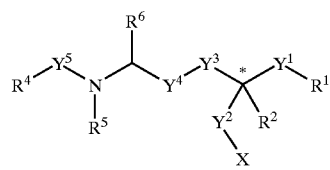
| | | | |
|---|---|---|---|
| 8637 | 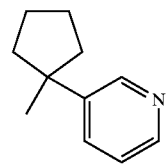 | CO2H | R |
| 8638 | 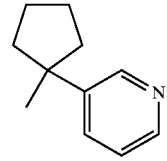 | CO2H | R |
| 8639 | 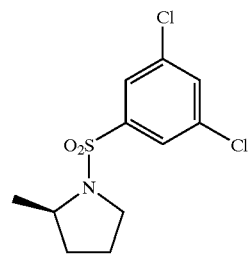 | CO2H | R |
| 8642 | 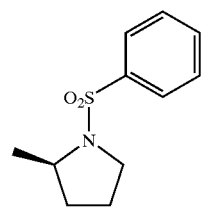 | CO2H | S |
| 8643 | 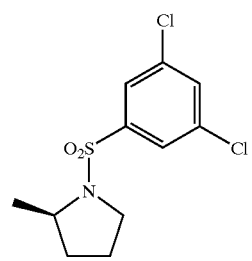 | CO2H | S |

-continued
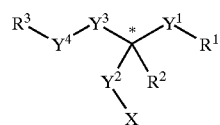
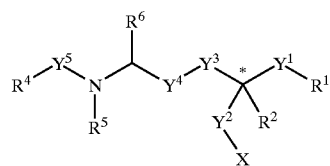
| | | | |
|---|---|---|---|
| 8646 | 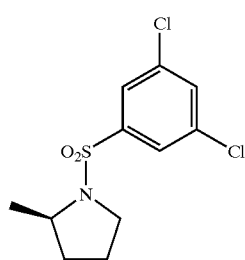 | CO2H | S |
| 8656 | 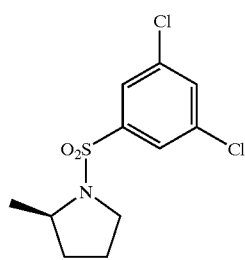 | CO2H | R |
| 8674 | 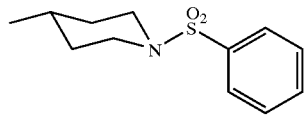 | CO2H | S |
| 8684 | 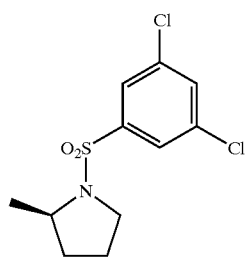 | CO2H | S |
| 8685 | 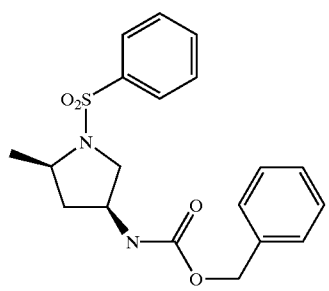 | CO2H | S |

-continued
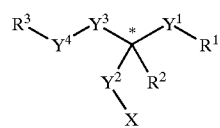
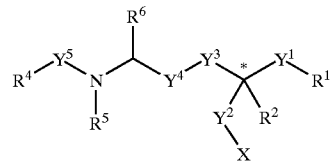
| 8689 | 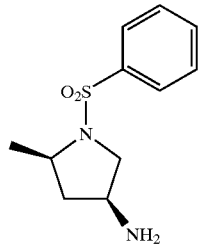 | CO2H | S |
| 8690 | 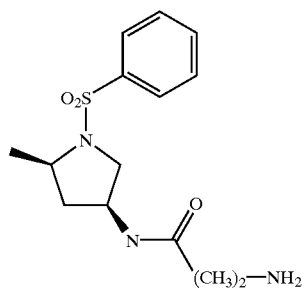 | CO2H | S |
| 8698 | 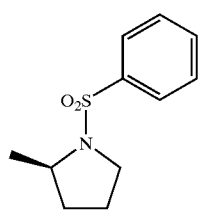 | CO2H | S |
| 8723 | 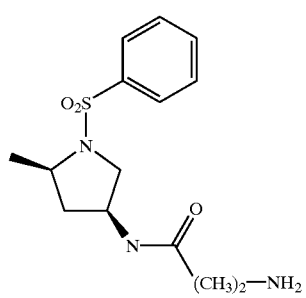 | CO2H | S |
| 8746 | 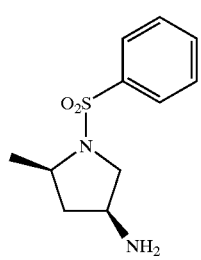 | CO2H | S |

-continued
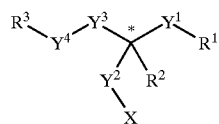
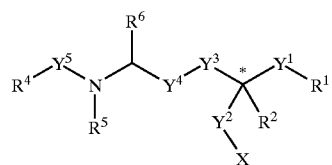
| | | | |
|---|---|---|---|
| 8749 | 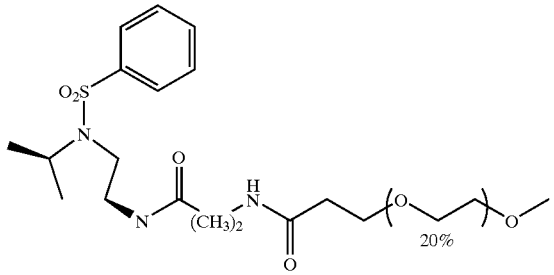 | CO2H | S |
| 8758 | 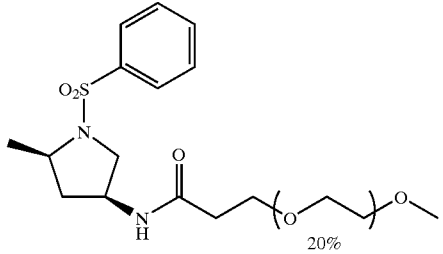 | CO2H | S |
| 8796 | 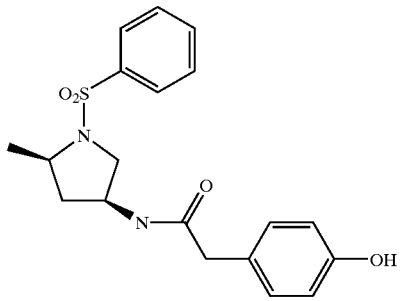 | CO2H | S |
| 8797 | 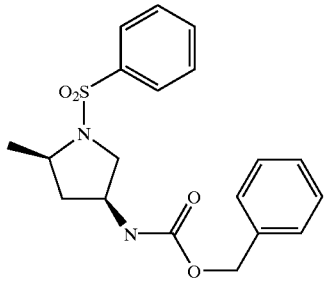 | CO2H | S |

-continued
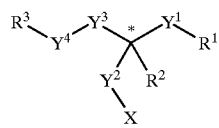
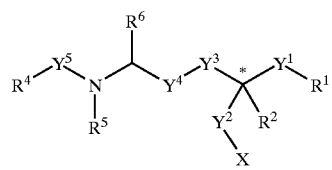
| | | | |
|---|---|---|---|
| 8809 | 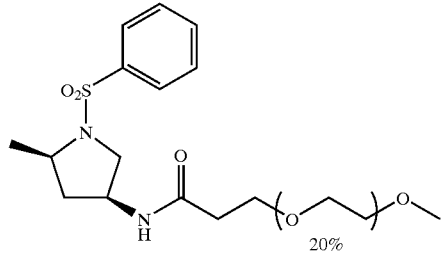 | CO2H | S |
| 8905 | 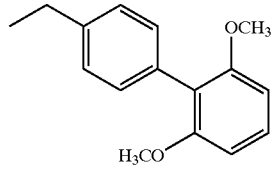 | CO2H | R/S |
| 8906 | 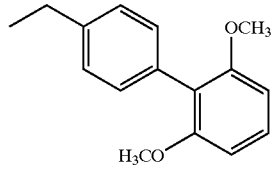 | CO2H | R/S |
| 8929 | 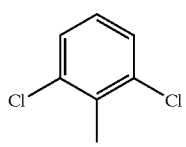 | CO2H | S |
| 9120 | 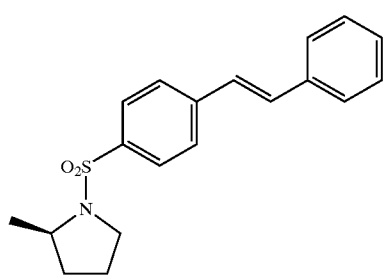 | CO2H | S |
| 9140 | —CH3 | CO2H | S |

-continued
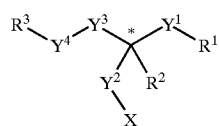
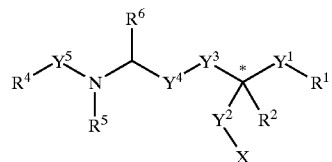
| | | | |
|---|---|---|---|
| 9169 | 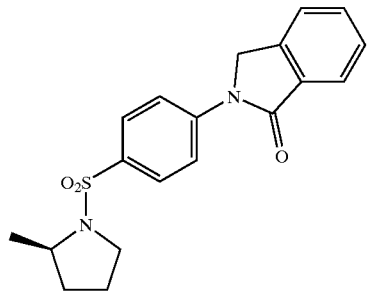 | CO2H | S |
| 9170 | 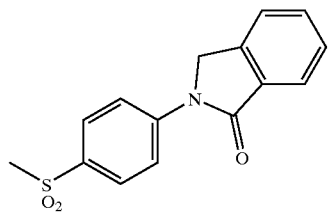 | CO2H | S |
| 9171 | 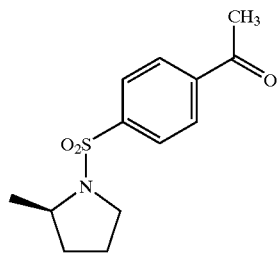 | CO2H | S |
| 9182 | 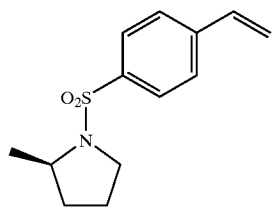 | CO2H | S |
| 9227 | 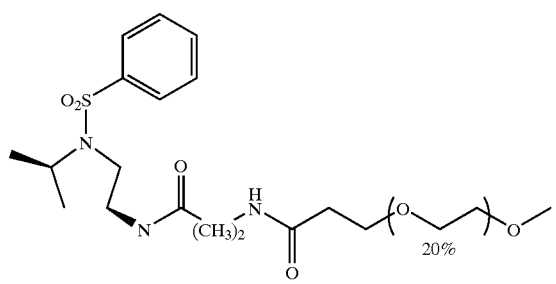 | CO2H | S |

-continued
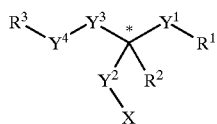
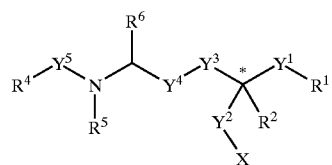
| | | | |
|---|---|---|---|
| 9232 | 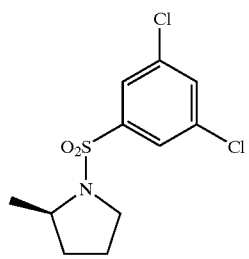 | CO2H | S |
| 9233 | 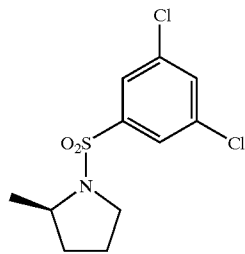 | CO2H | S |
| 9234 | 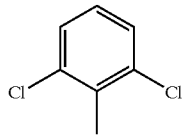 | CO2H | S |
| 9235 | 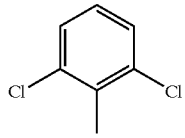 | CO2H | S |
| 9236 | 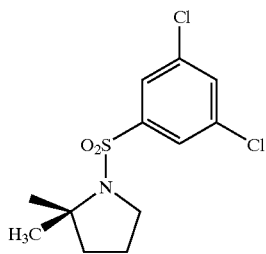 | CO2H | S |

-continued
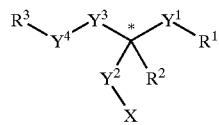
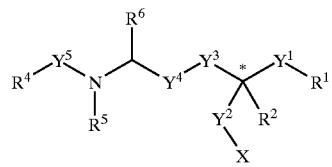
| | | | |
|---|---|---|---|
| 9237 | 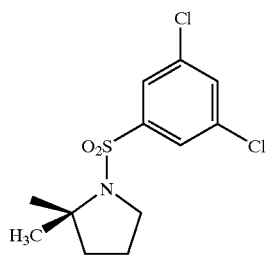 | CO2H | S |
| 9238 | 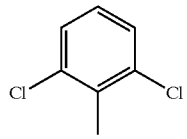 | CO2H | S |
| 9239 | 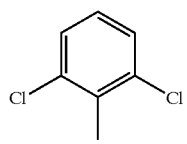 | CO2H | S |
| 9264 | 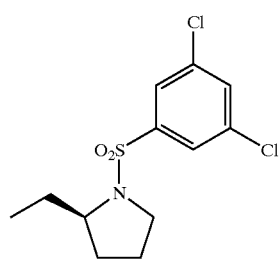 | CO2H | S |
| 9270 | 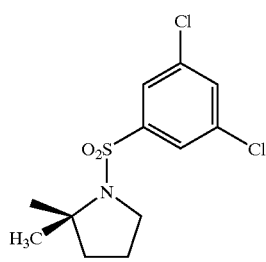 | CO2H | S |

-continued
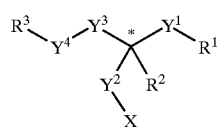
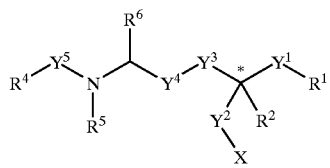
| | | | |
|---|---|---|---|
| 9271 | 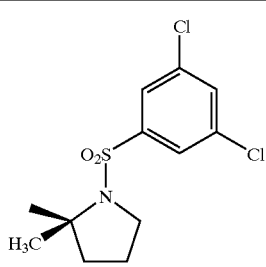 | CO2H | S |
| 9273 | 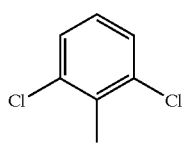 | CO2H | S |
| 9274 | 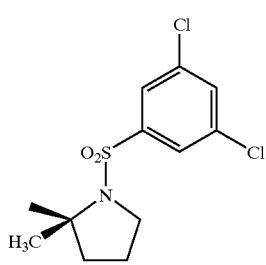 | CO2H | S |
| 9275 | 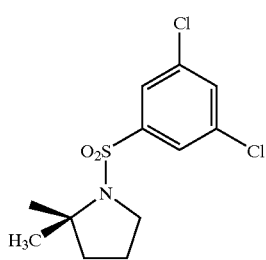 | CO2H | S |
| 9276 | 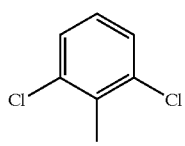 | CO2H | S |
| 9277 | 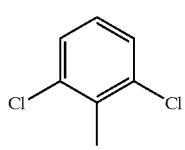 | CO2H | S |

-continued

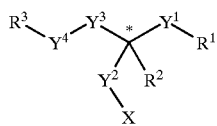

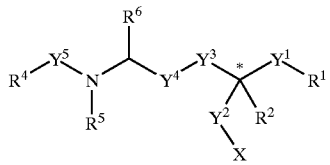

| | | | |
|---|---|---|---|
| 9315 | 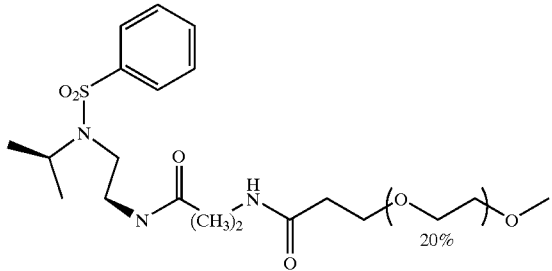 | CO2H | S |
| 9418 | 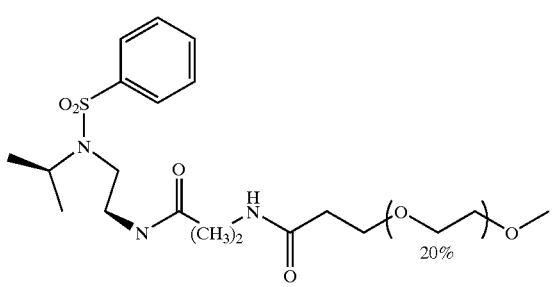 | CO2H | S |
| 9437 | 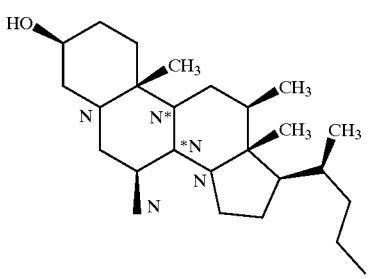 | CO2H | S |
| 9621 | 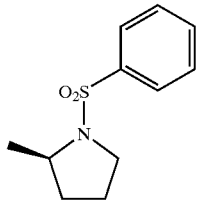 | CO2H | S |

Another aspect of this invention relates to the use of one or more of the inhibitors described above or a salt thereof for the manufacture of a medicament for treating the above-mentioned disorders.

A further aspect of this invention relates to a composition comprising a pharmaceutical carrier and an effective amount of a compound of formula (I), supra Still a further aspect of this invention relates to a method of inhibiting VLA-4-dependent cell adhesion, comprising administering to a patient in need thereof an effective amount of a compound of formula (I), supra.

The ability of the compounds of this invention to antagonize the actions of VLA4 makes them useful for preventing, treating, or reversing the symptoms, disorders or diseases induced by the binding of VLA4 to its ligands. Thus these antagonists will inhibit cell adhesion processes including cell activation, migration, proliferation and differentiation. Accordingly, another aspect of the present invention provides methods for the treatment, prevention, alleviation, or suppression of diseases or disorders mediated by the VLA4 pathway. Such diseases and disorders include, for example, asthma, multiple sclerosis, allergic rhinitis, allergic conjunctivitis, inflammatory lung diseases, rheumatoid arthritis, septic arthritis, type I diabetes, organ transplant rejection, inflammatory bowel disease, and others.

Compounds of the invention contain one or more asymmetric centers and thus can occur as racemates and racemic mixtures, single enantiomers, diastereomeric mixtures and individual diasteromers. The present invention is meant to comprehend all such isomeric forms of the compounds of the invention.

The claimed invention is also intended to encompass pharmaceutically acceptable salts of Formula I. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium and sodium salts.

Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropyulamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, suflfric, tartaric, p-toluenesulfonic acid, and the like. Particularly preferred are citric, hydrobromic, hydrochloric, maleic, phosphoric, sulfuric and tartaric acids.

As used herein, the term "alkyl," alone or in combination, refers to a straight-chain or branched-chain alkyl radical containing from 1 to 10, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, iso-amyl, hexyl, decyl and the like.

The term "alkenyl," alone or in combination, refers to a straight-chain or branched-chain alkenyl radical containing from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like.

The term "alkynyl," alone or in combination, refers to a straight-chain or branched-chain alkynyl radical containing from 2 to 10, preferably from 2 to 6 and more preferably from 2 to 4, carbon atoms. Examples of such radicals include, but are not limited to, ethynyl (acetylenyl), propynyl, propargyl, butynyl, hexynyl, decynyl and the like.

The term "hydrocarbon linker moiety" refers to an alkylene moiety which may contain one or more double or triple bonds. For example, L can be 3-methyloctylene (i.e., a straight chain containing 8 carbon chain atoms) interrupted by, or terminally attached to, an amide linkage (—NH—CO—).

The term "cycloalkyl," alone or in combination, refers to a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl and the like.

The term "cycloalkenyl," alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like.

The term "aryl" refers to a carbocyclic aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to three substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N—Ar' guanidino, N—N—(Ar',alkyl) guanidino, N,N—(Ar',Ar')guanidino, N,N-dialkyl guanidino, N,N,N-trialkyl guanidino, N-alkyl urea, N,N- dialkyl urea, N—Ar' urea, N,N—(Ar',alkyl) urea and N,N—(Ar')$_2$ urea; wherein "Ar" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a radical of formnula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like. The term "alkynyloxy", alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino," alone or in combination, refers to a mono- or di-alkyl-substituted amino radical (i.e., a radical of formula alkyl-NH— or (alkyl)$_2$—N—), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino," alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino," alone or in combination, refers to a radical of formula alkynyl-NH— or (alkynyl)$_2$N—, wherein the term "alkynyl" is as defined above, provided that the radical is not an ynamine. An example of such alkynylamino radicals is the propargyl amino radical.

The term "aryloxy," alone or in combination, refers to a radical of formula aryl-O—, wherein aryl is as defined above. Examples of aryloxy radicals include, but are not limited to, phenoxy, naphthoxy, pyridyloxy and the like.

The term "arylamino," alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "biaryl," alone or in combination, refers to a radical of formula aryl-aryl-, wherein the term "aryl" is as defined above.

The term "thioaryl," alone or in combination, refers to a radical of formula aryl-S—, wherein the term "aryl" is as defined above. An example of a thioaryl radical is the thiophenyl radical.

The term "aryl-fused cycloalkyl," alone or in combination, refers to a cycloalkyl radical which shares two adjacent atoms with an aryl radical, wherein the terms "cycloalkyl" and "aryl" are as defined above. An example of an aryl-fused cycloalkyl radical is the benzo-fused cyclobutyl radical.

The term "aliphatic acyl," alone or in combination, refers to radicals of formnula alkyl-CO—, alkenyl-CO— and alkynyl-CO-derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl and the like.

The term "aromatic acyl," alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The terms "morpholinocarbonyl" and "thiomorpholinocarbonyl," alone or in combination with other terms, refer to an N-carbonylated morpholino and an N-carbonylated thiomorpholino radical, respectively.

The term "alkylcarbonylamino," alone or in combination, refers to a radical of formula alkyl-CONH, wherein the term "alkyl" is as defined above.

The term "alkoxycarbonylamino," alone or in combination, refers to a radical of formula alkyl-OCONH—, wherein the term "alkyl" is as defined above.

The term "alkylsulfonylamino," alone or in combination, refers to a radical of formula alkyl-SO$_2$NH—, wherein the term "alkyl" is as defined above.

The term "arylsulfonylamino," alone or in combination, refers to a radical of formula aryl-SO$_2$NH—, wherein the term "aryl" is as defined above.

The term "N-alkylurea," alone or in combination, refers to a radical of formula alkyl-NH—CO—NH—, wherein the term "alkyl" is as defined above.

The term "N-arylurea," alone or in combination, refers to a radical of formula aryl-NH—CO—NH—, wherein the term "aryl" is as defined above.

The term "halogen" means fluorine, chlorine, bromine and iodine.

The term "leaving group" generally refers to groups readily displaceable by a nucleophile, such as an amine, and alcohol or a thiol nucleophile. Such leaving groups are well known and include carboxylates, N-hydroxysuccinimide, N-hydroxybenzotriazole, halogen (halides), triflates, tosylates, mesylates, alkoxy, thioalkoxy and the like.

The terms "activated derivative of a suitably protected α-amino acid" and "activated substituted-phenylacetic acid derivative" refer to the corresponding acyl halides (e.g. acid fluoride, acid chloride and acid bromide), corresponding activated esters (e.g. nitrophenyl ester, the ester of 1-hydroxybenzotriazole, HOBT, or the ester of hydroxysuccinimide, HOSu), and other conventional derivatives within the skill of the art.

As used throughout this application, the term "patient" refers to mammals, including humans. And the term "cell" refers to mammalian cells, including human cells.

In view of the above definitions, other chemical terms used throughout this application can be easily understood by those of skill in the art. Terms may be used alone or in any combination thereof. The preferred and more preferred chain lengths of the radicals apply to all such combinations.

Other features or advantages of the present invention will be apparent from the following detailed description of several embodiments, and also from the appending claims.

DETAILED DESCRIPTION

Compounds of this invention may be synthesized using any conventional technique, several of which are exemplified herein. Preferably, these compounds are chemically synthesized from readily available starting materials, such as α-amino acids and their finctional equivalents. Modular and convergent methods for the synthesis of these compounds are also preferred. In a convergent approach, for example, large sections of the final product are brought together in the last stages of the synthesis, rather than by incremental addition of small pieces to a growing molecular chain.

Compounds of the invention, $R^3$—L—L'—$R^1$, according to one embodiment, can be represented as $R^3$—$Y^4$—$Y^3$—CH(X)—$Y^1$—$R^1$. This compound can be viewed as a dipeptide derivative: with $R^1$ as an amino acid residue or a derivative thereof; $Y^1$ as an amide linkage, or a derivative thereof, between the two residues; X as a carboxylate or a derivative thereof; C as the α-carbon atom of the second residue; and $R^3$—$Y^4$—$Y^3$— as the side chain of the second residue.

In the general method illustrated below, the compound $R^3$—$Y^4$—$Y^3$—CH(X)—$Y^1$—$R^1$ is prepared by first coupling a properly protected $Y^{4'}$—$Y^3$—CH(X)—$Y^{1'}$ with a properly protected $R^{3'}$. $Y^3$ and X have been defined above. $Y^{4'}$, $Y^{1'}$, and $R^{3'}$ are precursors of $Y^4$, $Y^1$, and $R^3$, respectively.

Compounds of this invention may be synthesized using any conventional technique, several of which are exemplified herein. Preferably, these compounds are chemically synthesized from readily available starting materials, such as α-amino acids and their functional equivalents. Modular and convergent methods for the synthesis of these compounds are also preferred. In a convergent approach, for example, large sections of the final product are brought together in the last stages of the synthesis, rather than by incremental addition of small pieces to a growing molecular chain.

Compounds of the invention, $R^3$—L—L'—$R^1$, according to one embodiment, can be represented as $R^3$—$Y^4$—$Y^3$—CH(X)—$Y^1$—$R^1$. This compound can be viewed as a dipeptide derivative: with $R^1$ as an amino acid residue or a derivative thereof; $Y^1$ as an amide linkage, or a derivative thereof, between the two residues; X as a carboxylate or a derivative thereof; C as the α-carbon atom of the second residue; and $R^3$—$Y^4$—$Y^3$— as the side chain of the second residue.

In the general method illustrated below, the compound $R^3$—$Y^4$—$Y^3$—CH(X)—$Y^1$—$R^1$ is prepared by first coupling a properly protected $Y^{4'}$—$Y^3$—CH(X)—$Y^{1'}$ with a properly protected $R^{3+}$. $Y^3$ and X have been defined above. $Y^{4'}$, $Y^{1'}$, and $R^{3'}$ are precursors of $Y^4$, $Y^1$, and $R^3$, respectively.

Compounds of the formula $Y^{4'}$—$Y^3$—CH(X)—$Y^{1'}$ are available commercially or can be prepared according to methods known one of ordinary skill in the art. For example, if $Y^{1'}$ is an amino group; X is a carboxylate; and $Y^{4'}$—$Y^3$— is $NH_2$—$(CH_2)_3$—, the compound $Y^{4'}$—$Y^3$—CH(X)—$Y^{1'}$ is ornithine. As another example, if $Y^{1'}$ is an amino group, X is carboxylate and $Y^{4'}$—$Y^3$— is 4-$NH_2$-phenyl-$CH_2$—, the compound $Y^{4'}$—$Y^3$—CH(X)—$Y^{1'}$ is 4-aminophenylalanine, available by reduction of commercially available is 4-nitrophenylalanine. Further reduction of the phenyl moiety produces a compound wherein $Y^{1'}$ is an amino group, X is carboxylate and $Y^{4'}$—$Y^3$— is 4-$NH_2$-cyclohexyl-$CH_2$—, or 4-aminocyclohexylalanine, available commnercially as a mixture of cis and trans isomers. As mentioned above, proper protecting groups are required to prevent certain functionalities from undergoing undesired reactions. Using ornithine as an example, $Y^{1'}$ and X are functionalities that are not involved in the first coupling reaction, and should be protected with common amino protecting groups such as carbamates (e.g., t-butyl carbamate (BOC) and benzyl carbamate (CBZ)) and common carboxyl protecting groups such as substituted esters (e.g., ethyl ester and methoxymethyl ester). For more appropriate protecting groups, see T. W. Greene, *Protecting Groups in Organic Synthesis*, John Wiley & Sons, New York, 1981, and references cited therein.

The compound $R^3$ can be represented by the formula $Z^3$—$L^b$—$Z^4$—T or $R^4$—$Y^5$—N($R^5$)—CH($R^6$)—T'. Each of T and T' is a functionality which joins with $Y^{4'}$ to form $Y^4$. For example, if the desired $Y^4$ is an amide linkage, it can be formed by reacting an amine group ($Y^{4'}$) with a carboxyl group (T or T') in the presence of a common coupling reagent such as benzotriazol-1-yloxytris(dimethylamino)-phosphonium hexafluorophosphate (BOP) or O-benzotriazol-1-yl-N,N,N'-tetramethyluronium hexafluorophosphate (HBTU). As another example, if the desired $Y^4$ is an aryl ether, it can be formed by reacting a phenol with an alcohol in the presence of diethylazodicarboxylate (DEAD) and triphenylphosphine.

When $R^{3'}$ is of the formula $Z^3$—$L^b$—$Z^4$—T, the compound is available commercially or can be prepared according to methods known one of ordinary skill in the art. For example, when $Z^3$ is 2-methyl phenyl; $Z^4$ is phenylmethyl; $L^b$ is —NH—CO—NH— and T is —COOH, $R^{3'}$ is o-methylphenyl-ureido-phenyl acetic acid and can be obtained by reaction of 4-aminophenylacetic acid with 2-methylphenyl isocyanate. As another example, when $Z^3$ is 3-indole; $Z^4$ is phenylmethyl; $L^b$ is —CO—NH— and T is —COOH, $R^{3'}$ is 3-indolecarboxamido-phenyl acetic acid and can be obtained by reaction of 4-aminophenylacetic acid with indole-3-carbonyl chloride.

When $R^{3'}$ is of the formula $R^4$—$Y^5$—N($R^5$)—CH($R^6$)—T', $Y^{4'}$—$Y^3$—CH(X)—$Y^{1'}$ can couple to NH($R^5$)—CH($R^6$)—T' to form the intermediate NH($R^5$)—CH($R^6$)—$Y^4$—$Y^3$—CH(X)—$Y^{1'}$ prior to further coupling to $R^4$—$Y^{5'}$ to form $R^4$—$Y^5$—N($R^5$)—CH($R^6$)—$Y^4$—$Y^3$—CH(X)—$Y^{1'}$. $Y^{5'}$ is a functionality which, upon undergoing further cou pling reactions, gives rise to the functionality $Y^5$. Note that the compound $NH(R^5)$—$CH(R^6)$—T' can be an amino acid derivative which is commercially available and can be prepared using conventional methods by one of ordinary skill in the art. For example, when T' is carboxyl; $R^6$ is isobutyl; and $R^5$ is methyl, the compound $NH(R^5)$—$CH(R^6)$—T' is N-methylleucine. $R^4$—$Y^{5'}$ can be coupled to $NH(R^5)$—$CH(R^6)$—$Y^4$—$Y^3$—$CH(X)$—$Y^{1'}$ by commonly used synthetic methods. For example, if $Y^{5'}$ is carboxyl, the resulting $Y^5$ is an amide linkage and can be prepared using common peptide synthesis reagents as mentioned above. As another example, if $Y^{5'}$ is an halide or sulfonate the resulting $Y^5$ is a secondary or tertiary amine resulting from alkylation of the starting amine. Alternatively, to form the compound $R^4$—$Y^5$—$N(R^5)$—$CH(R^6)$—$Y^4$—$Y^3$—$CH(X)$—$Y^{1'}$, $NH(R^5)$—$CH(R^6)$—T' can first couple to $R^4$—$Y^{5'}$ to form the intermediate $R^4$—$Y^5$—$N(R^5)$—$CH(R^6)$—T' prior to further coupling to $Y^{4'}$—$Y^3$—$CH(X)$—$Y^{1'}$. Example 1 below provides a detailed procedure wherein $R^{3'}$— is of the formula $R^4$—$Y^5$—$N(R^5)$—$CH(R^6)$—.

Alternatively, when $R^{3'}$ is of the formula $Z^3$—$L^b$—$Z^4$—T, it can react with $Y^{4'}$—$Y^3$—$CH(X)$—$Y^{1'}$ to form $Z^3$—$L^b$—$Z^4$—$Y^4Y^3$—$CH(X)$—$Y^1$. See Example 2.

The final product $R^3$—$Y^4$—$Y^3$—$CH(X)$—$Y^{1'}$ can then be formed by reacting either $R^4$—$Y^5$—$N(R^5)$—$CH(R^6)$—$Y^4$—$Y^3$—$CH(X)$—$Y^{1'}$ or $Z^3$—$L^b$—$Z^4$—$Y^4$—$Y^3$—$CH(X)$—$Y^{1'}$ with $R^{1'}$ (the precursor of R1). The moiety $Y^1$ can be formed in a similar manner as $Y^4$.

A cell adhesion inhibitor of the invention can be purified by conventional methods such as chromatography or crystallization.

Set forth below are five general methods for preparing a compound of this invention.

General Method A

Solid-Phase Preparation of Diaminopropionate Derivatives:

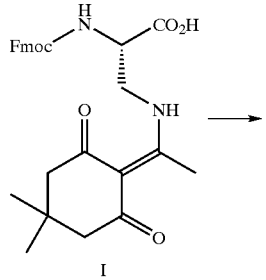

I

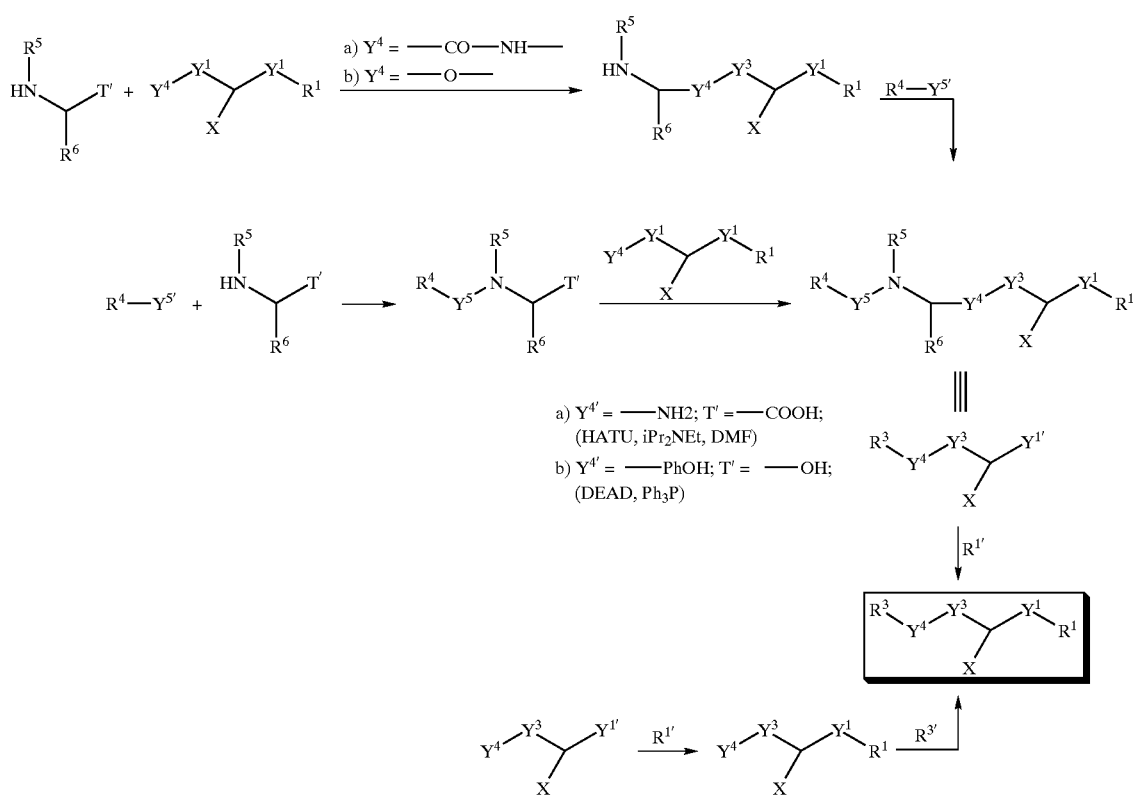

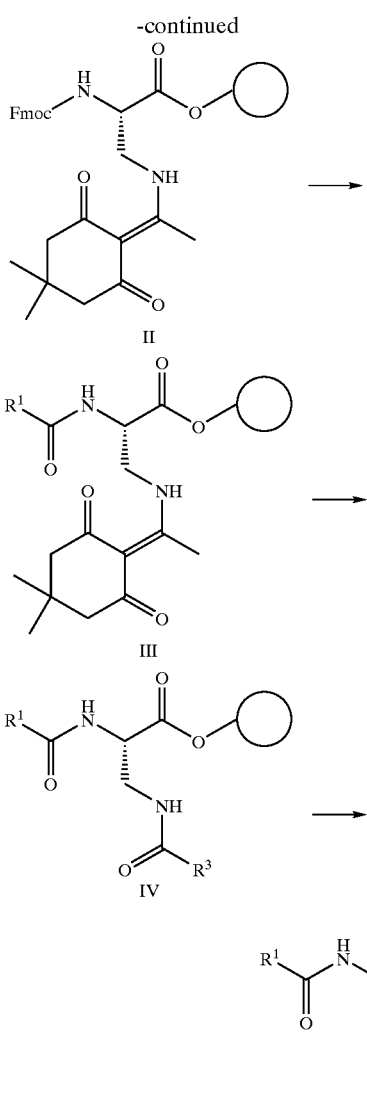

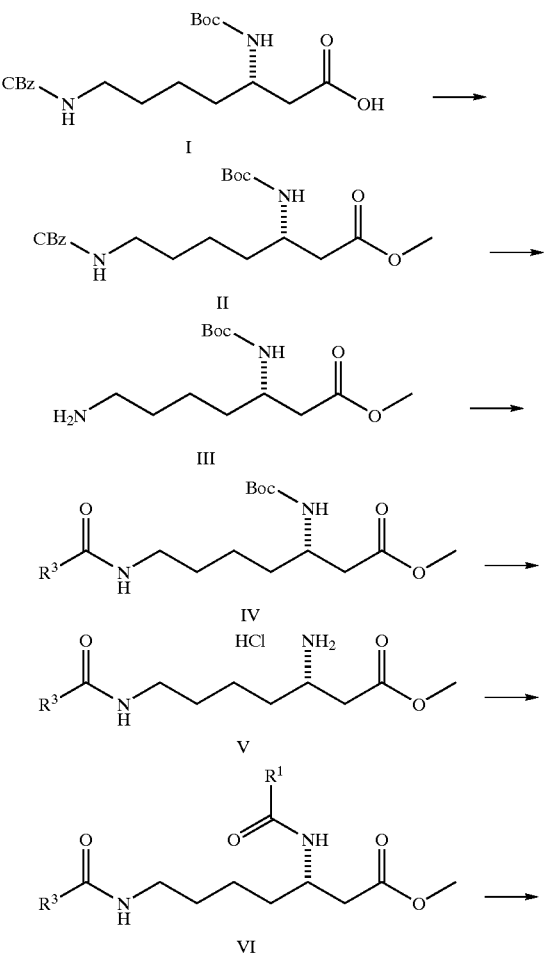

dichloromethane. If $R^1CO2H$ is an Fmoc protected amino acid, the deprotection and acylation are repeated as described above.

Deprotection and Acylation of N-β: The acylated diaminopropionate resin, III, was treated with 2% hydrazine in DMF for 1 h, after which it was filtered and washed with DMF and dichloromethane. The deprotected resin was immediately acylated by treatment with $R^3CO_2H$ (2 eq), HATU (2 eq) and diisopropylethylamine (4 eq). The reactions were shaken for 2 h, filtered and the acylation was repeated. The resin was filtered and washed with DMF and dichloromethane.

Cleavage of Final Product from Resin: The diacyl diaminopropionate resin, IV, was treated with 95% TFA/5% water for 1 h. The solvent was removed by filtration and the resin was washed with two small protions of TFA. The combined TFA solutions were concentrated under vacuum and the resulting residue was purified by revere-phase hplc yielding pure diacyldiarninopropionate derivatives.

General Method B

Preparation of beta-Lysine Derivatives:

Orthogonally Fmoc/Dde Protected Wang Resin (II): S—N-α-Fmoc-N-β-Dde-diaminopropionic acid, I (4.95 g, 10.1 mmol), was attached to Wang resin (7.88 g, 0.64 mmol/g, 100–200 mesh) by reaction with 2,6-dichlorobenzoyl chloride (1.45 mL, 10.1 mmol) and dry pyridine (1.35 mL) in 40 mL dry DMF. The mixture was shaken for 16 h at room temperature. The resin was isolated by filtration and was washed three times each with DMF and dichioromethane. The resin was capped by reaction with dichiorobenzoyl chloride and pyridine (2 mL each) for 2 h followed by washing as above. The resulting resin contained 0.64 mmol/g Fmoc as determined by piperidine treatment and measurement of $A_{290}$.

Deprotection and Acylation of N-α: The diaminopropionate resin, II, was treated with 20% piperidine in DMF for 15 min after which it was filtered and washed with DMF and dichloromethane. The deprotected resin was immediately acylated by treatment with $R^1CO_2H$ (2 eq), HATU (2 eq) and diisopropylethylamine (4 eq). The reactions were shaken for 2 h, filtered and the acylation was repeated. Completion of acylation was determined by a negative Kaiser test. The resin was filtered and washed with DMF and

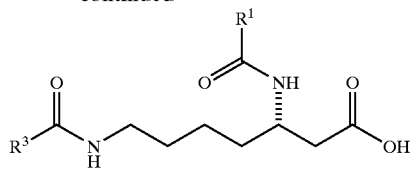

Omega-N-Cbz-beta-N-BOC-beta-homolysine Methyl Ester (II): Omega-N-Cbz-beta-N-BOC-beta-homolysine, I, was dissolved in N,N-dimethylformamide. To this solution was added sodium bicarbonate (10 equivalents) and then iodomethane (6 equivalents) with stirring. After stirring overnight at room temperature, the reaction mixture was partitioned between water and ethyl acetate. The organic layer was washed with saturated sodium chloride solution, then dried over sodium sulfate. Filtering and evaporation of the solvent was followed by silica gel chromatography (hexane/ethyl acetate) to yield ester II.

Beta-N-BOC-beta-homolysine Methyl Ester (III): N-Cbz carbamate II was dissolved in methanol. To this was added 10% palladium on carbon. The mixture was flushed with nitrogen, then hydrogen (50 psi) was added. After stirring overnight, the catalyst was removed using a Whatman PTFE filter and the solution was concentrated to yield crude amine III.

N-omega Acylation: Amine III (111 mg), 2-(1H-benzotriazole-1-yl)-1,1,3,3-tetramethyluronium hexafluorophosphate (HBTU, 1.1 equivalents) and $R^1CO_2H$ (1.1 equivalents) were dissolved in N,N-dimethylformamide. To this solution was added N,N-diisopropylethylamine (2.5 equivalents). After stirring overnight, the reaction was quenched with 5% aqueous citric acid solution, then extracted with ethyl acetate. The organics were washed with saturated sodium chloride solution, then dried over sodium sulfate. Filtration and removal of the solvent by rotary evaporation yielded crude amide IV, which was used without further purification.

N-beta Deprotection and Acylation: Crude N-BOC carbamate IV was treated with saturated hydrogen chloride in ethyl acetate, prepared by bubbling hydrogen chloride gas through cold (zero degree) ethyl acetate solution for 30 minutes. The reaction was stirred for one hour, then concentrated to dryness to yield crude amine V, which was used without further purification. Crude amine V was dissolved in N,N-dimethylformamide along with $R^3CO_2H$ (1 equivalent) and HBTU (1.1 equivalent). With stirring was added N,N-diisopropylethylamine (7.5 equivalents). After stirring overnight, the reaction was partitioned between 5% aqueous citric acid and ethyl acetate. The organic layer was washed with saturated sodium chloride solution, then dried over sodium sulfate. Filtration of the drying agent and evaporation of the solvent gave crude amide VI, which was used without further purification.

Final Deprotecton: Methyl ester VI was dissolved in 1:1 tetrahydrofuran and methanol. With stirring was added aqueous lithium hydroxide (2 N). After stirring for one hour, the reaction mixture was concentrated to dryness. The residue was partitioned between 1 N aqueous hydrogen chloride and ethyl acetate, and the organic layer was washed with saturated sodium chloride. Drying over sodium sulfate, filtering and evaporating gave crude acid. Purification by preparative reverse-phase high performance liquid chromatography gave pure acid.

General Method C

Solid-Phase Preparation of Lysine Derivatives:

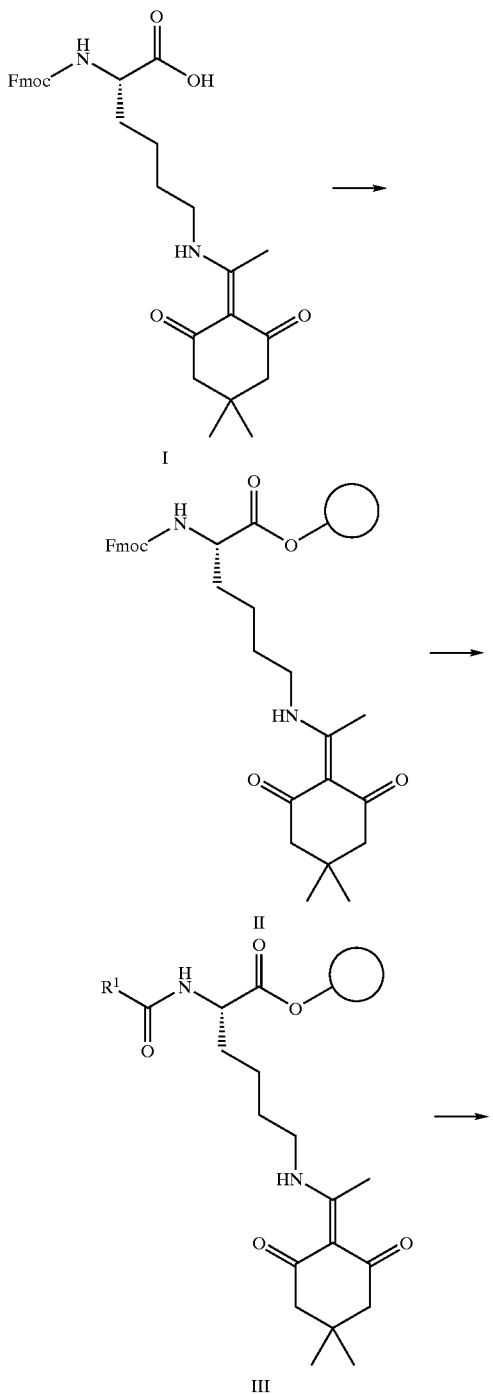

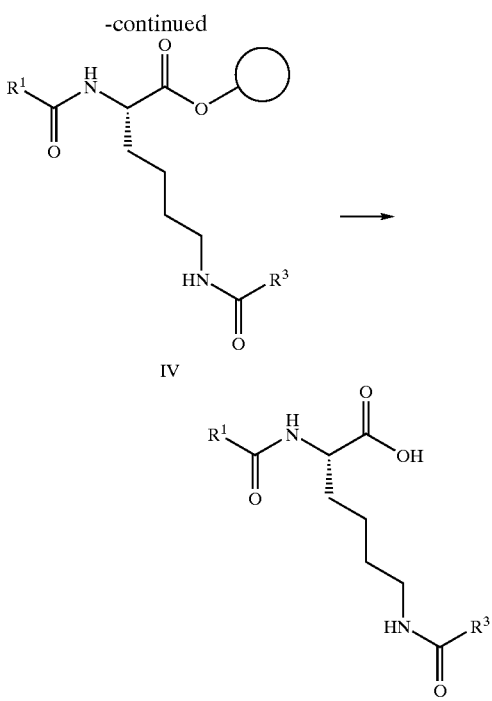

Fmoc/Dde Lysine Wang Resin (II): N-α-Fmoc-N-β-Dde-Lysine, 1 (5.0 g, 9.39 mmol), was attached to Wang resin (7.34 g, 0.64 mmol/g, 100–200 mesh) by reaction with 2,6-dichlorobenzoyl chloride (1.33 mL, 10.1 mmol) and dry pyridine (1.27 mL) in 50 mL dry DMF. The mixture was shaken for 16 h at room temperature. The resin was isolated by filtration and was washed three times each with DMF and dichloromethane. The resin was capped by reaction with dichlorobenzoyl chloride and pyridine (2 mL each) for 2 h followed by washing as above. The resulting resin contained 0.56 mmol/g Fmoc as determined by piperidine treatment and measurement of $A_{290}$.

Deprotection and Acylation of N-α: The diaminopropionate resin, II, was treated with 20% piperidine in DMF for 15 min after which it was filtered and washed with DMF and dichloromethane. The deprotected resin was immediately acylated by treatment with $R^1CO_2H$ (2 eq), HATU (2 eq) and diisopropylethylamine (4 eq). The reactions were shaken for 2 h, filtered and the acylation was repeated. Completion of acylation was determnined by a negative Kaiser test. The resin was filtered and washed with DMF and dichloromethane. If $R^1CO_2H$ is an Fmoc protected amino acid, the deprotection and acylation are repeated as described above.

Deprotection and Acylation of N-β: The acylated lysine resin, III was treated with 2% hydrazine in DMF for 1 h, after which it was filtered and washed with DMF and dichloromethane. The deprotected resin was immediately acylated by treatment with $R^3CO_2H$ (2 eq), HATU (2 eq) and diisopropylethylamine (4 eq). The reactions were shaken for 2 h, filtered and the acylation was repeated. The resin was filtered and washed with DMF and dichloromethane.

Cleavage of Final Product from Resin: The diacyl lysine resin, IV, was treated with 95% TFA/5% water for 1 h. The solvent was removed by filtration and the resin was washed with two small protions of TFA. The combined TFA solutions were concentrated under vacuum and the resulting residue was purified by revere-phase HPLC yielding pure diacyllysine derivatives.

General Method D

Preparation of oMePUPA-N-MeLeu-α,γ-diaminobutyric Acid Derivatives:

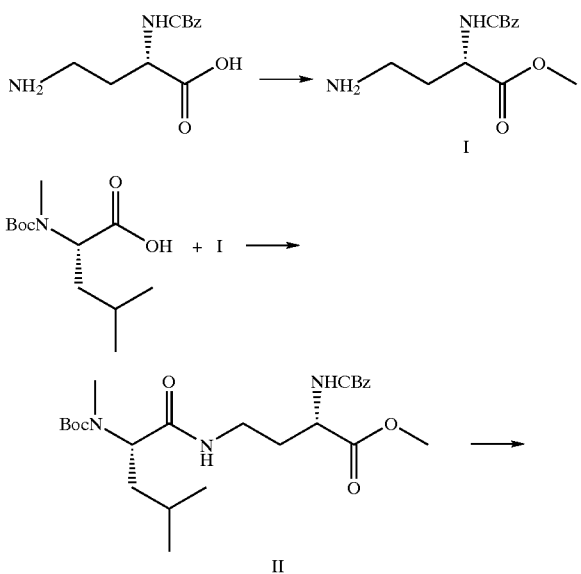

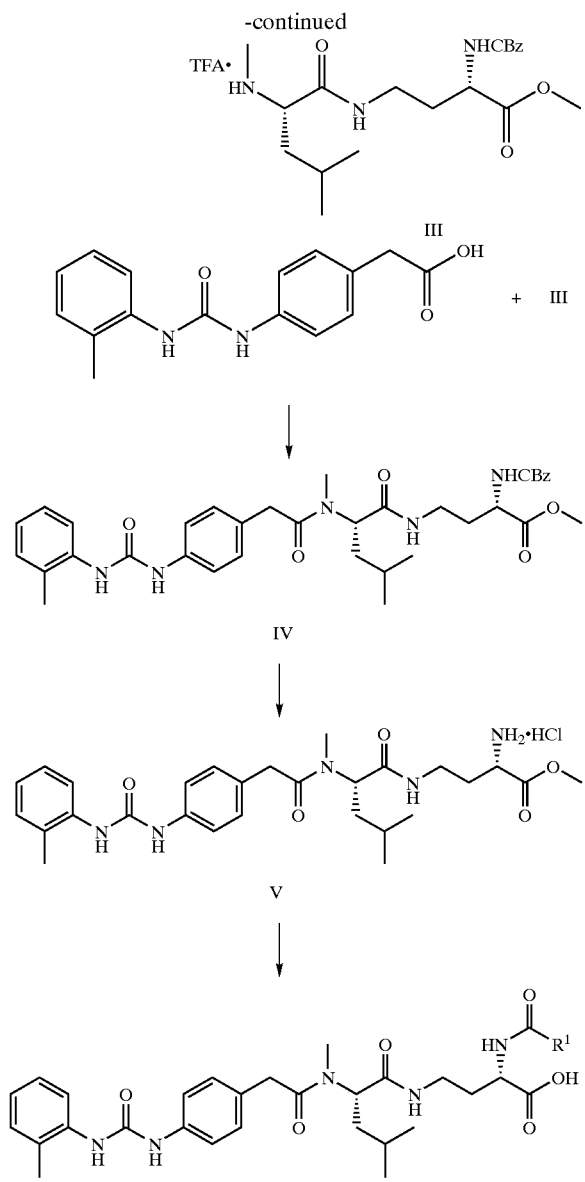

N-α-CBZ-L-2,4-diaminobutyric acid methyl ester hydrochloride (I): In a 500 mL RB flask was suspended 8.4 g (33.3 mmol) N-α-CBZ-L-2,4-diaminobutyric acid in 200 mL methanol with stirring. This was cooled to 0° C. (ice bath), and then 14.6 mL (200 mmol) $SOCl_2$ was added dropwise over 15 minutes to give a colorless solution. The solution was allowed to warmn to RT and stirred overnight. The solution was concentrated, redissolved in MeOH and concentrated 2×, then dissolved in $CH_2Cl_2$, concentrated, and placed under high vacuum for 16 hours to give compound I as a slightly yellow foam, massing to 10.33 g (34.2 mmol, 103%). M/z=267.1 (M+H$^+$).

BOC-N-methyl-Leucinyl-(N-α-CBZ)-GABA methyl ester (II): In a 500 mL RB flask was dissolved 10.33 g (33.3 mmol) of I (MW=302) in 100 mL dry dimethylformamide (DMF) with stirring to give a colorless solution. To this was added 17.4 mL (100 mmol) of diisopropylethylamine (DIEA), then 7.96 g (32.5 mmol) of Boc-N—Me-Leucine, and finally 14.83 g (39.0 mmol) of O-(7-azabenzotriazol-1-yl)-1,1,3,3-tetramethyluronium hexafluorophosphate (HATU) to give a yellow solution. This was stirred overnight, after which HPLC showed no starting material. The solution was diluted with ethyl acetate (EtOAc, 500 mL) and washed with 1N HCl (2×), 1N NaOH (2×), and brine (1×). The organic phase was dried over anhydrous $MgSO_4$, filtered, and concentrated to a red oil. Chromatography with 2:1 hexanes/EtOAc vs. silica gave 12.56 g (25.5 mmol, 78%) of II ($R_f$=0.46 with 1:1 Hex/EtOAc vs. silica) as a yellow syrup (HPLC, >99%). M/z=494.3 (M+H$^+$).

H—N-methyl-Leucinyl-(N-αCBZ)-GABA methyl ester trifluoroacetate salt (III): In a 50 mL RB flask was dissolved 0.50 g (1.01 mmol) of II (MW=493) in 10 mL $CH_2Cl_2$ with stirring to give a colorless solution. To this was added 2 mL (26 mmol, large excess) of trifluoroacetic acid and the resulting solution was stirred for four hours, after which HPLC showed no starting material. The solution was concentrated, redissolved in $CH_2Cl_2$ and concentrated (2×), then placed under high vacuum overnight to give 0.52 g (~quantitative) of III as a very pale yellow oil. M/z=394.4 (M+H⁺). Material carried through.

oMePUPA-N-methyl-Leucinyl-(N-α-CBZ)-GABA methyl ester (EV): In a 10 mL vial was dissolved 0.52 g (1.01 mmol) of III (MW=507) in 5 mL DMF with stirring to give a pale yellow solution. To this was added 525 μL (3.0 mmol) of DIEA, then 284 mg (1.0 mmol) of oMePUPA free acid (Ricerca; MW=284), and finally 0.42 g (1.1 mmol) of HATU to give a yellow solution. This was stirred overnight, after which HPLC showed no starting material remaining. The solution was diluted with EtOAc (75 mL) and washed with 1N HCl (3×), 1N NaOH (3×), and brine (1×). The organic phase was dried with MgSO₄, filtered, and the filtrate concentrated to a yellow oil/solid mixture. Chromatography with 1:2 acetonitrile/CH₂Cl₂ vs. silica gave 0.49 g (0.74 mmol, 74%) of VI ($R_f$=0.56 with 1:1 acetonitrile/CH₂Cl₂ vs. silica) as a bright white, foamy solid (HPLC, >99%). M/z=660.1 (M+H⁺).

oMePUPA-N-methyl-Leucinyl-(N-α-H)-GABA methyl ester Hydrochloride (V): In an 85 mL high-pressure vessel was dissolved 400 mg (0.61 mmol) of IV (MW=659) in 10 mL MeOH with stirring to give a colorless solution. The vessel was flushed with nitrogen, and 50 mg (catalytic) of 10% palladium on carbon was added. The sides of the vessel were washed with additional MeOH, and the vessel capped with a hydrogenation head. The vessel was charged with 60 psi H₂ and the mixture stirred overnight, after which the vessel was purged to ambient atmosphere. The mixture was filtered through Celite 545, the filter pad washed with additional (10 mL) MeOH, and the filtrate concentrated. The residue was dissolved in minimal (2 mL) MeOH and dripped into ice-cold 1.0M HCl in diethyl ether to give a white precipitate. The solid was triturated in the HCl/ether for 20 minutes, then filtered, the solid washed with ether, and air-dried for one hour. The white solid was then crushed into a powder with a spatula, washed with additional ether, and air-dried overnight to give 336 mg (0.60 mmol, 98%) of V as a white powder (HPLC, >99%). ESMS m/z=526.6 (M+H⁺).

Acylation and final hydrolysis: Crude amine V was dissolved in N,N-dimethylformamide along with R³CO₂H (1 equivalent) and HBTU (1.1 equivalent). With stirring was added N,N-diisopropylethylamine (4 equivalents). After stirring overnight, the reaction was partitioned between 5% aqueous citric acid and ethyl acetate. The organic layer was washed with saturated sodium chloride solution, then dried over sodium sulfate. Filtration of the drying agent and evaporation of the solvent gave crude amide, which could be purified by reverse-phase hplc. Methyl ester was dissolved in 1:1 tetrahydrofuran and methanol. With stirring was added aqueous lithium hydroxide (2 N). After stirring for one hour, the reaction mixture was concentrated to dryness. The residue was partitioned between 1 N aqueous hydrogen chloride and ethyl acetate, and the organic layer was washed with saturated sodium chloride. Drying over sodium sulfate, filtering and evaporating gave crude acid. Purification by preparative reverse-phase high performance liquid chromatography gave pure product.

General Method E

Solution-Phase Synthesis from Diamino Acids:

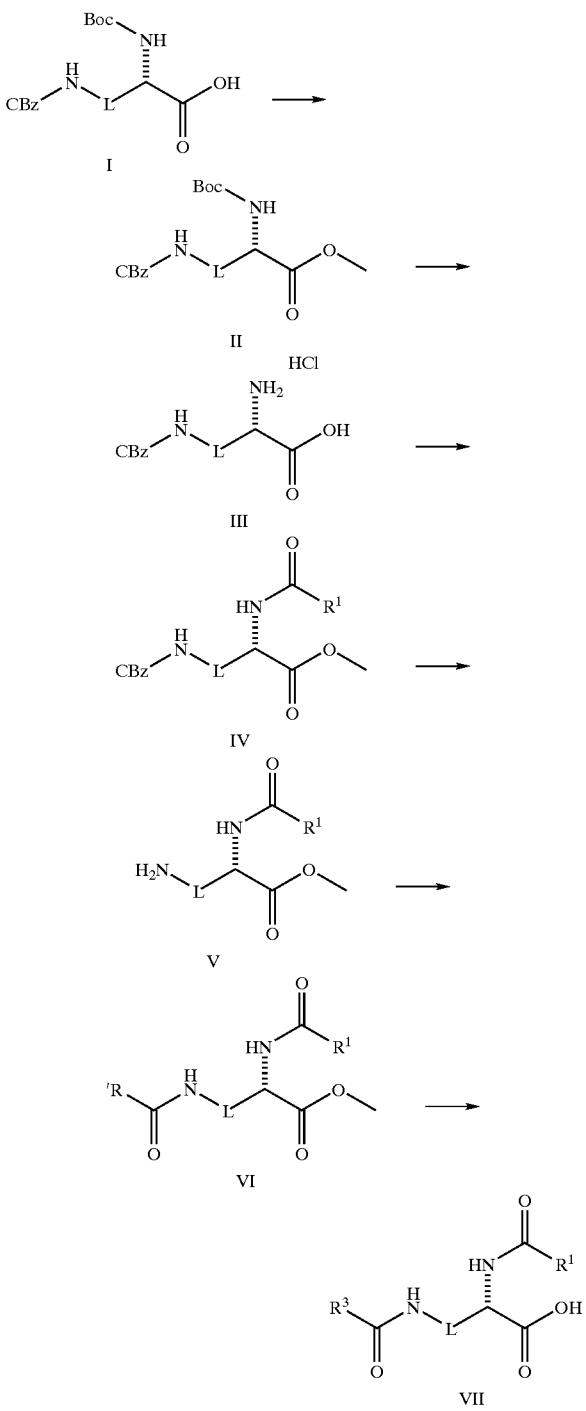

The orthogonally N-alpha-Boc/Cbz protected diamine, I, was converted to methyl ester II by reaction with methyl iodide (5 eq) and potassium carbonate (5 eq) in acetone at room temperature for 16 h. The reaction mixture was diluted with water and extracted with ethyl acetate. The organics were washed with water, saturated sodium bicarbonate and brine, dried over sodium sulfate and filtered. Product was eluted through silica in ethyl acetate and hexanes.

N-alpha deprotection and acylation: The fully protected diamine, II, was dissolved in 3N Hcl in EtOAc and was stirred 1 h at room temperature. The solution was concentrated under reduced pressure. The resulting solid was suspended in diethyl ether, isolated by filtration, washed with ether and dried under vacuum. The hydrochloride, III, thus isolated was treated with HATU (1.25 eq), diisopropylethylamine (4 eq) and $R^1CO_2H$ (1.25 eq) in dry DMF, and was stirred under nitrogen for 16 h. The reaction mixture was diluted with 5% citric acid and was extracted with EtOAc. The organics were washed with water, saturated sodium bicarbonate and brine, dried over sodium sulfate and filtered. The solution was concentrated under reduced pressure and the residue was purified by elution through silica in EtOAc and hexane, providing pure product, IV.

Distal nitrogen deprotection and acylation: The CBz protected intermediate, IV, was dissolved in methanol and was degassed. 10% Pd on activated carbon was added and the mixture was stirred under 60 psi hydrogen for 3 to 16 h. The reaction was filtered and concentrated. The resulting free amine was immediately acylated by reacting with HATU (1.25 eq), diisopropylethylamine (4 eq) and $R^3CO_2H$ (1.25 eq) in dry DMF, with stirring under nitrogen for 16 h. The reaction mixture was diluted with 5% citric acid and was extracted with EtOAc. The organics were washed with water, saturated sodium bicarbonate and brine, dried over sodium sulfate and filtered. The product, VI, was purified by elution through silica in ethyl acetate and hexane.

Hydrolysis to final product: The methyl ester VI was dissolved in 1:1 tetrahydrofuran and methanol. With stirring was added aqueous lithium hydroxide (2 N). After stirring for one hour, the reaction mixture was concentrated to dryness. The residue was partitioned between 1 N aqueous hydrogen chloride and ethyl acetate, and the organic layer was washed with saturated sodium chloride. Drying over sodium sulfate, filtering and evaporating gave crude acid. Purification by preparative reverse-phase high performance liquid chromatography gave pure acid VII.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

Also included are non-classical isoteres such as $CO_2H$, $SO_2NHR$, $SO_3H$, $PO(OH)NH_2$, $PO(OH)OEt$, $CONHCN$,

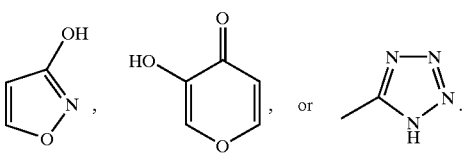

Once synthesized, the activities and VLA-4 specificities of the compounds according to this invention may be determined using in vitro and in vivo assays.

For example, the cell adhesion inhibitory activity of these compounds may be measured by determining the concentration of inhibitor required to block the binding of VLA-4-expressing cells to fibronectin- or CS1-coated plates. In this assay microtiter wells are coated with either fibronectin (containing the CS-1 sequence) or CS-1. If CS-1 is used, it must be conjugated to a carrier protein, such as bovine serum albumin, in order to bind to the wells. Once the wells are coated, varying concentrations of the test compound are then added together with appropriately labelled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, as well as human peripheral blood lymophocytes (PBLs). The cells used in this assay may be fluorescently or radioactively labelled.

A direct binding assay may also be employed to quantitate the inhibitory activity of the compounds of this invention. In this assay, a VCAM-IgG fuision protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, the disclosure of which is herein incorporated by reference. The conjugation of that fusion to a marker enzyme is achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature.

Following incubation, the wells are vacuum drained, leaving behind the cells and any bound VCAM. Quantitation of bound VCAM is determined by adding an appropriate calorimetric substrate for the enzyme conjugated to VCAM-IgG and determining the amount of reaction product. Decreased reaction product indicates increased binding inhibitory activity.

In order to assess the VLA-4 inhibitory specificity of the compounds of this invention, assays for other major groups of integrins, i.e., β2 and β3, as well as other β1 integrins, such as VLA-5, VLA-6 and α4β7 are performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. α4β7 is a recently discovered homologue of VLA-4, which also binds fibronectin and VCAM. Specificity with respect to α4β7 is determined in a binding assay that utilizes the above-described VCAM-IgG-enzyme marker conjugate and a cell line that expresses α4β7, but not VLA-4, such as RPMI-8866 cells.

Once VLA-4-specific inhibitors are identified, they may be further characterized in in vivo assays. One such assay tests the inhibition of contact hypersensitivity in an animal, such as described by P. L. Chisholm et al., "Monoclonal Antibodies to the Integrin α-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), the disclosures of which is herein incorporated by reference. In this assay, the skin of the animal is sensitized by exposure to an irritant, such as dinitrofluorobenzene, followed by light physical irritation, such as scratching the skin lightly with a sharp edge. Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear. Swelling is measured using calipers or other suitable instrument to measure ear thickness. In this manner, one may identify those inhibitors of this invention which are best suited for inhibiting inflammation.

Another in vivo assay that may be employed to test the inhibitors of this invention is the sheep asthma assay. This assay is performed essentially as described in W. M. Abraham et al., "α-Integrins Mediate Antigen-induced Late Bronchial Responses and Prolonged Airway Hyperresponsiveness in Sheep", *J. Clin. Invest.*, 93, pp. 776–87 (1994), the disclosure of which is herein incorporated by reference. This assay measures inhibition of Ascaris antigen-induced late phase airway responses and airway hyperresponsiveness in asthmatic sheep.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions.

In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

As stated above, an effective amount of a pharmaceutical composition containing an effective amount of a compound of this invention is also within the scope of this invention. An effective amount is defined as the amount which is required to confer a therapeutic effect on the treated patient, and will depend on a variety of factors, such as the nature of the inhibitor, the size of the patient, the goal of the treatment, the nature of the pathology to be treated, the specific pharmaceutical composition used, and the judgment of the treating physician. For reference, see Freireich et al., Cancer Chemother. Rep. 1966, 50, 219 and Scientific Tables, Geigy Pharmaceuticals, Ardley, N.Y., 1970, 537. Dosage levels of between about 0.001 and about 100 mg/kg body weight per day, preferably between about 0.1 and about 10 mg/kg body weight per day of the active ingredient compound are useful.

According to another embodiment compositions containing a compound of this invention may also comprise an additional agent selected from the group consisting of corticosteroids, bronchodilators, antiasthmatics (mast cell stabilizers), antiinflammatories, antirheumatics, immunosuppressants, antimetabolites, immunonodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); and interferons (immunomodulators).

According to other embodiments, the invention provides methods for preventing, inhibiting or suppressing cell adhesion-associated inflammation and cell adhesion-associated immune or autoimmune responses. VLA4- associated cell adhesion plays a central role in a variety of inflammation, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

In order that this invention may be more fully understood, the following examples are set forth. These examples are for the purpose of illustration only and are not to be construed as limiting the scope of the invention in any way.

Intermediate 1

4-(2-methylphenylaminocarbonylamino)phenylacetic Acid (oMePUPA-OH): To a suspension of p-aminophenylacetic acid (56.8 g, 376 mmol) in DMS (150 mL) was added o-tolyl isocyanate (50 g, 376 mmol) dropwise. The reaction mixture was allowed to stir 1 h, and was poured into EtOAc (1.75 L) with stirring. The precipitate was collected and washed with EtOAc (400 mL) and MeCN (400 mL) to provide oMePUPA (80 g, 75%). ESMS m/z (M+H$^+$) 285.1.

Intermediate 2

OMePUPA-Leu-OH: oMePUPA-OH (0.78 g) was combined with Leucine methyl ester hydrochloride (0.50 g, 1.0 eq), HATU (1.10 g, 1.05 eq), and diisopropylethylamine (1.9 mL, 4 eq) in 10 mL dry DMF. The reaction was stirred for 16 h at room temperature after which it was diluted with 50 mL EtOAc, which was washed with 5% citric acid, water, saturated sodium bicarbonate and brine. The resulting organic solution was dried over sodium sulfate filtered and concentrated to yield 1.13 g of white solid. This product was dissolved in 10 mL THF. 5 mL 2N LiOH was added and the reaction was stirred for 16 h. THF was removed under reduced pressure and the solution was diluted with 40 mL water and washed with EtOAc. The aqueous layer was acidified with 1N HCl and was extracted with EtOAc. The organic extracts were washed with dilute HCl and brine, were dried over sodium sulfate, filtered and concentrated under reduced pressure yielding 0.77 g of white solid. ESMS m/z (M+H$^+$) 398.5.

Intermediate 3

N-(3,5-diChlorobenzenesulfonyl)-Proline Methyl Ester: To a solution of 24.8 g (0.15 mol) of L-Proline methyl ester hydrochloride in 500 mL of CH$_2$Cl$_2$ was added 70 mL (0.5 mol) of triethylamine with stirring to give copious white precipitate. The mixture was filtered, and the filtrate cooled to 0° C. (ice bath) with stirring. To the cooled solution was added a solution of 36.8 g (0.15 mol) of 3,5-dichlorobenzenesulfonyl chloride in 70 mL of CH$_2$Cl$_2$ dropwise quickly over five minutes. The addition funnel was rinsed with an additional 30 mL of CH$_2$Cl$_2$, and the cloudy yellow mixture was allowed to warm to room temperature with stirring overnight. The mixture was washed 2× with 400 mL of 1N HCl, 2× with 400 mL of 1N NaOH, then brine, then dried (MgSO$_4$), filtered, and concentrated to a yellow oil which crystallized on standing. The material was recrystallized three times from ethyl acetate/hexanes to give 39.3 g (0.116 mol, 77%) of N-(3,5-dichlorobenzenesulfonyl)-Proline methyl ester (MW=338) as white needles (TLC on silica vs. 2:1 hexanes/ethyl acetate, R$_f$=0.51). M/z=339.3 (M+H$^+$).

N-(3,5-diChlorobenzenesulfonyl)-Proline; To a solution of 39.3 g (0.116 mol) of the above methyl ester in 250 mL methanol was added 115 mL (0.23 mol) of freshly-prepared 2M aqueous LiOH with stirring to give a colorless solution. This was stirred for three hours, after which HPLC showed no starting material. The solution was reduced by 50% in vacuo and partitioned between 1N HCl and CH$_2$Cl$_2$ (200 mL each). The phases were separated and the aqueous layer was washed again with CH$_2$Cl$_2$. The organic phases were combined, dried (MgSO$_4$), and concentrated to a white, foamy solid. This was recrystallized twice from ethyl acetate/hexanes to give 33.8 g (0.104 mol, 90%) of the title compound as colorless, broad, flat needles. M/z=325.2 (M+H$^+$).

Intermediate 4

N-(benzenesulfonyl)-Proline Methyl Ester: To a solution of 25 g (0.15 mol) of L-Proline methyl ester hydrochloride in 500 mL of CH$_2$Cl$_2$ was added 70 mL (0.5 mol) of triethylamine with stirring to give copious white precipitate. The mixture was filtered and the filtrate cooled to 0° C. (ice bath) with stirring. To the cooled solution was added a solution of 20 mL (0.15 mol) of benzenesulfonyl chloride in 50 mL of CH$_2$Cl$_2$ dropwise over fifteen minutes. The addition funnel was rinsed with an additional 25 mL of CH$_2$Cl$_2$, and the cloudy, colorless mixture was allowed to warm to room temperature with stirring overnight. The solution was washed 2× with 400 mL of 1N HCl, 2× with 400 mL of 1N NaOH, 1× with brine, then dried (MgSO$_4$), filtered, and concentrated to a pale yellow solid. This material was recrystallized three times from ethyl acetate/hexanes to give 38.2 g (0.142 mol, 95%) of N-(benzenesulfonyl)-Proline methyl ester (MW=269) as broad white needles (TLC vs. 2:1 hexanes/ethyl acetate, R$_f$=0.35). M/z=270.2 (M+H$^+$).

N-(benzenesulfonyl)-Proline: To a solution of 38.2 g (0.142 mol) of the above methyl ester in 500 mL methanol was added 140 mL (0.28 mol) of freshly-prepared 2M aqueous LiOH with stirring to give a colorless solution. This was stirred overnight, after which HPLC showed no starting material. The solution was reduced by 50% in vacuo and partitioned between 1N HCl and CH$_2$Cl$_2$ (200 mL each). The phases were separated and the aqueous layer was washed again with CH$_2$Cl$_2$. The organic phases were combined, dried (MgSO$_4$), and concentrated to a white solid. This was recrystallized twice from ethyl acetate/hexanes to give 34.7 g (0.136 mol, 96%) of the title compound as fine white needles. M/z=256.2 (M+H$^+$).

EXAMPLE 1
Synthesis of Compound IX
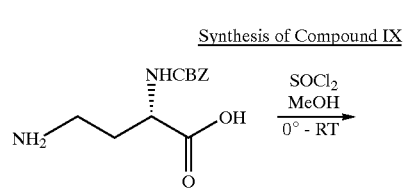
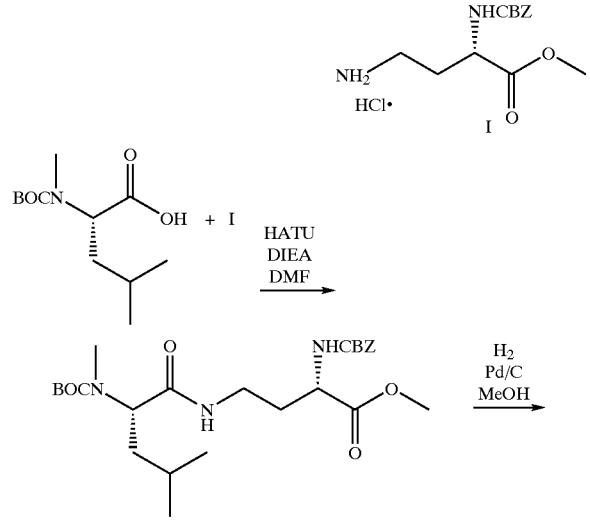
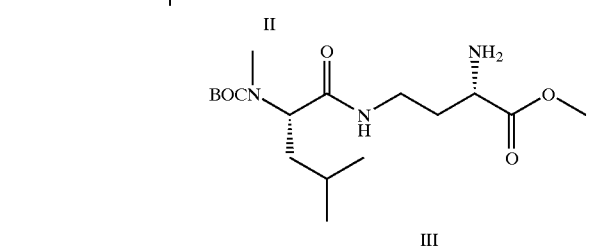
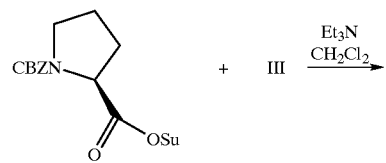
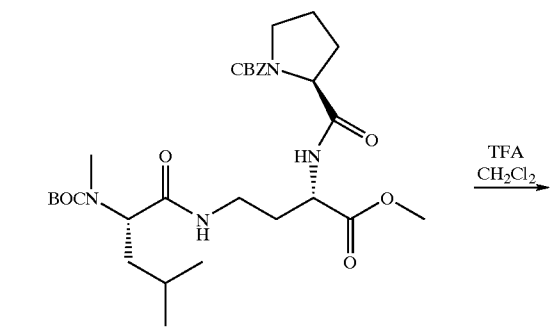
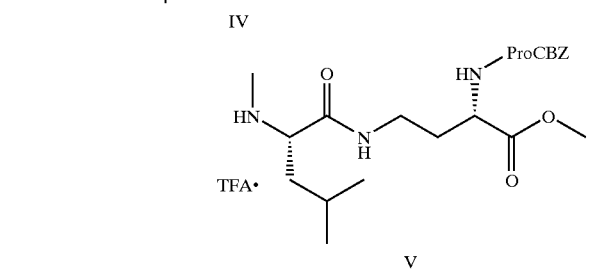
-continued
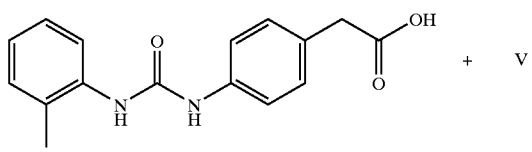
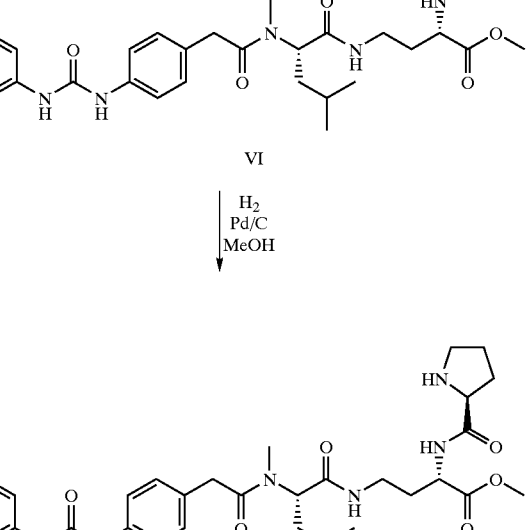
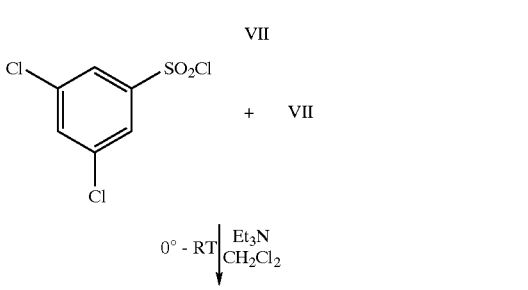
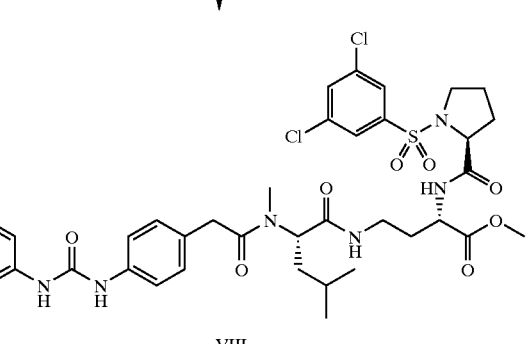
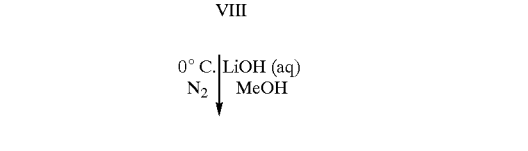

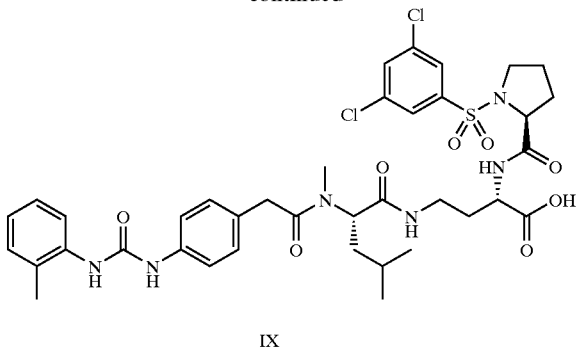

IX

Methyl ester Hydrochloride I: In a 500 mL RB flask was suspended 8.4 g (33.3 mmnol) 2-N-CBZ-L-2,4-diaminobutyric acid in 200 mL methanol (MeOH) with stirring. This was cooled to 0 degrees C. (ice bath), and then 14.6 mL (200 mmol) $SOCl_2$ was added dropwise over 15 minutes to give a colorless solution. The solution was allowed to warm to RT and stirred overnight, after which a proton NMR spectrum of an aliquot indicated the reaction was complete. The solution was concentrated, redissolved in MeOH and concentrated 2×, then dissolved in $CH_2Cl_2$, conc., and placed under high vacuum for 16 hours to give compound I as a slightly yellow foam, massing to 10.33 g (34.2 mmol, 103%). MS: m/z 267 $(M+H)^+$.

tert-Butoxycarbonyl methyl ester II: In a 500 mL RB flask was dissolved 10.33 g (33.3 mmol) of I in dry dimethylformamide (DMF) with stirring to give a colorless solution. To this was added 17.4 mL (100 mmol) of diisopropylethylamine (DIEA), then 7.96 g (32.5 mmol) of Boc-N-Methyl-Leucine, and finally 14.83 g (39.0 mmol) of O-(7-azabenzotriazol-1-yl)-1,1,3,3-tetramethyluronium hexafluorophosphate (HATU) to give a yellow solution. This was stirred overnight, after which HPLC showed no starting material. The solution was diluted with ethyl acetate (EtOAc, 500 mL) and washed with 1N HCl (2×), 1N NaOH (2×), and brine (1×). The organic phase was dried over anhydrous $MgSO_4$, filtered, and concentrated to a red oil. Chromatography with 2:1 hexanes/EtOAc vs. silica gave 12.56 g (25.5 mmol, 78%) of II as a yellow syrup (HPLC, >99%). MS: m/z 393 $(M-BOC)^+$, 494 $(M+H)^+$.

Amino ester III: In a 280 mL high-pressure vessel was dissolved 11.38 g (23.08 mmol) of II in 75 mL MeOH with stirring to give an orange solution. The vessel was flushed with nitrogen, and 200 mg (catalytic) of 10% palladium on carbon (Pd/C) was added. The sides of the vessel were washed with additional MeOH, and the vessel capped with a hydrogenation head. The mixture was placed under 60 psi $H_2$ with stirring overnight, after which HPLC showed no starting material remained. The mixture was filtered through Celite 545, the filter pad rinsed with additional MeOH, and the filtrate concentrated to a colorless oil, III, massing to 8.29 g (~quantitative). Material carried through. MS: m/z 360 $(M+H)^+$.

Benzyl carbamate methyl ester IV: In a 500 mL RB flask was dissolved 8.29 g (23.08 mmol) of III in 100 mL $CH_2Cl_2$ with stirring to give a colorless solution. To this was added 7.0 mL (50 mmol) of triethylamine ($Et_3N$), then 7.96 g (23.0 mmol) of CBZ-proline hydroxysuccinimide ester (CBZ-Pro-Osu) to give a colorless solution. This was stirred overnight, after which HPLC showed no starting material remaining. The solution was diluted with additional $CH_2Cl_2$, washed with 1N HCl (2×), 1N NaOH (2×), and the organic phase dried over $MgSO_4$, filtered, and the filtrate concentrated to a colorless oil. Chromatography with 3:1 EtOAc/hexanes vs. silica gave 12.22 g (20.7 mmol, 90%) of IV as a foamy, colorless glass (HPLC, >99%). MS: m/z 490 $(M-BOC)^+$, 591 $(M+H)^+$.

Amine trifluoroacetate salt V: In a 500 mL RB flask was dissolved 11.80 g (20.0 mmol) of IV in 120 mL $CH_2Cl_2$ with stirring to give a colorless solution. To this was added 20 mL (260 mmol, large excess) of trifluoroacetic acid (TFA), and the resulting solution was stirred for four hours, after which HPLC showed no starting material. The solution was concentrated, redissolved in $CH_2Cl_2$ and concentrated (2×), then placed under high vacuum to give 12.1 g (~quantitative) of V as a pale yellow oil. Material carried through. MS: m/z 491 $(M+H)^+$.

Diaryl urea methyl ester VI: In a 500 mL RB flask was dissolved 12.1 g (20 mmol) of V in 100 mL DMF with stirring to give a pale yellow solution. To this was added 17.4 mL (100 mmol) of DIEA, then 5.68 g (20.0 mmol) Intermediate 1 (oMePUPA-OH), and finally 9.12 g (24 mmol) of HATU to give a yellow solution. This was stirred overnight, after which HPLC showed no starting material remaining. The solution was diluted with EtOAc (500 mL) and washed with 1N HCl (2×), 1N NaOH (2×), and brine (1×). The organic phase was dried with $MgSO_4$, filtered, and the filtrate concentrated to a yellow oil/solid mixture. Chromatography with 2:1 acetonitrile/$CH_2Cl_2$ vs. silica gave 11.35 g (15.0 mmol, 75%) of VI as a slightly yellow, foamy solid (HPLC, >99%). MS: m/z 757 $(M+H)^+$, 779 $(M+Na^+)$.

Amino methyl ester VII: In a 280 mL high-pressure vessel was dissolved 8.0 g (10.6 mmol) of VI in 50 mL MeOH with stirring to give a slightly yellow solution. The vessel was flushed with nitrogen, and 250 mg (catalytic) of 10% Pd/C added. The sides of the vessel were washed with additional MeOH and the vessel capped with the hydrogenation head. The mixture was placed under 60 psi $H_2$ with stirring overnight, after which HPLC showed no starting material. The mixture was filtered through Celite 545, the filter pad rinsed with additional MeOH, and the filtrate concentrated to give 6.6 g (~quantitative) of VII as a white solid. Material carried through. MS: m/z 623 $(M+H)^+$.

Sulfonamide methyl ester VIII: In a 500 mL RB flask was dissolved 6.6 g (10.6 mmol) of VII in 100 mL dry $CH_2Cl_2$ with stirring to give a colorless solution. This was cooled to 0 degrees C. (ice bath), and 4.2 mL (30 mmol) of $Et_3N$ was added, followed by a solution of 3.68 g (15 mmol) of 3,5-dichlorobenzenesulfonyl chloride in 25 mL dry $CH_2Cl_2$ added dropwise over 10 minutes. The resulting solution was allowed to warm to RT and stirred for 2 hours, after which HPLC showed no starting material. The solution was diluted with additional $CH_2Cl_2$ and washed with 1N HCl (2×) and 1N NaOH (2×), then dried over $MgSO_4$, filtered, and the filtrate concentrated to a yellow solid. Chromatography with 2:1 $CH_2Cl_2$/acetonitrile vs. silica gave 6.68 g (8.0 mmol, 75%) of VIII as a white solid (HPLC, >99%). MS: m/z 832/833 $(M+H)^+$.

Carboxylic acid IX: In a 500 mL RB flask was dissolved 6.26 g (7.53 mmol) of VIII in 150 mL MeOH with stirring to give a colorless solution. This was cooled to 0 degrees C. (ice bath), and nitrogen was bubbled through the stirring solution for 30 minutes. To this was added 19 mL (38 mmol) of freshly-made 2M LiOH solution dropwise over 10 minutes, after which the solution was stirred at 0 degrees C. under nitrogen while the reaction progress was closely monitored by HPLC. After three hours, HPLC showed no starting material remaining. The solution was concentrated with minimal heating (volume reduced 50%), and slowly poured, in portions, into ice-cold 1N HCl to give a copious, brilliant-white precipitate. The solid was isolated via filtration, washed with cold distilled water, and air-dried overnight. The resulting fine, white solid was transferred to a glass jar and placed under high vacuum for 72 hours. The final mass was 6.02 g (7.36 mmol, 98%) of IX as a white powder (HPLC, >98%). MS: m/z 818/819 (M+H)$^+$, 841 (M+Na$^+$).

Homoserine 4-nitrophenyl Ether Benzyl Ester: To a solution of N-Boc homoserine benzyl ester 1 (1.2 g, 3.89 mmol), 4-nitrophenol (485 mg, 4.08 mmol) and triphenylphosphine (1.2 g, 4.66 mmol) in THF (10 mL) diethylazodicarboxylate (DEAD) (0.74 mL, 4.66 mmol) was added dropwise and the reaction was stirred at room temperature 12–24 h. Upon completion as judged by LC the solvents were removed to afford a viscous syrup. 4N HCl in dioxane (10 mL) was added rapidly and the solution was stirred at room temperature 3–6 h or until judged complete by LC. The reaction was concentrated to 1/4 volume and the product was precipitated out of ehtyl acetate to afford the hydrochloride salt II (96% pure, LC) as awhite solid (867 mg, 2.36 mmol, 61%). ESMS: (M−Cl)=331.

To a solution of Intermediate 4 (117 mg, 0.46 mmol) in DMF (3 mL) was added DIPEA (0.27 mL, 1.84 mmol) followed sequentially by the hydrochloride salt II (160 mg, 0.48 mmol) and HATU (239 mg, 0.63 mmol). The solution was stirred at room temperature for 2–4 h until judged complete by LC. The reaction was diluted with ethyl acetate (30 mL) and washed with 5% bicarbonate (10 mL), water

EXAMPLE 2

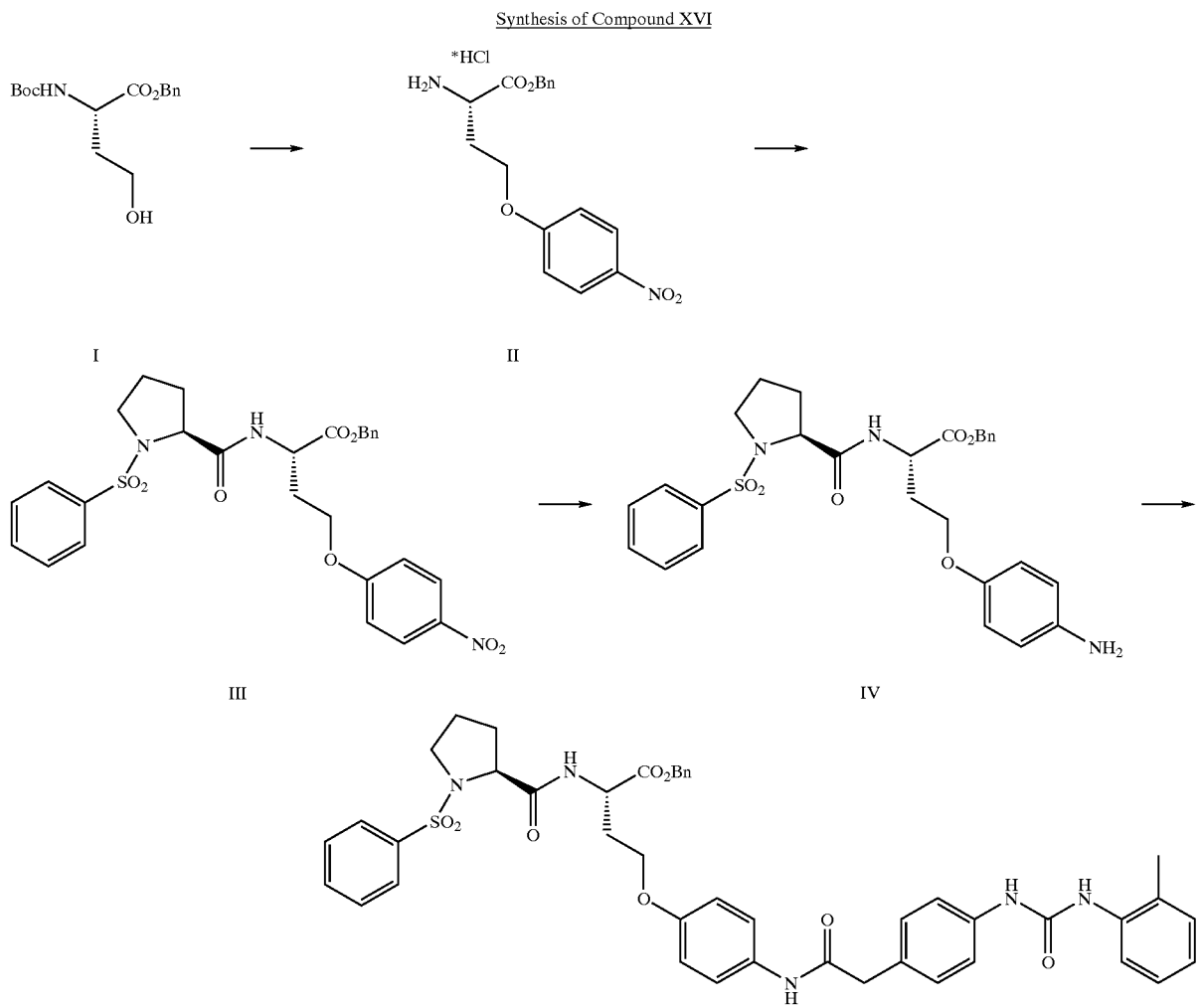

Synthesis of Compound XVI (10 mL), citric acid (10 mL), brine (2×10 mL) and dried over sodium sulfate to afford the crude product III as a tan foam (213 mg, 0.37 mmol, 82%) which was used directly.

ESMS: (M+H)=568.

The above material was dissolved in ethyl acetate (15 mL), 10% Pd/C (200 mg) was added and the reaction was subjected to hydrogenolysis at 50 psi for 4–6 h or until judged complete by LC. Filtration through celite and concentration afforded the crude aniline IV (144 mg, 0.32 mmol, 87%) as a tan foam which was used immediately.

ESMS: (M+H)=448.

The aniline (74 mg, 0.17 mmol) obtained above was dissolved in DMF (3 mL) and oMePUPA (52 mg, 0.18 mmol) was added followed by DIPEA (0.08 mL, 0.43 mmol) and HATU (69 mg, 0.18 mmol) and the reaction was stirred at room temperature 3–4 h until complete by LC. Purification by HPLC afforded Bio-8355 (39 mg, 0.054 mmol, 30%) as a white solid.

ESMS: (M+H)=714, (M−H)=712.

Compounds of this invention as shown in the following tables were prepared according to the method described above.

Compounds prepared according to General Method A include:

| Compound # | R3 | R1 | ESMS m/z |
|---|---|---|---|
| 5450 | | | 610.7 (M + H$^+$) |
| 5451 | | | 589.3 (M + H$^+$) |
| 6668 | | | 498.2 (M + H$^+$) |
| 6669 | | | 468.1 (M + H$^+$) |
| 6670 | | | 534.5 (M + H$^+$) |

Compounds prepared according to General Method A include:

| Compound # | R3 | R1 | ESMS m/z |
|---|---|---|---|
| 6671 | (quinoline-2-carboxamide with N-CH(CH3)CH2CH(CH3)2 group) | (5-methyl-pyrrolidin-2-one) | 484.4 (M + H+) |
| 6697 | oMePUPA-Pro | (2-methylpyrrolidine N-sulfonyl-3,5-dichlorophenyl) | 774.3 (M + H+) |
| 6714 | oMePUPA-N—MeLeu | (2-methylpyrrolidine N-sulfonyl-3,5-dichlorophenyl) | 804.4 (M + H+) |
| 6715 | (4-oxo-4,5,6,7-tetrahydrobenzofuran-3-carbonyl-2-methylpyrrolidine) | (2-methylpyrrolidine N-sulfonyl-3,5-dichlorophenyl) | 670 (M + H+) |
| 6716 | (4-oxo-4,5,6,7-tetrahydrobenzofuran-3-carboxamide with NH-CH(CH3)CH2CH(CH3)2) | (2-methylpyrrolidine N-sulfonyl-3,5-dichlorophenyl) | 686.4 (M + H+) |

-continued

Compounds prepared according to General Method A include:

| Compound # | R3 | R1 | ESMS m/z |
|---|---|---|---|
| 7171 | (4-oxo-4,5,6,7-tetrahydrobenzofuran-3-yl)-C(=O)-N(CH₃)-CH(CH₃)-CH₂-CH(CH₃)₂ | (S)-5-methyl-2-pyrrolidinone | 505.2 (M + H⁺) |
| 7172 | (4-oxo-4,5,6,7-tetrahydrobenzofuran-3-yl)-C(=O)-N(2-methylpyrrolidinyl) | (S)-5-methyl-2-pyrrolidinone | 475.2 (M + H⁺) |
| 7175 | (4-oxo-4,5,6,7-tetrahydrobenzofuran-3-yl)-C(=O)-NH-CH(CH₃)-CH₂-CH₂-S(O₂)CH₃ | (S)-5-methyl-2-pyrrolidinone | 541.3 (M + H⁺) |
| 7177 | (4-oxo-4,5,6,7-tetrahydrobenzofuran-3-yl)-C(=O)-NH-CH(CH₃)-CH₂-CH(CH₃)₂ | (S)-5-methyl-2-pyrrolidinone | 491.6 (M + H⁺) |
| 7514 | Ph-CF₂-C(=O)-NH-CH(CH₃)-CH(CH₃)₂ (actually Ph-CF₂-C(=O)-NH-CH(CH₃)-CH₂-... see structure) | 3,5-dichlorophenyl-SO₂-(2-methylpyrrolidin-1-yl) | 678.3 (M + H⁺) |

-continued
Compounds prepared according to General Method A include:
| Compound # | R3 | R1 | ESMS m/z |
|---|---|---|---|
| 7515 | 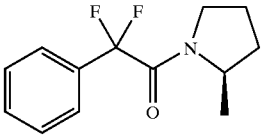 | 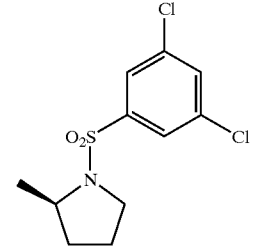 | 662.4 (M + H⁺) |
| 7516 | 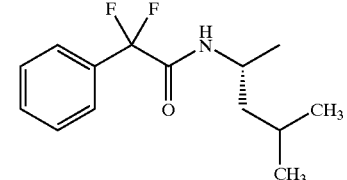 | 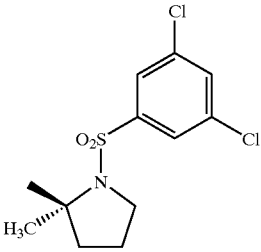 | 692.3 (M + H⁺) |
| 7517 | 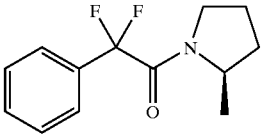 | 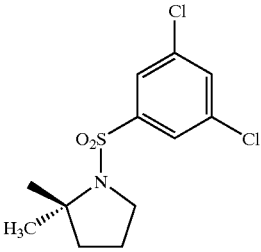 | 676.6 (M + H⁺) |
Compounds prepared according to General Method B include:
| BIO# | R3 | R1 | ESMS m/z |
|---|---|---|---|
| 7855 | oMePUPCH2 | 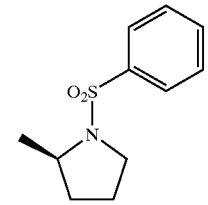 | 664.3 (M + H⁺) |
| 7856 | 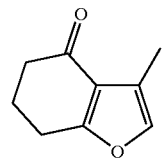 | 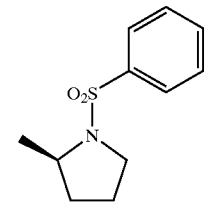 | 560.2 (M + H⁺) |

-continued

Compounds prepared according to General Method B include:

| BIO# | R3 | R1 | ESMS m/z |
|---|---|---|---|
| 7857 | 4-hydroxyphenethyl | (2S)-2-methyl-1-(phenylsulfonyl)pyrrolidine | 532.1 (M + H⁺) |
| 8066 | CH3 | (2S)-2-methyl-1-(phenylsulfonyl)pyrrolidine | 440.0 (M + H⁺) |
| 8067 | Bn | (2S)-2-methyl-1-(phenylsulfonyl)pyrrolidine | 516.0 (M + H⁺) |
| 8122 | oMePUPCH2 | 2-methyltetrahydrofuran | 539.5 (M + H⁺) |
| 8123 | 3-methyl-6,7-dihydrobenzofuran-4(5H)-one | 2-methyltetrahydrofuran | 435.4 (M + H⁺) |
| 8147 | cumyl (2-phenylpropan-2-yl) | 2-methyltetrahydrofuran | 419.0 (M + H⁺) |
| 8208 | oMePUPCH2 | CH3 | 469.0 (M + H⁺) |
| 8209 | oMePUPCH2 | oMePUPCH2 | 693.1 (M + H⁺) |
| 8210 | (2S)-1-(3,5-dichlorophenylsulfonyl)-2-methylpyrrolidine | CH3 | 507.9 (M + H⁺) |

-continued

Compounds prepared according to General Method B include:

| BIO# | R3 | R1 | ESMS m/z |
|---|---|---|---|
| 8211 | 3,5-dichlorophenylsulfonyl-(2S)-2-methylpyrrolidine | oMePUPCH2 | 732.3 (M + H+) |
| 8212 | 3,5-dichlorophenylsulfonyl-(2S)-2-methylpyrrolidine | 3,5-dichlorophenylsulfonyl-(2S)-2-methylpyrrolidine | 771.1 (M + H+) |
| 8449 | oMePUPCH2 | 2-phenyl-2-propyl | 573.0 (M + H+) |
| 8450 | Bn | 2-phenyl-2-propyl | 425.0 (M + H+) |
| 8451 | α,α-difluorophenylacetyl-2-acetylpyrrolidine | 2-phenyl-2-propyl | 557.9 (M + H+) |
| 8452 | 3-methyl-4,5,6,7-tetrahydrobenzofuran-4-one | 2-phenyl-2-propyl | 469.0 (M + H+) |
| 8453 | oMePUPCH2 | 2-(pyridin-3-yl)-2-cyclopentyl | 600.0 (M + H+) |
| 8455 | α,α-difluorophenylacetyl-2-acetylpyrrolidine | 2-(pyridin-3-yl)-2-cyclopentyl | 585.0 (M + H+) |

-continued

Compounds prepared according to General Method B include:

| BIO# | R3 | R1 | ESMS m/z |
|---|---|---|---|
| 8456 | (3-methyl-6,7-dihydrobenzofuran-4(5H)-one) | (1-methyl-1-(pyridin-3-yl)cyclopentyl) | 495.9 (M + H⁺) |
| 8457 | (2,2-difluoro-2-phenyl-1-(2-acetylpyrrolidin-1-yl)ethanone) | (2-methyltetrahydrofuran-2-yl) | 546.0 (M + Na⁺) |
| 8458 | oMePUPCH2 | (1-((3,5-dichlorophenyl)sulfonyl)-2-methylpyrrolidine) | 745.9 (M + H⁺) |
| 8459 | Bn | (1-((3,5-dichlorophenyl)sulfonyl)-2-methylpyrrolidine) | 597.9 (M + H⁺) |
| 8460 | (2,2-difluoro-2-phenyl-1-(2-acetylpyrrolidin-1-yl)ethanone) | (1-((3,5-dichlorophenyl)sulfonyl)-2-methylpyrrolidine) | 730.9 (M + H⁺) |
| 8461 | (3-methyl-6,7-dihydrobenzofuran-4(5H)-one) | (1-((3,5-dichlorophenyl)sulfonyl)-2-methylpyrrolidine) | 641.8 (M + H⁺) |
| 8462 | oMePUPCH2 | oMePUPA-Leu | 806.1 (M + H⁺) |
| 8463 | Bn | oMePUPA-Leu | 658.1 (M + H⁺) |

-continued
Compounds prepared according to General Method B include:
| BIO# | R3 | R1 | ESMS m/z |
|---|---|---|---|
| 8464 | 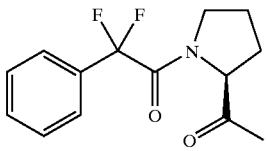 | oMePUPA-Leu | 791.0 (M + H⁺) |
| 8465 | 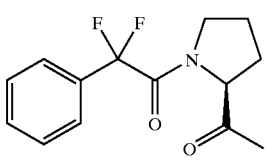 | CH3 | 454.0 (M + H⁺) |
| 8466 | 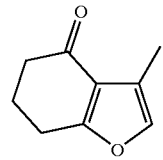 | CH3 | 365.0 (M + H⁺) |
| 8519 |  | 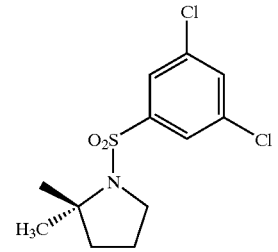 | 633.8 (M + H⁺) |
Compounds prepared according to General Method C include:
| Compound # | R3 | R1 | EMSM m/z |
|---|---|---|---|
| 5801 | 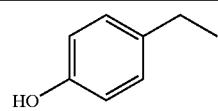 | 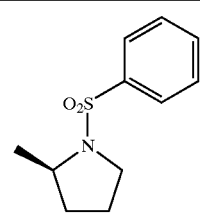 | 518.0 (M + H⁺) |
| 5803 | oMePUPCH2 | 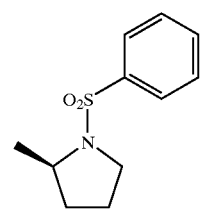 | 650.0 (M + H⁺) |
| 6655 | 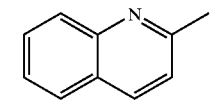 | CH3 | 344.2 (M + H⁺) |

-continued
Compounds prepared according to General Method C include:
| Compound # | R3 | R1 | EMSM m/z |
|---|---|---|---|
| 7081 | 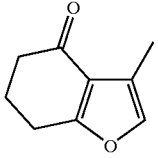 | 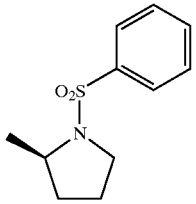 | 546.0 (M + H+) |
| 7111 | 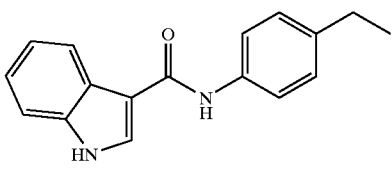 | 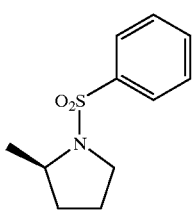 | 659.7 (M + H+) |
| 7117 | 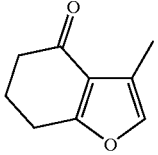 | CH3 | 351.2 (M + H+) |
| 7119 | oMePUPCH2 | CH3 | 452.8 (M − H+) |
| 7147 | 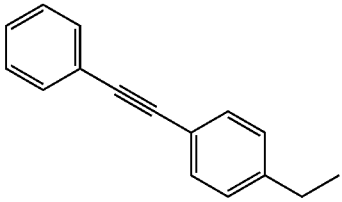 | 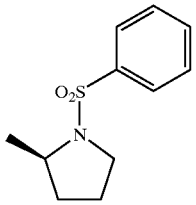 | 602.2 (M + H+) |
| 7148 | 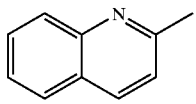 | 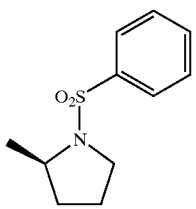 | 539.1 (M + H+) |
| 7150 | 2-Cl—Bn | 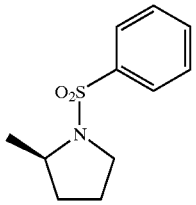 | 642.1 (M + H+) |
| 7156 | oMePUPCH2 | 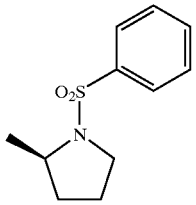 | 740.2 (M + H+) |

-continued

Compounds prepared according to General Method C include:

| Compound # | R3 | R1 | EMSM m/z |
|---|---|---|---|
| 7157 | (3-methyl-6,7-dihydrobenzofuran-4(5H)-one) | (1-(phenylsulfonyl)-2-methylpyrrolidine) | 636.1 (M + H⁺) |
| 7158 | CH3 | (1-(phenylsulfonyl)-2-methylpyrrolidine) | 516.2 (M + H⁺) |
| 7231 | H | (1-(3,5-dichlorophenylsulfonyl)-2-methylpyrrolidine) | 452.1 (M + H⁺) |
| 7233 | (5,5-dimethyl-2-(propan-2-ylidene)cyclohexane-1,3-dione) | (1-(3,5-dichlorophenylsulfonyl)-2-methylpyrrolidine) | 616.1 (M + H⁺) |
| 7234 | oMePUPA-Leu | (1-(3,5-dichlorophenylsulfonyl)-2-methylpyrrolidine) | 831.1 (M + H⁺) |
| 7235 | (3,6,6-trimethyl-6,7-dihydrobenzofuran-4(5H)-one) | (1-(3,5-dichlorophenylsulfonyl)-2-methylpyrrolidine) | 642.0 (M + H⁺) |

-continued
Compounds prepared according to General Method C include:
| Compound # | R3 | R1 | EMSM m/z |
|---|---|---|---|
| 7236 | 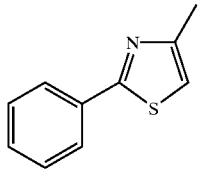 | 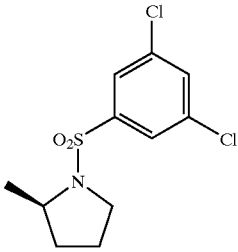 | 639.0 (M + H⁺) |
| 7241 | oMePUPCH2 | 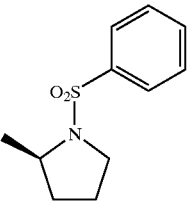 | 664.3 (M + H⁺) |
| 7255 | PhCH2CO-Pro | 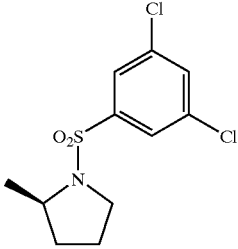 | 667.1 (M + H⁺) |
| 7256 | oMePUPA-Pro | 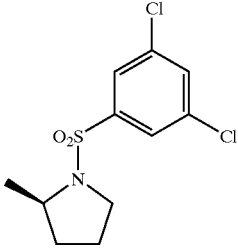 | 815.1 (M + H⁺) |
| 7257 | PhCH2CO-Leu | 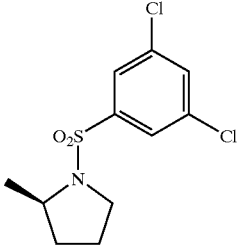 | 683.1 (M + H⁺) |

Compounds prepared according to General Method D include:
| Compound # | R1 | ESMS m/z |
|---|---|---|
| 5292 | 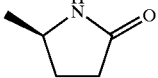 | 620.8 (M − H+) |
| 7080 | 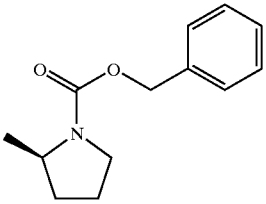 | 743.9 (M + H+) |
| 7092 | 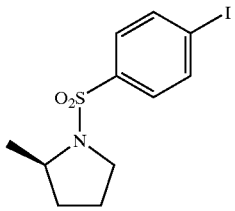 | 875.8 (M + H+) |
| 7093 | 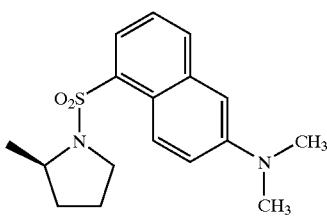 | 843.8 (M + H+) |
| 7109 | 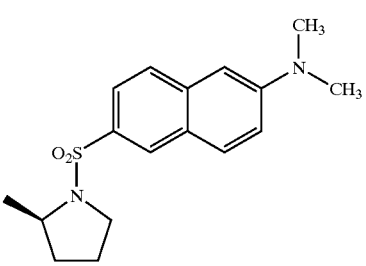 | 843.8 (M + H+) |
| 7116 | 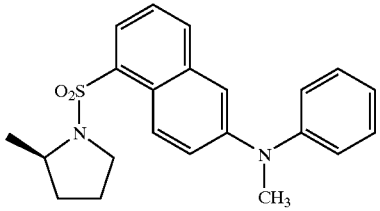 | 905.7 (M + H+) |
| 7181 | 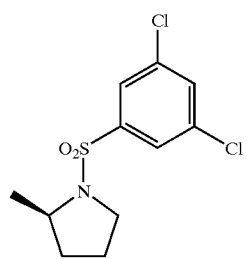 | 833.1 (M + H+) |

-continued
Compounds prepared according to General Method D include:
| Compound # | R1 | ESMS m/z |
|---|---|---|
| 7200 | 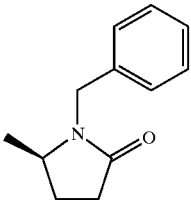 | 713.4 (M + H⁺) |
| 7328 | 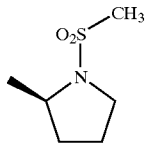 | 685.0 (M − H⁺) |
| 7398 | 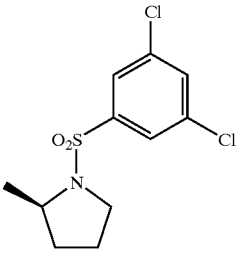 | 832.1 (M + H⁺) |
| 7662 | 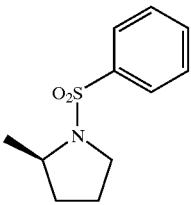 | 750.1 (M + H⁺) |
| 8221 | 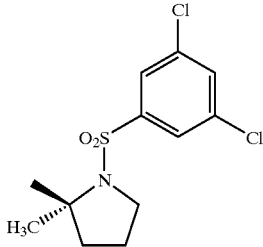 | 832.9 (M + H⁺) |
| 8290 | 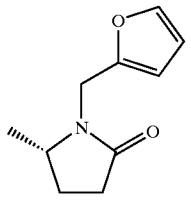 | 703.1 (M + H⁺) |
| 8291 | 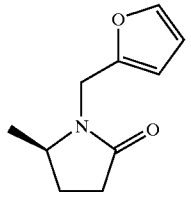 | 703.1 (M + H⁺) |

-continued

Compounds prepared according to General Method D include:

| Compound # | R1 | ESMS m/z |
|---|---|---|
| 8294 | (2-thienylmethyl)-5-methyl-pyrrolidin-2-one (2S) | 720.1 (M + H+) |
| 8295 | (2-thienylmethyl)-5-methyl-pyrrolidin-2-one | 720.1 (M + H+) |
| 8308 | N-methanesulfonyl-2-methyl-octahydroindole | 741.1 (M + H+) |
| 8309 | N-phenylsulfonyl-2-methyl-octahydroindole | 803.1 (M + H+) |
| 8341 | N-phenylsulfonyl-2-methyl-pyrrolidine | 750.0 (M + H+) |
| 8493 | N-phenylsulfonyl-3-methyl-morpholine | 765.9 (M + H+) |

-continued

Compounds prepared according to General Method D include:

| Compound # | R1 | ESMS m/z |
|---|---|---|
| 8528 | | 966.1 (M + H⁺) |
| 8555 | | 764.0 (M + H⁺) |
| 8571 | | 735.2 (M + H⁺) |
| 8582 | | 826.0 (M + H⁺) |
| 8583 | | 764.1 (M + H⁺) |
| 8586 | | 791.1 (M + H⁺) |

-continued
Compounds prepared according to General Method D include:
| Compound # | R1 | ESMS m/z |
|---|---|---|
| 8628 | 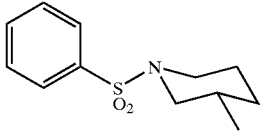 | 763.2 (M + H+) |
| 8642 | 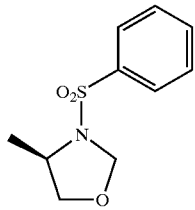 | 754.0 (M + H+) |
| 8674 | 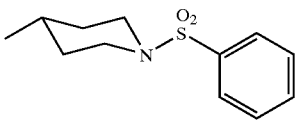 | 764.1 (M + H+) |
| 8929 | 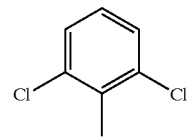 | 686.2 (M + H+) |
| 9120 | 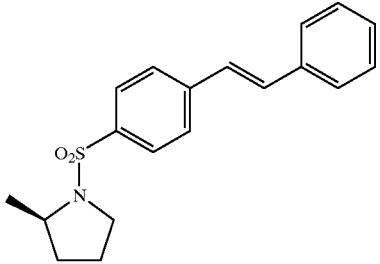 | 852.2 (M + H+) |
| 9140 | —CH3 | 554.2 (M + H+) |
| 9169 | 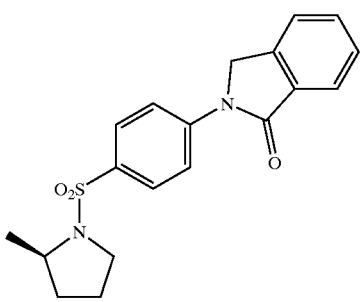 | 881.4 (M + H+) |
| 9170 | 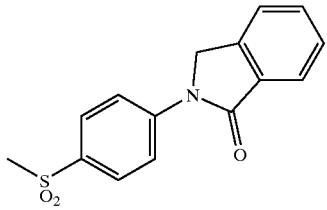 | 783.3 (M + H+) |

-continued

Compounds prepared according to General Method D include:

| Compound # | R1 | ESMS m/z |
|---|---|---|
| 9171 | *(4-acetylphenylsulfonyl-(2S)-methylpyrrolidine)* | 791.3 (M + H⁺) |
| 9182 | *(4-vinylphenylsulfonyl-(2S)-methylpyrrolidine)* | 775.5 (M + H⁺) |
| 9264 | *(3,5-dichlorophenylsulfonyl-(2S)-ethylpyrrolidine)* | 764.2 (M + H⁺) |
| 9437 | *(steroidal tetraol structure)* | 903.3 (M + H⁺) |

Compounds prepared according to General Method E included:

| Compound # | R3 | L | R1 | ESMS m/z |
|---|---|---|---|---|
| 5800 | Ac—Leu— | *(sec-butylbenzene)* | *(phenylsulfonyl-(2S)-methylpyrrolidine)* | 824.7 (M + H⁺) |

-continued
Compounds prepared according to General Method E included:
| Compound # | R3 | L | R1 | ESMS m/z |
|---|---|---|---|---|
| 7083 | oMePUPCH2 | 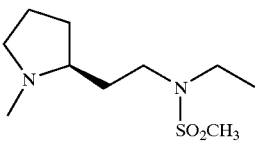 | 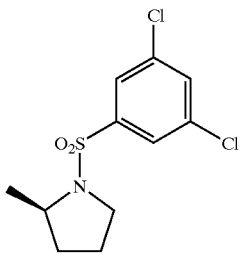 | 850.5 (M + H⁺) |
| 7155 | oMePUPCH2 | —(CH2)3— | 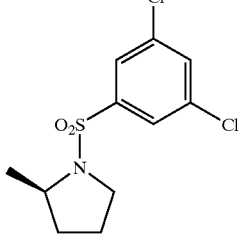 | 705.9 (M + H⁺) |
| 7168 | PhCH2CO—N—Me—Leu | —(CH2)2— | 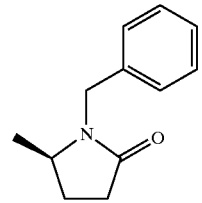 | 565.2 (M + H⁺) |
| 7528 | 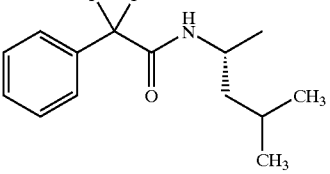 | —(CH2)2— | 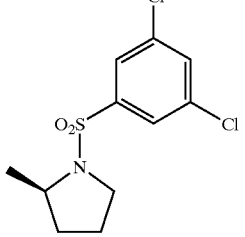 | 691.1 (M + H⁺) |
| 7530 | 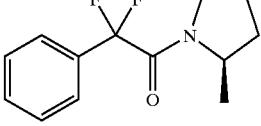 | —(CH2)2— | 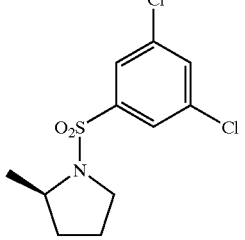 | 675.0 (M + H⁺) |
| 7552 | oMePUPA-α-N—Me-ε-CBz—Lys— | —(CH2)2— | 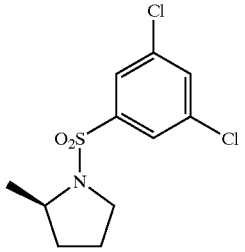 | 968.1 (M + H⁺) |

-continued
Compounds prepared according to General Method E included:
| Compound # | R3 | L | R1 | ESMS m/z |
|---|---|---|---|---|
| 7578 | oMePUPA-N—Me—Gly | —(CH2)2— | 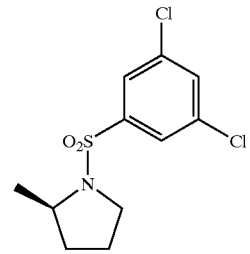 | 785.0 (M + Na+) |
| 9232 | oMePUPCH2 | 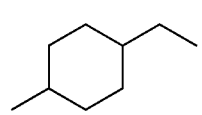 | 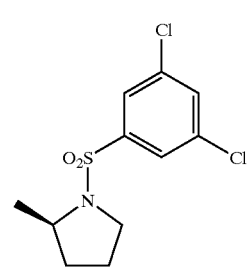 | 770.2 (M − H+) |
| 9233 | oMePUPA-Leu | 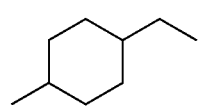 | 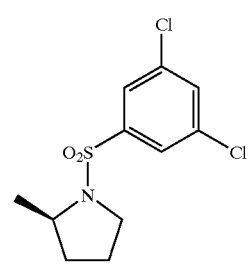 | 883.6 (M − H+) |
| 9234 | oMePUPCH2 | 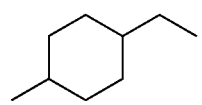 | 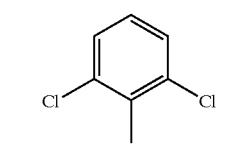 | 625.1 (M + H+) |
| 9235 | oMePUPA-Leu | 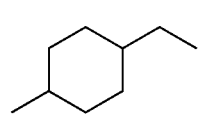 | 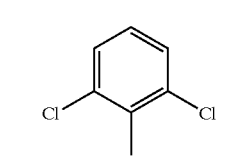 | 738.2 (M + H+) |
| 9236 | oMePUPCH2 | 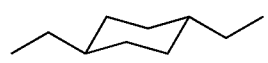 | 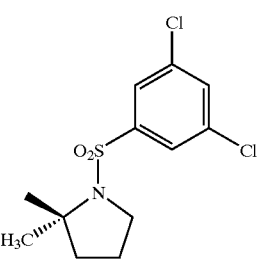 | 786.2 (M + H+) |

-continued

Compounds prepared according to General Method E included:

| Compound # | R3 | L | R1 | ESMS m/z |
|---|---|---|---|---|
| 9237 | oMePUPA-Leu | (trans-cyclohexyl-diyl) | 3,5-dichlorophenyl-SO2-N-[(2S)-2-methylpyrrolidinyl] | 897.4 (M − H+) |
| 9283 | oMePUPCH2 | (trans-cyclohexyl-diyl) | 2,6-dichloro-3-methylphenyl | 639.1 (M + H+) |
| 9239 | oMePUPA-Leu | (trans-cyclohexyl-diyl) | 2,6-dichloro-3-methylphenyl | 750.1 (M − H+) |
| 9270 | oMePUPCH2 | (1-methylpiperidin-4-yl) | 3,5-dichlorophenyl-SO2-N-[(2S)-2-methylpyrrolidinyl] | 742.1 (M − H+) |
| 9271 | oMePUPA-Leu | (1-methylpiperidin-4-yl) | 3,5-dichlorophenyl-SO2-N-[(2S)-2-methylpyrrolidinyl] | 855.4 (M − H+) |
| 9273 | oMePUPA-Leu | (1-methylpiperidin-4-yl) | 2,6-dichloro-3-methylphenyl | 710.1 (M + H+) |
| 9274 | oMePUPCH2 | (1-methylpiperidin-4-yl) | 3,5-dichlorophenyl-SO2-N-[(2S)-2-methylpyrrolidinyl] | 758.1 (M + H+) |

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the formula:

$$R^3\text{—}L\text{—}L'\text{—}R^1$$

wherein
- $R^1$ is optionally substituted pyrrolidinyl substituted with a —$SO_2$-optionally substituted phenyl group;
- L' is a hydrocarbon linker moiety having 1 carbon chain atom and is
  - (i) terminally attached to $R^1$ by —NHC(=O)— and
  - (ii) substituted with —COOH;
- L is $C_{1-4}$ alkyl terminally attached to $R^3$ by —C(=O)NH—; and
- $R^3$ is of the formula $R^4\text{—}Y^5\text{—}N(R^5)\text{—}CH(R^6)$— where R6 is alkyl; $R^5$ is hydrogen or alkyl; $Y^5$ is —C(=O)— and $R^4$ is an optionally substituted aralkyl;

or a pharmaceutically acceptable salt thereof.

2. The compound of claim 1, where said compound is:
compound number 5192 ($R^1$ is 1-(3,5-dichloro-benzenesulfonyl)-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 5283 ($R^1$ is 1-(3,5-dichloro-benzenesulfonyl)-2-pyrrolidinyl, L is $C_1$ alkyl terminally attached to $R^3$ by —C(=O)NH—, $R^5$ is hydrogen, $R^6$ is 2-methylpropyl, and $R^4$ is 4-(N'-(2-methylphenyl)ureido)benzyl);

compound number 6714 ($R^1$ is 1-(3,5-dichloro-benzenesulfonyl)-2-pyrrolidinyl, L is $C_1$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 7234 ($R^1$ is 1-(3,5-dichloro-benzenesulfonyl)-2-pyrrolidinyl, L is $C_4$ alkyl terminally attached to $R^3$ by —C(=O)NH—, $R^5$ is hydrogen, $R^6$ is 2-methylpropyl, and $R_4$ is 4-(N'-(2-methylphenyl)ureido)benzyl);

compound number 7662 ($R^1$ is 1-(benzenesulfonyl)-2S-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8221 ($R^1$ is 1-(3,5-dichloro-benzenesulfonyl)-2-methyl-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8309 ($R^1$ is 1-(benzenesulfonyl)-(4,5-(1,4-butanediyl))-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8341 ($R^1$ is 1-(benzenesulfonyl)-2R-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8342 ($R^1$ is 1-(benzenesulfonyl)-2S-pyrrolidinyl, the 1 chain carbon atom of L' having the R configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8343 ($R^1$ is 1-(benzenesulfonyl)-2R-pyrrolidinyl, the 1 chain carbon atom of L' having the R configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8367, ($R^1$ is 1-(benzenesulfonyl)-2S-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the R configuration, and $R_4$ is 4-(N'-(2-methylphenyl)ureido)benzyl);

compound number 8368 ($R^1$ is 1-(benzenesulfonyl)-2R-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the R configuration, and $R_4$ is 4-(N'-(2-methylphenyl)ureido)benzyl);

compound number 8469 ($R^1$ is 1-(3,5-dichlorobenzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R^4$ is 4-(N'-(2-methylphenyl)ureido)benzyl);

compound number 8491 ($R^1$ is 1-(benzenesulfonyl)-2-methyl-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(N'-(2-methylphenyl)ureido)benzyl);

compound number 8554 ($R^1$ is 1-(benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is (5-(2-(2-methylphenyl)amino)-1H-benzimidazolyl)methyl);

compound number 8642 ($R^1$ is 1-(benzenesulfonyl)-4-oxa-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8685 ($R^1$ is 1-(benzenesulfonyl)-4-(O-benzyl)carbamoyl-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound nunber 8689 ($R^1$ is 1-(benzenesulfonyl)-4-aminopyrrolidine, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8690 ($R^1$ is 1-(benzenesulfonyl)-4-(7-aminoheptamido)-2-pyrrolidinyl, L is $C_2$ alkyl terminally attached to $R^3$ by C(=O)NH—, $R^5$ is methyl, $R^6$ is 2-methylpropyl, and $R_4$ is 4-(N'-(2-methylphenyl)ureido)benzyl);

compound number 8698 ($R^1$ is 1-(benzenesulfonyl)-2-pyrrolidinyl, L is $C_2$ alkyl terminally attached to $R^3$ by —C(=O)NH—, $R^5$ is methyl, $R^6$ is 2-carboxylatoethyl, and $R_4$ is 4-(N'-(2-methylphenyl)ureido)benzyl);

compound number 8749 ($R^1$ is 1-(benzenesulfonyl)-4S-(7-amino-(3-(methoxy-PEG 20 k)-propanoyl)-heptarnido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8758, ($R^1$ is 1-(benzenesulfonyl)-4R-amino-(3-(methoxy-PEG 20 k)-propanoyl)-2-pyrrolidinyl, L is $C_2$ alkyl terminally attached to $R^3$ by C(=O)NH—, $R^5$ is methyl, $R^6$ is 2-methylpropyl, and $R_4$ is 4-(N'-(2-methylphenyl)ureido)benzyl);

compound number 8796 ($R^1$ is 1-(benzenesulfonyl)-4-(2-(4-hydroxyphenyl)acetamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8797 ($R^1$ is 1-(benzenesulfonyl)-4-(3-(4-hydroxyphenyl)propionamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8809 ($R^1$ is 1-(benzenesulfonyl)-4S-arnino-(3-(methoxy-PEG 20 k)-propanoyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9120 ($R^1$ is 1-((4-styryl)benzenesulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9169 ($R^1$ is 1-(4-(2,3-dihydroisoindol-1-one)benzenesulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9171 ($R^1$ is 1-(($^4$-acetylbenzene)sulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9182 ($R^1$ is 1-((4-vinylbenzene)sulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9227 ($R^1$ is 1-(benzenesulfonyl)-4-(7-amino-(3-(methoxy-PEG 30 k)-propanoyl)-heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9264 ($R^1$ is 1-((3,5-dichlorobenzenesulfonyl)-2-pyrrolidinyl)methyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9315 ($R^1$ is 1-(benzenesulfonyl)-4-(7-amino-(3-(methoxy-PEG 50 k)-propanoyl)-heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9418 ($R^1$ is 1-(benzenesulfonyl)-4-(7-amino-(3-(methoxy-PEG 20 k)-propanoyl)- heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9621 ($R^1$ is 1-(benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(1-(indol-3-yl)-formamido)-3-methoxybenzyl);

compound number 7200 ($R^1$ is 1-(benzenesulfonyl)-5-oxo-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8582 ($R^1$ is 1-(benzenesulfonyl)-5-phenyl-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8585 ($R^1$ is 1-((3,5-dichloro)benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(1-(indol-3-yl)-formamido)benzyl);

compound number 8723 ($R^1$ is 1-(benzenesulfonyl)-(4-(5-aminopentyl)acetamido)-2-pyrrolidinyl L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl); or compound number 8746 ($R^1$ is 1-(benzenesulfonyl)-4-amino-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl).

3. The compound of claim 1, where said compound is:

compound number 7200 ($R^1$ is 1-(benzenesulfonyl)-5-oxo-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8582 ($R^1$ is 1-(benzenesulfonyl)-5-phenyl-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8585 ($R^1$ is 1-((3,5-dichloro)benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(1-(indol-3-yl)-formamido)benzyl);

compound number 8723 ($R^1$ is 1-(benzenesulfonyl)-(4-(5-aminopentyl)acetamido)-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl); or compound number 8746 ($R^1$ is 1-(benzenesulfonyl)-4-amino-2-pyrrolidinyl, L is $C_2$ alkyl terminally attached to $R^3$ by C(=O)NH—, $R^5$ is methyl, $R^6$ is 2-methylpropyl, and $R_4$ is 4-(N'-(2-methylphenyl)ureido)benzyl).

4. A composition comprising a pharmaceutical carrier and an effective amount of a compound of the following formula:

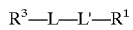

$R^1$ is optionally substituted pyrrolidinyl substituted with a —$SO_2$-optionally substituted phenyl group;

L' is a hydrocarbon linker moiety having 1 carbon chain atom and is
(i) terminally attached to $R^1$ by —NHC(=O)—; and
(ii) substituted with —COOH;
L is $C_{1-4}$ alkyl terminally attached to $R^3$ by —C(=O)NH; and
$R^3$ is of the formula $R^4$—$Y^5$—N($R^5$)—CH($R^6$)— where $R^6$ is alkyl; $R^5$ is hydrogen or alkyl; $Y^5$ is —C(=O)— and $R_4$ is an optionally substituted aralkyl;

or a pharmaceutically acceptable salt thereof.

5. The composition of claim 4, wherein said compound is compound number 5192 ($R^1$ is 1-(3,5-dichlorobenzenesulfonyl)-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 5283 ($R^1$ is 1-(3,5-dichlorobenzenesulfonyl)-2-pyrrolidinyl, L is $C_1$ alkyl terminally attached to $R^3$ by —C(=O)NH—, $R^5$ is hydrogen, $R^6$ is 2-methylpropyl, and $R^4$ is 4-(N'-(2-methylphenyl)ureido)benzyl);

compound number 6714 ($R^1$ is 1-(3,5-dichlorobenzenesulfonyl)-2-pyrrolidinyl, L is $C_1$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 7234 ($R^1$ is 1-(3,5-dichlorobenzenesulfonyl)-2-pyrrolidinyl, L is $C_4$ alkyl terminally attached to $R^3$ by —C(=O)NH—, $R^5$ is hydrogen, $R^6$ is 2-methylpropyl, and $R_4$ is 4-(N'-(2-methylphenyl)ureido)benzyl);

compound number 7662 ($R^1$ is 1-(benzenesulfonyl)-2S-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8221 ($R^1$ is 1-(3,5-dichlorobenzenesulfonyl)-2-methyl-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8309 ($R^1$ is 1-(benzenesulfonyl)-(4,5-(1,4-butanediyl))-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8341 ($R^1$ is 1-(benzenesulfonyl)-2R-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8342 ($R^1$ is 1-(benzenesulfonyl)-2S-pyrrolidinyl, the 1 chain carbon atom of L' having the R configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8343 ($R^1$ is 1-(benzenesulfonyl)-2R-pyrrolidinyl, the 1 chain carbon atom of L' having the R configuration, L is $C_2$ alkyl terminally attached to $R^3$ by —C(=O)NH—, $R^5$ is methyl, $R^6$ is 2-methylpropyl, wherein the carbon that $R^6$ is bound to has the S configuration, and $R_4$ is 4-(N'-(2-methylphenyl)ureido)benzyl);

compound number 8367, ($R^1$ is 1-(benzenesulfonyl)-2S-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the R configuration, and $R_4$ is 4-(N'-(2-methylphenyl)ureido)benzyl);

compound number 8368 ($R^1$ is 1-(benzenesulfonyl)-2R-pyrrolidinyl, the 1 chain carbon atom of L' having the S configuration, L is $C_2$ alkyl terminally attached to $R^3$ by —C(=O)NH—, $R^5$ is methyl, $R^6$ is 2-methylpropyl, wherein the carbon that $R^6$ is bound to has the R configuration, and $R_4$ is 4-(N'-(2-methylphenyl)ureido)benzyl);

compound number 8469 ($R^1$ is 1-(3,5-dichloro-benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R^4$ is 4-(N'-(2-methylphenyl)ureido)benzyl);

compound number 8491 ($R^1$ is 1-(benzenesulfonyl)-2-methyl-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(N'-(2-methylphenyl)ureido)benzyl);

compound number 8554 ($R^1$ is 1-(benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is (5-(2-(2-methylphenyl)amino)-1H-benzimidazolyl)methyl);

compound number 8642 ($R^1$ is 1-(benzenesulfonyl)-4-oxa-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8685 ($R^1$ is 1-(benzenesulfonyl)-4-(O-benzyl)carbamoyl-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8689 ($R^1$ is 1-(benzenesulfonyl)-4-aminopyrrolidine, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8690 ($R^1$ is 1-(benzenesulfonyl)-4-(7-aminoheptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8698 ($R^1$ is 1-(benzenesulfonyl)-2-pyrrolidinyl, L is $C_2$ alkyl terminally attached to $R^3$ by —C(=O)NH—, $R^5$ is methyl, $R^6$ is 2-carboxylatoethyl, and $R_4$ is 4-(N'-(2-methylphenyl)ureido)benzyl);

compound number 8749 ($R^1$ is 1-(benzenesulfonyl)-4S-(7-amino-(3-(methoxy-PEG 20 k)-propanoyl)-heptamido)-2-pyrrolidinyl, L is $C_2$ alkyl terminally attached to $R^3$ by C(=O)NH—, $R^5$ is methyl, $R^f$ is 2-methylpropyl, and $R_4$ is 4-(N'-(2-methylphenyl)ureido)benzyl);

compound number 8758, ($R^1$ is 1-(benzenesulfonyl)-4R-amino-(3-(methoxy-PEG 20 k)-propanoyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8796 ($R^1$ is 1-(benzenesulfonyl)-4-(2-(4-hydroxyphenyl)acetamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8797 ($R^1$ is 1-(benzenesulfonyl)-4-(3-(4-hydroxyphenyl)propionamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 8809 ($R^1$ is 1-(benzenesulfonyl)-4S-amino-(3-(methoxy-PEG 20 k)-propanoyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9120 ($R^1$ is 1-((4-styryl)benzenesulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9169 ($R^1$ is 1-(4-(2,3-dihydroisoindol-1-one)benzenesulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9171 ($R^1$ is 1-((4-acetylbenzene)sulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9182 ($R^1$ is 1-((4-vinylbenzene)sulfonyl)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9227 ($R^1$ is 1-(benzenesulfonyl)-4-(7-amino-(3-(methoxy-PEG 30 k)-propanoyl)-heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9264 ($R^1$ is 1-((3,5-dichloro-benzenesulfonyl)-2-pyrrolidinyl)methyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 9315 ($R^1$ is 1-(benzenesulfonyl)-4-(7-amino-(3-(methoxy-PEG 50 k)-propanoyl)-heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9418 ($R^1$ is 1-(benzenesulfonyl)-4-(7-amino-(3-(methoxy-PEG 20 k)-propanoyl)-heptamido)-2-pyrrolidinyl, L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl);

compound number 9621 ($R^1$ is 1-(benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(1-(indol-3-yl)-formamido)-3-methoxybenzyl);

compound number 7200 ($R^1$ is 1-(benzenesulfonyl)-5-oxo-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8582 ($R^1$ is 1-(benzenesulfonyl)-5-phenyl-2-pyrrolidinyl, L is $C_2$ alkyl terminally attached to $R^3$ by —C(=O)NH—, $R^5$ is methyl, $R^6$ is 2-methylpropyl, and $R^4$ is 4-(N'-(2-methylphenyl)ureido)benzyl);

compound number 8585 ($R^1$ is 1-((3,5-dichloro)benzenesulfonyl)-2-pyrrolidinyl, L is $C_2$ alkyl terminally attached to $R^3$ by —C(=O)NH—, $R^5$ is hydrogen, $R^6$ is 2-methylpropyl, and $R_4$ is 4-(1-(indol-3-yl)-formamido)benzyl);

compound number 8723 ($R^1$ is 1-(benzenesulfonyl)-(4-(5-aminopentyl)acetamido)-2-pyrrolidinyl L is $C_2$ alkyl terminally attached to $R^3$ by —C(=O)NH—, $R^5$ is methyl, $R^6$ is 2-methylpropyl, and $R_4$ is 4-(N'-(2-methylphenyl)ureido)benzyl); or compound number 8746 ($R^1$ is 1-(benzenesulfonyl)-4-amino-2-pyrrolidinyl, L is $C_2$ alkyl terminally attached to $R^3$ by —C(=CO)NH—, $R^5$ is methyl, $R^6$ is 2-methylpropyl, and $R_4$ is 4-(N'-(2-methylphenyl)ureido)benzyl).

6. The compound of claim 1, wherein said compound is 2-{[1-(3,5-dichloro-benzenesulfonyl)-pyrrolidine-2-carbonyl]-amino}-4-[4-methyl-2-(methyl-{2-[4-(3-o-tolyl-ureido)-phenyl]-acetyl}-amino)-pentanoylamino]-butyric acid.

7. The composition of claim 4, wherein said compound is 2-{[1-(3,5-dichloro-benzenesulfonyl)-pyrrolidine-2-carbonyl]-amino} -4-[4-methyl-2-(methyl-{2-[4-(3-o-tolyl-ureido)-phenyl]-acetyl}-amino)-pentanoylamino]-butyric acid.

\* \* \* \* \*